United States Patent [19]
Tabe et al.

[11] Patent Number: 5,719,297
[45] Date of Patent: Feb. 17, 1998

[54] VITAMIN $D_3$ DERIVATIVES AND PRODUCTION PROCESS THEREOF

[75] Inventors: Masayasu Tabe; Atsuo Hazato; Kenji Manabe; Qingzhi Gao; Hiroko Tanaka, all of Hino, Japan

[73] Assignee: Teijin Limited, Osaka, Japan

[21] Appl. No.: 591,547

[22] PCT Filed: Jun. 7, 1995

[86] PCT No.: PCT/JP95/01145

§ 371 Date: Feb. 6, 1996

§ 102(e) Date: Feb. 6, 1996

[87] PCT Pub. No.: WO95/33716

PCT Pub. Date: Dec. 14, 1995

[30] Foreign Application Priority Data

| Jun. 7, 1994 | [JP] | Japan | 6-125144 |
| Sep. 14, 1994 | [JP] | Japan | 6-220185 |
| Sep. 19, 1994 | [JP] | Japan | 6-223229 |

[51] Int. Cl.⁶ ............ C07D 307/26; C07C 401/00
[52] U.S. Cl. ............................. 549/323; 552/653
[58] Field of Search ............... 549/323; 552/653

[56] References Cited

FOREIGN PATENT DOCUMENTS

| 0619305 | 10/1994 | European Pat. Off. |
| 712843A1 | 5/1996 | European Pat. Off. |
| 58-118516 | 7/1983 | Japan |
| 58-210011 | 12/1983 | Japan |
| 60-185715 | 9/1985 | Japan |

OTHER PUBLICATIONS

Journal of Organic Chemistry, vol. 48, No. 23, 1983. Easton US, pp. 4433–4436.
Journal of the American Chemical Society, vol. 114, No. 5, 26 Feb. 1992, DC US, pp.1924–1925.
Horst, R.L. et al., Recent Developments in Quantitation of Vitamin $D_2$ and Vitamin $D_3$ and Their Metabolites in Biologic Fluids., Proc. Workshop Vitam. D, 1985, 6th (Vitam. D), pp. 807–816.
Ishizuka, S. et al., Biological Activity and Characteristics of $1\alpha$, 25–(OH)$_2$ $D_3$–26, 23–Lactone., Proc. Workshop Vitam. D, 1985, 6th (Vitam. D), pp. 402–403.
Archives of Biochemistry and Biophysics, 204, 387–391, Oct. 1, 1980.
FEBS Letters, 134, 207–211, Nov. 1981.
Chemical Abstracts, vol. 098, No. 13, Mar. 28, 1983; abstract No. 106082 Shiina Y et al: "Biological activity of 24,24–difluoro–1.alpha., 25–dihydroxyvitami n D3 and 1.alpha., 25–dihydroxyvitamin D3–26,23–lactone in inducing differentialtion of human myeloid leukemia cells" Xp002002153 * abstract * & Arch. Biochem. Biophys., vol. 220, No. 1, 1983, pp. 90–94.

Chemical Abstracts, vol. 100, No. 14, 2 Apr. 1984; abstract No. 109113, "Antitumor capsules containing 1.alpha., 25–dihydroxyvitamin D3–26, 23–lactone" & JP–A–58 210 011 (Kureha Chemical Co. Ltd.) 31 May 1982.

*Primary Examiner*—Amelia Averill Owens
*Attorney, Agent, or Firm*—Sughrue, Mion, Zinn, Macpeak & Seas, PLLC

[57] ABSTRACT

A vitamin $D_3$ derivative represented by the following formula:

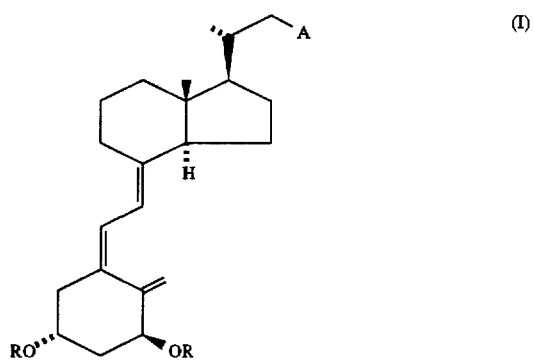

(I)

wherein, R is, independently, a hydrogen atom, tri($C_1$ to $C_7$ hydrocarbon)silyl group, $C_2$ to $C_8$ acyl group, or group forming an acetal bond together with an oxygen atom of a hydroxyl group, A is

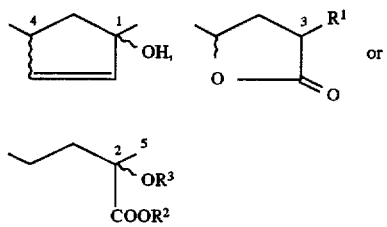

where, $R^1$ is a methyl group or methylene group, and when $R^1$ is a methylene group, the bond between the $R^1$ and the 3-position of the lactone ring is a double bond, $R^2$ is a hydrogen atom or $C_1$ to $C_3$ alkyl group, $R^3$ is a hydrogen atom, or $R^2$ and $R^3$ together indicate a substitutable single methylene group.

15 Claims, 2 Drawing Sheets

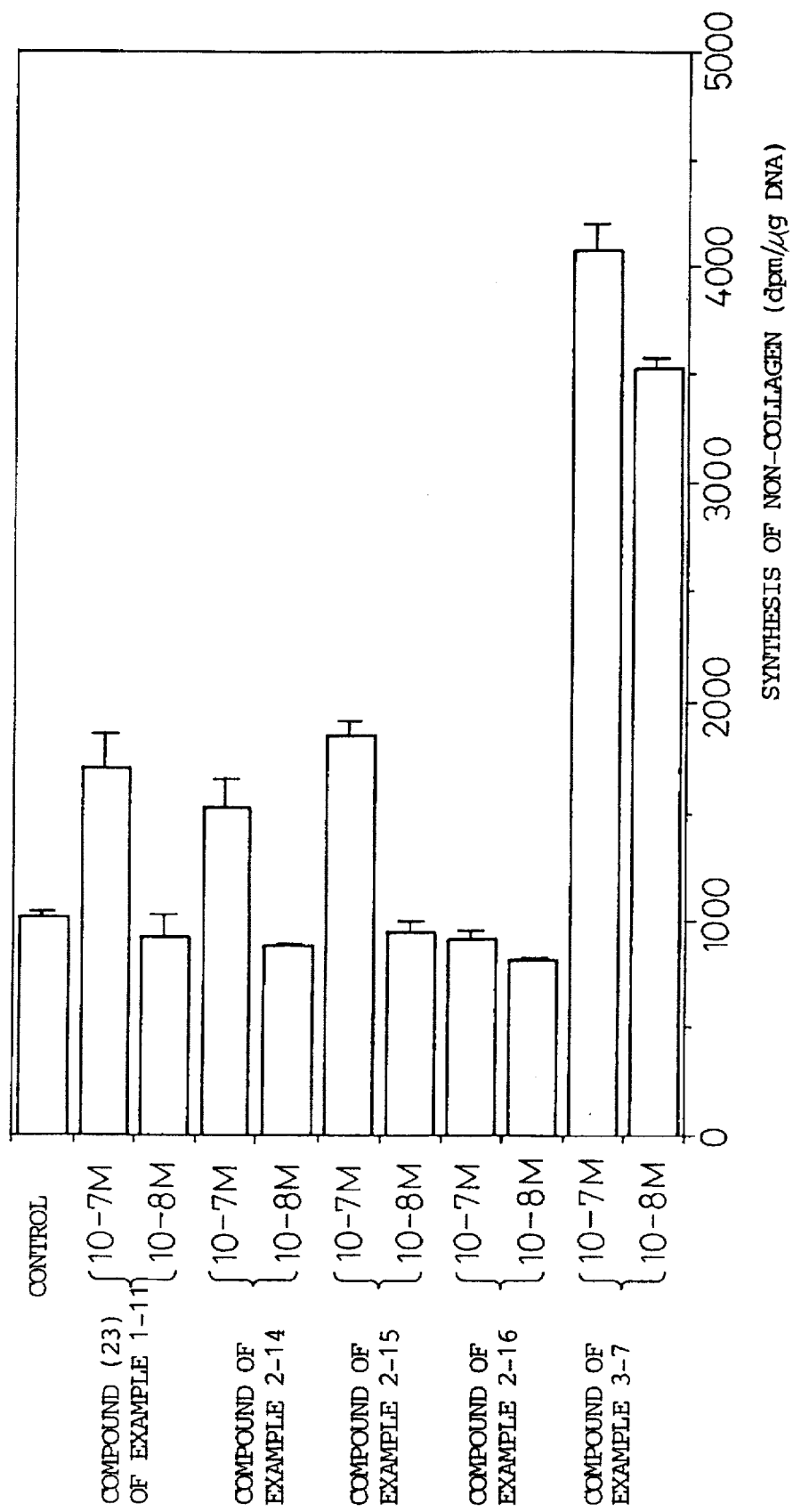

VITAMIN D₃ DERIVATIVES AND PRODUCTION PROCESS THEREOF

TECHNICAL FIELD

This application is a 371 of PCT/JP95/01145 filed Jun 7, 1995.

The present invention relates to a vitamin $D_3$ derivative useful as a pharmaceutical. More specifically, it relates to a 1α-hydroxy vitamin $D_3$ derivative useful as a pharmaceutical such as an agent for promoting bone formation, an agent for suppressing proliferation of tumor cells, an agent for high calcium blood diseases, and an immunosuppression agent, a production process thereof, and a production intermediate.

BACKGROUND ART

It is fully recognized through disclosures in patent publications and a large number of general references that vitamin $D_3$ metabolites play an extremely important role as substances controlling the metabolism of calcium and phosphates in the body. Recently, further, an increase has been seen in clinical application as drugs for the treatment of various diseases such as with the numerous vitamin $D_3$ metabolites found to have the function of inducing differentiation of tumorous bone marrow cells. On the other hand, recently, a novel vitamin $D_3$ active metabolite having an α-hydroxylactone ring at the steroid side chain has been found. [Arch. Bio-chem. Biophys., 204, 387–391 (1980); FEBS LETTERS, 134, 207–211 (1981)]. This compound is 1α,25-dihydroxy-vitamin $D_3$-26,23-lactone and is represented by the following structural formula:

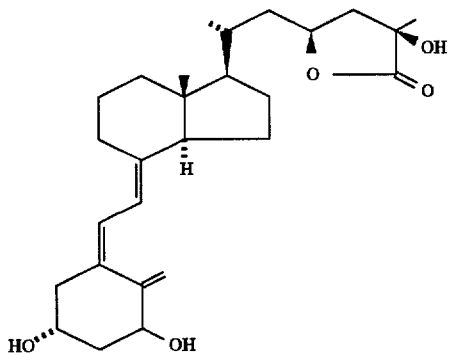

This compound has been reported to have an action for reducing the concentration of calcium in blood serum (Japanese Unexamined Patent Publication (Kokai) No. 58-118516), an action for suppressing the proliferation of tumor cells (Japanese Unexamined Patent Publication (Kokai) No. 58-210011), an action for promoting bone formation (Japanese Unexamined Patent Publication (Kokai) No. 60-185715), etc.

DISCLOSURE OF THE INVENTION

The object of the present invention is to provide a novel vitamin $D_3$ derivative having activity to promote bone formation, a production process therefor, and production intermediates.

In accordance with the present invention, there is provided a vitamin $D_3$ derivative having the following formula (I):

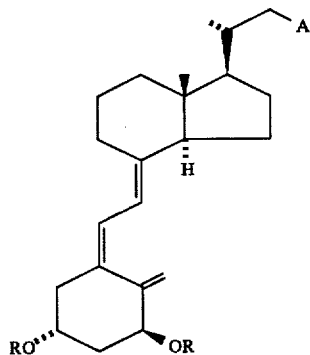

wherein, R is, independently, a hydrogen atom, tri($C_1$ to $C_7$ hydrocarbon)silyl group, $C_2$ to $C_8$ acyl group, or a group forming an acetal bond together with an oxygen atom of a hydroxyl group, A is

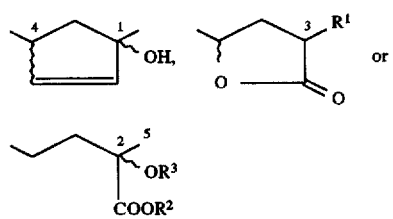

where, $R^1$ is a methyl group or methylene group, and when $R^1$ is a methylene group, the bond between $R^1$ and the 3-position of the lactone ring is a double bond, $R^2$ is a hydrogen atom or $C_1$ to $C_3$ alkyl group, $R^3$ is a hydrogen atom, or $R^2$ and $R^3$ together are a substitutable single methylene group.

BRIEF DESCRIPTION OF THE DRAWINGS

The present invention will now be explained in further detail with reference to the drawings.

FIG. 1 and FIG. 2 are respectively figures showing the results of synthesis of collagen and synthesis of noncollagen protein in the following Examples.

BEST MODE FOR WORKING THE INVENTION

Figure 1:
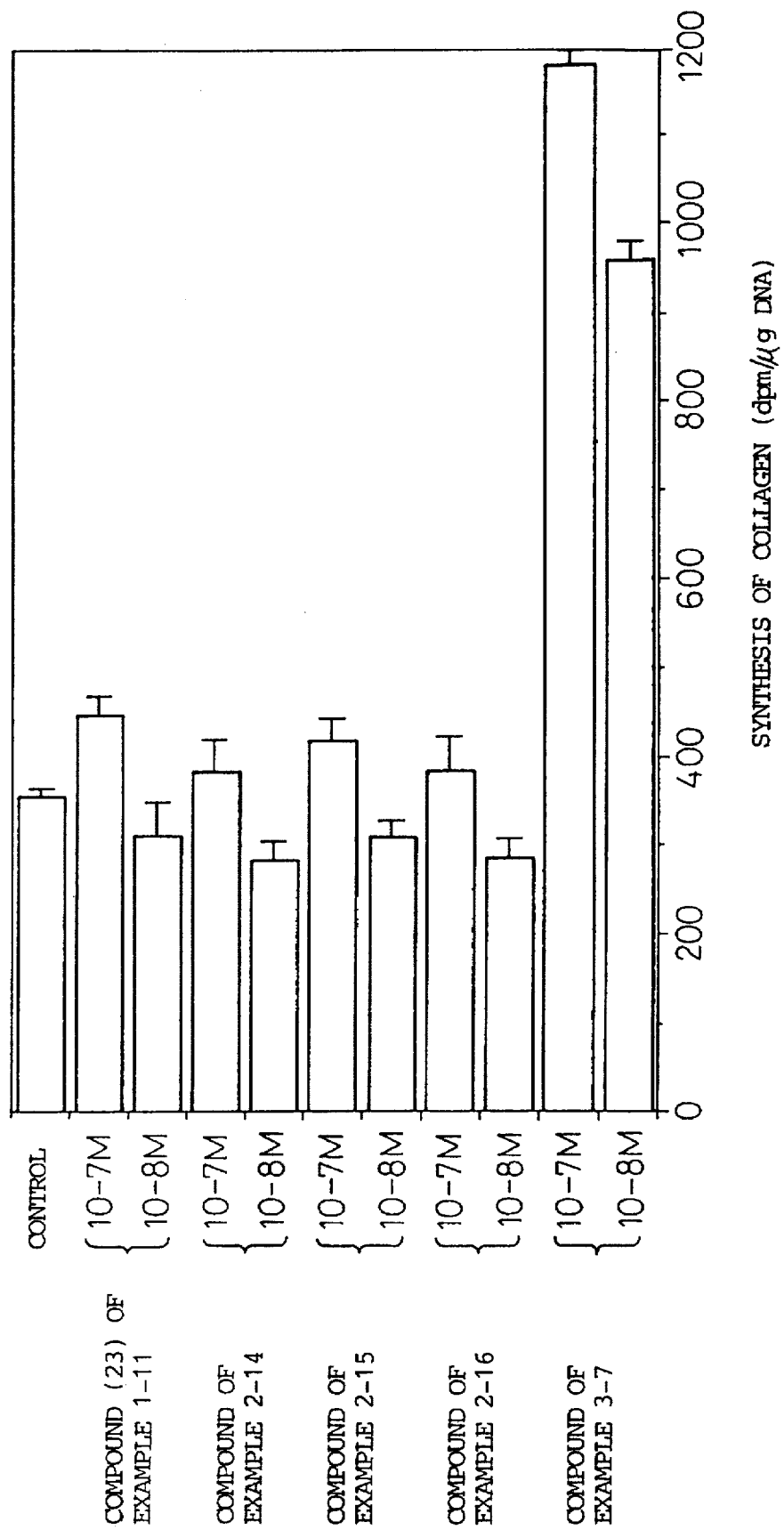

That is, according to the first aspect of the present invention, there is provided a vitamin $D_3$ derivative represented by the following formula (1-1):

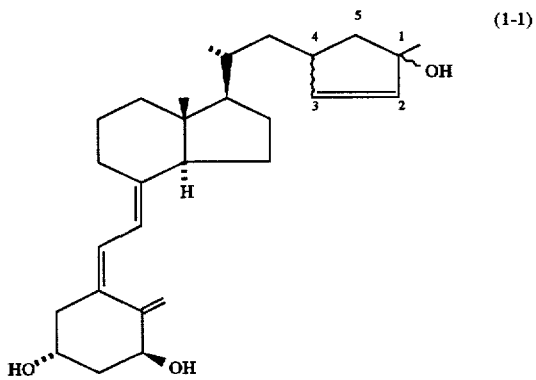

In the above formula (1-1), the configurations of the asymmetric centers of the C-1 position and C-4 position of the cyclopentene ring may be either of the (R) configuration or (S) configuration, respectively. Further, the present invention includes mixtures of any proportions of these four types of stereo isomers. Among them, ones where the asymmetric center of the C-1 position is the (R) configuration, ones where the asymmetric center of the C-4 position is the (S) configuration, and ones where the asymmetric center of the C-1 position is the (S) configuration and the asymmetric center of the C-4 position is the (S) configuration are preferred.

Specific examples of the preferred vitamin $D_3$ derivative of the first aspect of the present invention are as follows:

1) 23,24,25,26,27-pentanol-1α-hydroxy-22-[(1-hydroxy-1-methyl)-2-cyclopenten-4-yl]-vitamin $D_3$ 2) 23,24,25,26,27-pentanol-1α-hydroxy-22-[(1R,4S)-(1-hydroxy-1-methyl)-2-cyclopenten-4-yl]-vitamin $D_3$ 3) 23,24,25,26,27-pentanol-1α-hydroxy-22-[(1R,4R)-(1-hydroxy-1-methyl)-2-cyclopenten-4-yl]-vitamin $D_3$ 4) 23,24,25,26,27-pentanol-1α-hydroxy-22-[(1S,4R)-(1-hydroxy-1-methyl)-2-cyclopenten-4-yl]-vitamin $D_3$ 5) 23,24,25,26,27-pentanol-1α-hydroxy-22-[(1S,4S)-(1-hydroxy-1-methyl)-2-cyclopenten-4-yl]-vitamin $D_3$ Further, the present invention includes a production process of the vitamin $D_3$ derivative represented by the above formula (1-1).

That is, it includes a production process of a vitamin $D_3$ derivative represented by the above formula (1-1) characterized by reacting a cyclopentene derivative represented by the following formula (1-2):

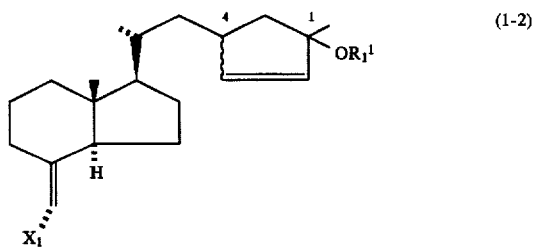

wherein $R^1_1$ is a hydrogen atom, a tri($C_1$ to $C_7$ hydrocarbon) silyl group, a $C_2$ to $C_7$ acyl group, or a group forming an acetal bond with an oxygen atom of a hydroxyl group, and $X_1$ is a bromine atom or iodine atom and an enyne derivative represented by the following formula (1-3)

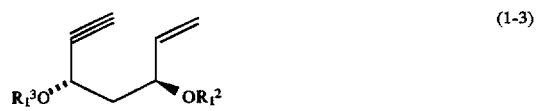

wherein $R^2_1$ and $R^3_1$ are a hydrogen atom, tri($C_1$ to $C_7$ hydrocarbon)silyl group, $C_2$ to $C_7$ acyl group, or a group forming an acetal bond with an oxygen atom of a hydroxyl group in the presence of a palladium catalyst to obtain a vitamin $D_3$ derivative represented by the following formula (1-4):

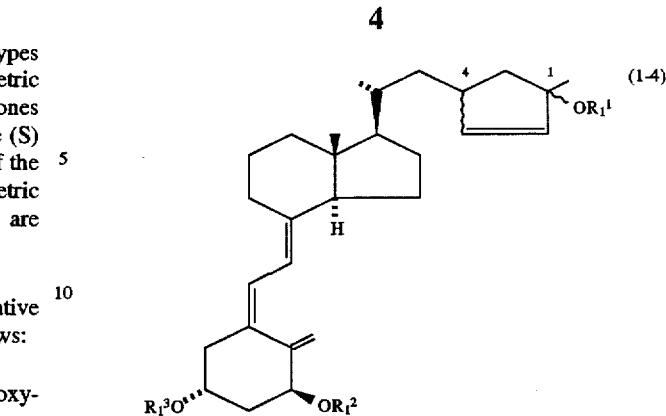

wherein, $R^1_1$, $R^2_1$, and $R^3_1$ are the same as defined above and optionally performing a deblocking reaction.

In the production process of a vitamin $D_3$ derivative according to the first aspect of the present invention, the configurations of the asymmetric centers of the C-1 position and C-4 position of the cyclopentene ring of the starting material, that is, the cyclopentene derivative represented by the above formula (1-2), may respectively be either of the (R) configuration or (S) configuration. Further, the derivative may be a mixture of any ratio of these stereo isomers. For example, when a cyclopentene derivative represented by the above formula (1-2) wherein the asymmetric center of the C-1 position of the cyclopentene ring is the (R) configuration and the asymmetric center of the C-4 position is the (S) configuration is used, the configurations of these portions are preserved during the reaction and a vitamin $D_3$ derivative represented by the above formula (1-1) wherein the asymmetric center of the C-1 position of the cyclopentene ring is the (R) configuration and the asymmetric center of the C-4 position is the (S) configuration is obtained.

In the same way, when a cyclopentene derivative represented by the above formula (1-1) where the asymmetric center of the C-1 position of the cyclopentene ring is the (S) configuration and the asymmetric center of the C-4 position is the (S) configuration is used, a vitamin D3 derivative represented by the above formula (1-1) wherein the asymmetric center of the C-1 position of the cyclopentene ring is the (S) configuration and the asymmetric center of the C-4 position is (S) configuration is obtained.

Here, when $R^1_1$, $R^2_1$, or $R^3_1$ is a tri($C_1$ to $C_7$ hydrocarbon) silyl group, specific examples are preferably a tri($C_1$ to $C_4$ alkyl)silyl group such as a trimethylsilyl, triethylsilyl, or t-butyldimethylsilyl group, a phenyl($C_1$ to $C_4$ alkyl)silyl group such as a t-butyldiphenylsilyl group, etc. Further, when $R^1_1$, $R^2_1$, or $R^3_1$ is a $C_1$ to $C_7$ acyl group, the specific examples are preferably an acetyl, propionyl, n-butyryl, pivaloyl, benzoyl, methoxycarbonyl, ethoxycarbonyl, benzyloxycarbonyl group, etc. Further, when $R^1_1$, $R^2_1$, or $R^3_1$ is a group forming an acetal bond with an oxygen atom of a hydroxyl group, specific examples are preferably, a methoxymethyl, (2-methoxyethoxy)methyl, 2-methoxy-2-propyl, 2-tetrahydrofuranyl, 2-tetrahydropyranyl group, etc.

The vitamin $D_3$ derivative represented by the above formula (1-4) is produced by reacting the cyclopentene derivative represented by the above formula (1-2) with an enyne derivative represented by the above formula (1-3) in the presence of a palladium catalyst. Here, the palladium catalyst used is a zero-valent or bivalent organopalladium compound. Examples of such a palladium compound, are tetrakis(triphenylphosphine) palladium or any mixture of a tris(dibenzylideneacetone) palladium, tris(dibenzylideneacetone)palladium chloroform, palladium acetate, etc. with a phosphorus compound such as triphenylphosphine or tributylphosphine (molar ratio of 1:1 to 1:10). As the palladium catalyst among these, a combination of tris(dibenzylideneacetone) palladium and triphenylphosphine (1:1 to 1:10) or tris(dibenzylideneacetone)palladium chloroform and triphenylphosphine (1:1 to 1:10) is preferred.

Here, the cyclopentene derivative represented by the above formula (1-2) and the enyne derivative represented by the above formula (1-3) stoichiometrically react equimolarly, but it is preferable to use a slight excess of the more readily available compound. Further, the palladium catalyst is used in a range of 0.1 to 100 molar %, preferably 1 to 20 molar %, with respect to the cyclopentene derivative of the above formula (1-2).

Examples of the reaction solvent used in this reaction are a hydrocarbon type solvent such as hexane and toluene, an ether type solvent such as diethyl ether, tetrahydrofuran, dioxane, and dimethoxyethane, a water-soluble solvent such as N,N-dimethylformamide and acetonitrile, and mixed solvents of the same. All of these are preferably used after sufficient deaeration.

As the reaction temperature, a range of from room temperature to the boiling point of the solvent is used. The reaction time differs depending on the reaction temperature. Usually, the reaction is preferably continued until one of the cyclopentene derivative represented by the above formula (1-2) or the enyne derivative represented by the above formula (1-3) is found to be consumed by an analytical means such as thin layer chromatography.

Further, to trap the acids such as the hydrogen halides in the reaction system, it is preferable to perform the reaction added with a base such as triethylamine or diisopropylethylamine. As the amount of the base, it is preferable to use at least one equivalent of the cyclopentene derivative represented by the above formula (1-2). It may also be used together as a solvent. Therefore, the vitamin $D_3$ derivative represented by the above formula (1-4) is produced in the reaction system, but it is possible to effect a deprotection reaction when necessary to obtain the vitamin $D_3$ derivative represented by the above formula (1-1).

As the method of the deblocking reaction, when deblocking for example the silyl groups, it is possible to use a known method (for example, Calveley, M. J., Tetrahedron, 20, 4609–4619, 1987). Examples of the deprotection agent in this case are tetrabutylammonium fluoride, pyridinium-p-toluene sulfonate, etc.

Further, in the process of the present invention, the compound represented by the above formula (1-2) which is used as a starting material may be synthesized in accordance with the following scheme:

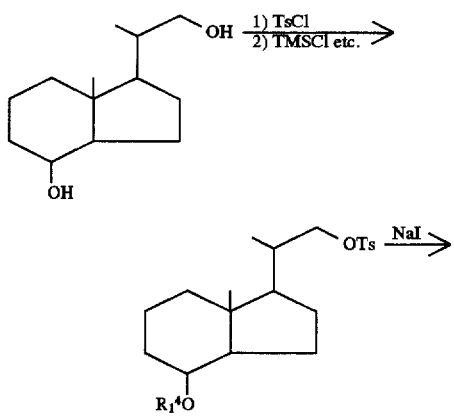

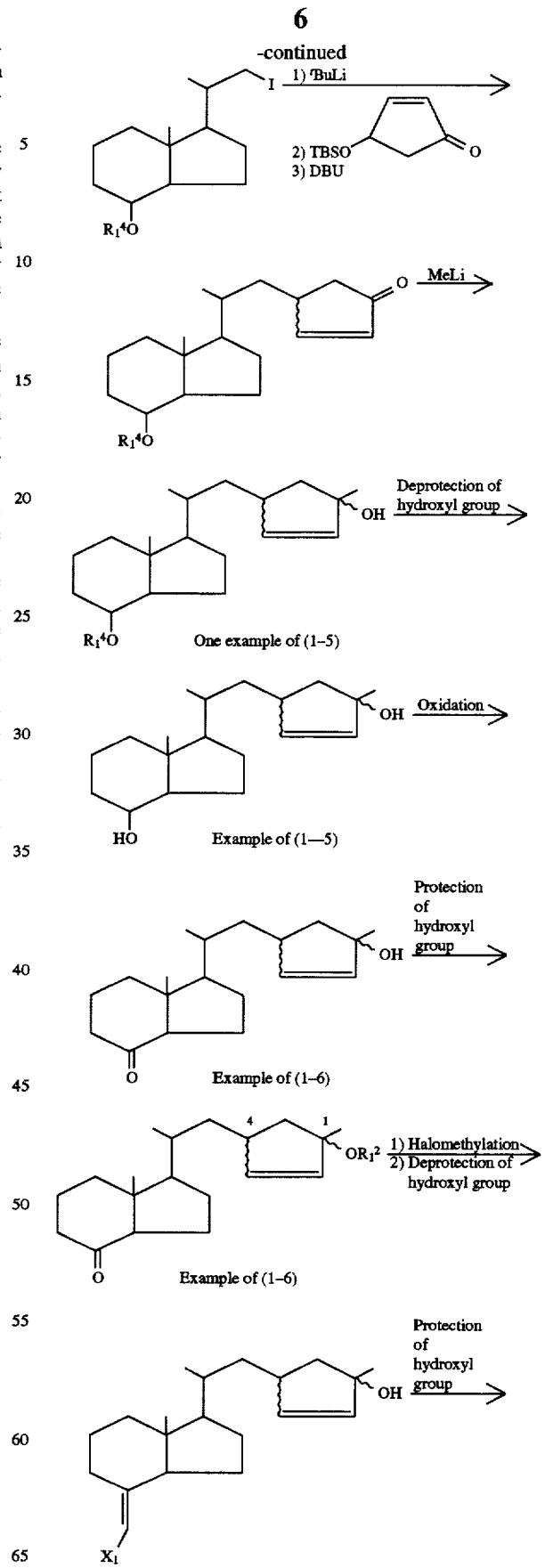

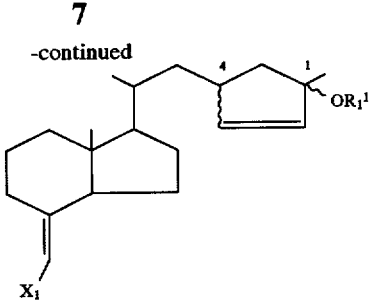

wherein, in the above scheme, $R^1_1$, $R^4_1$, and $R^{12}_1$ are a hydrogen atom, tri($C_1$ to $C_7$ hydrocarbon)silyl group, $C_2$ to $C_7$ acyl group, or group forming an acetal bond with an oxygen atom of a hydroxyl group.

Here, preferable specific examples of $R^4_1$ and $R^{12}_1$ are those as mentioned for the above $R^1_1$, $R^2_1$, and $R^3_1$.

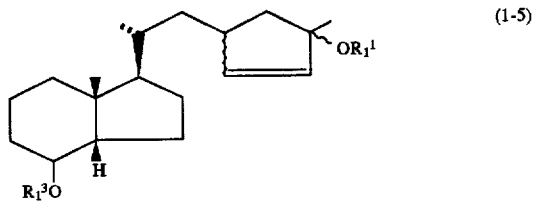

wherein, $R^1_1$ and $R^3_1$ may be the same or different and represent a hydrogen atom, tri($C_1$ to $C_7$ hydrocarbon)silyl group, $C_1$ to $C_7$ acyl group, or group forming an acetal bond with an oxygen atom of a hydroxyl group.

Preferable specific examples of the cyclopentene derivative of the present invention of the above formula (1-5) are as follows:

1) (1R,4R)-4-{(2R)-2-[(1R,7aR)-octahydro-4-trimethylsilyloxy-7a-methyl-1H-inden-1-yl]-propyl}-1-trimethylsilyloxy-1-methyl-2-cyclopentene 2) (1R,4S)-4-{(2R)-2-[(1R,7aR)-octahydro-4-trimethylsilyloxy-7a-methyl-1H-inden-1-yl]-propyl}-1-trimethylsilyloxy-1-methyl-2-cyclopentene 3) (1S,4R)-4-{(2R)-2-[(1R,7aR)-octahydro-4-trimethylsilyloxy-7a-methyl-1H-inden-1-yl]-propyl}-1-trimethylsilyloxy-1-methyl-2-cyclopentene 4) (1S,4S)-4-{(2R)-2-[(1R,7aR)-octahydro-4-trimethylsilyloxy-7a-methyl-1H-inden-1-yl]-propyl}-1-trimethylsilyloxy-1-methyl-2-cyclopentene 5) (1R,4R)-4-{(2R)-2-[(1R,7aR)-octahydro-4-(t-butyldimethylsilyloxy)-7a-methyl-1H-inden-1-yl]-propyl}-1-(t-butyldimethylsilyloxy)-1-methyl-2-cyclopentene 6) (1R,4S)-4-{(2R)-2-[(1R,7aR)-octahydro-4-(t-butyldimethylsilyloxy)-7a-methyl-1H-inden-1-yl]-propyl}-1-(t-butyldimethylsilyloxy)-1-methyl-2-cyclopentene 7) (1S,4R)-4-{(2R)-2-[(1R,7aR)-octahydro-4-(t-butyldimethylsilyloxy)-7a-methyl-1H-inden-1-yl]-propyl}-1-(t-butyldimethylsilyloxy)-1-methyl-2-cyclopentene 8) (1S,4S)-4-{(2R)-2-[(1R,7aR)-octahydro-4-(t-butyldimethylsilyloxy)-7a-methyl-1H-inden-1-yl]-propyl}-1-(t-butyldimethylsilyloxy)-1-methyl-2-cyclopentene 9) (1R,4R)-4-{(2R)-2-[(1R,7aR)-octahydro-4-hydroxy-7a-methyl-1H-inden-1-yl]-propyl}-1-methyl-2-cyclopenten-1-ol 10) (1R,4S)-4-{(2R)-2-[(1R,7aR)-octahydro-4-hydroxy-7a-methyl-1H-inden-1-yl]-propyl}-1-methyl-2-cyclopenten-1-ol 11) (1S,4R)-4-{(2R)-2-[(1R,7aR)-octahydro-4-hydroxy-7a-methyl-1H-inden-1-yl]-propyl}-1-methyl-2-cyclopenten-1-ol 12) (1S,4S)-4-{(2R)-2-[(1R,7aR)-octahydro-4-hydroxy-7a-methyl-1H-inden-1-yl]-propyl}-1-methyl-2-cyclopenten-1-ol

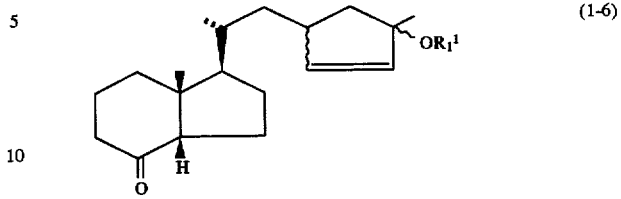

wherein, $R^1_1$ is a hydrogen atom, tri($C_1$ to $C_7$ hydrocarbon) silyl group, $C_1$ to $C_7$ acyl group, or group forming an acetal bond with an oxygen atom of a hydroxyl group.

Further, preferable specific examples of the cyclopentene derivative of the present invention of the above formula (1-6) are as follows:

1) (1R,4R)-4-{(2R)-2-[(1R,7aR)-octahydro-4-oxo-7a-methyl-1H-inden-1-yl]-propyl}-1-trimethylsilyloxy-1-methyl-2-cyclopentene 2) (1R,4S)-4-{(2R)-2-[(1R,7aR)-octahydro-4-oxo-7a-methyl-1H-inden-1-yl]-propyl}-1-trimethylsilyloxy-1-methyl-2-cyclopentene 3) (1S,4R)-4-{(2R)-2-[(1R,7aR)-octahydro-4-oxo-7a-methyl-1H-inden-1-yl]-propyl}-1-trimethylsilyloxy-1-methyl-2-cyclopentene 4) (1S,4S)-4-{(2R)-2-[(1R,7aR)-octahydro-4-oxo-7a-methyl-1H-inden-1-yl]-propyl}-1-trimethylsilyloxy-1-methyl-2-cyclopentene 5) (1R,4R)-4-{(2R)-2-[(1R,7aR)-octahydro-4-oxo-7a-methyl-1H-inden-1-yl]-propyl}-1-(t-butyldimethylsilyloxy)-1-methyl-2-cyclopentene 6) (1R,4S)-4-{(2R)-2-[(1R,7aR)-octahydro-4-oxo-7a-methyl-1H-inden-1-yl]-propyl}-1-(t-butyldimethylsilyloxy)-1-methyl-2-cyclopentene 7) (1S,4R)-4-{(2R)-2-[(1R,7aR)-octahydro-4-oxo-7a-methyl-1H-inden-1-yl]-propyl}-1-(t-butyldimethylsilyloxy)-1-methyl-2-cyclopentene 8) (1S,4S)-4-{(2R)-2-[(1R,7aR)-octahydro-4-oxo-7a-methyl-1H-inden-1-yl]-propyl}-1-(t-butyldimethylsilyloxy)-1-methyl-2-cyclopentene Further, in the above scheme, preferable specific examples of the cyclopentene derivative of the present invention of the above formula (1-2) are as follows:

1) (1R,4R)-4-{(2R)-2-[(1R,7aR)(4E)-octahydro-4-bromomethylene-7a-methyl-1H-inden-1-yl]-propyl}-1-trimethylsilyloxy-1-methyl-2-cyclopentene 2) (1R,4S)-4-{(2R)-2-[(1R,7aR)(4E)-octahydro-4-bromomethylene-7a-methyl-1H-inden-1-yl]-propyl}-1-trimethylsilyloxy-1-methyl-2-cyclopentene 3) (1S,4R)-4-{(2R)-2-[(1R,7aR)(4E)-octahydro-4-bromomethylene-7a-methyl-1H-inden-1-yl]-propyl}-1-trimethylsilyloxy-1-methyl-2-cyclopentene 4) (1S,4S)-4-{(2R)-2-[(1R,7aR)(4E)-octahydro-4-bromomethylene-7a-methyl-1H-inden-1-yl]-propyl}-1-trimethylsilyloxy-1-methyl-2-cyclopentene 5) (1R,4R)-4-{(2R)-2-[(1R,7aR)(4E)-octahydro-4-bromomethylene-7a-methyl-1H-inden-1-yl]-propyl}-1-(t-butyldimethylsilyloxy)-1-methyl-2-cyclopentene 6) (1R,4S)-4-{(2R)-2-[(1R,7aR)(4E)-octahydro-4-bromomethylene-7a-methyl-1H-inden-1-yl]-propyl}-1-(t-butyldimethylsilyloxy)-1-methyl-2-cyclopentene 7) (1S,4R)-4-{(2R)-2-[(1R,7aR)(4E)-octahydro-4-bromomethylene-7a-methyl-1H-inden-1-yl]-propyl}-1-(t-butyldimethylsilyloxy)-1-methyl-2-cyclopentene 8) (1S,4S)-4-{(2R)-2-[(1R,7aR)(4E)-octahydro-4-bromomethylene-7a-methyl-1H-inden-1-yl]-propyl}-1-(t-butyldimethylsilyloxy)-1-methyl-2-cyclopentene 9) (1R,4R)-4-{(2R)-2-[(1R,7aR)(4E)-octahydro-4-iodomethylene-7a-methyl-1H-inden-1-yl]-propyloxy}-1-trimethylsilyloxy-1-methyl-2-cyclopentene 10) (1R,4S)-4-{(2R)-2-[(1R,7aR)(4E)-octahydro-4-iodomethylene-7a-methyl-1H-inden-1-yl]-propyloxy}-1-trimethylsilyloxy-1-methyl-2-cyclopentene 11) (1S,4R)-4-{(2R)-2-[(1R,7aR)(4E)-octahydro-4-iodomethylene-7a-methyl-1H-inden-1-yl]-propyloxy}-1-trimethylsilyloxy-1-methyl-2-cyclopentene 12) (1S,4S)-4-{(2R)-2-[(1R,7aR)(4E)-octahydro-4-iodomethylene-7a-methyl-1H-inden-1-yl]-propyloxy}-1-trimethylsilyloxy-1-methyl-2-cyclopentene 13) (1R,4R)-4-{(2R)-2-[(1R,7aR)(4E)-octahydro-4-iodomethylene-7a-methyl-1H-inden-1-yl]-propyloxy}-1-(t-butyldimethylsilyloxy)-1-methyl-2-cyclopentene 14) (1R,4S)-4-{(2R)-2-[(1R,7aR)(4E)-octahydro-4-iodomethylene-7a-methyl-1H-inden-1-yl]-propyloxy}-1-(t-butyldimethylsilyloxy)-1-methyl-2-cyclopentene 15) (1S,4R)-4-{(2R)-2-[(1R,7aR)(4E)-octahydro-4-iodomethylene-7a-methyl-1H-inden-1-yl]-propyloxy}-1-(t-butyldimethylsilyloxy)-1-methyl-2-cyclopentene 16) (1S,4S)-4-{(2R)-2-[(1R,7aR)(4E)-octahydro-4-iodomethylene-7a-methyl-1H-inden-1-yl]-propyloxy}-1-(t-butyldimethylsilyloxy)-1-methyl-2-cyclopentene 17) (1R,4R)-4-{(2R)-2-[(1R,7aR)(4E)-octahydro-4-bromomethylene-7a-methyl-1H-inden-1-yl]-propyl}-1-methyl-2-cyclopenten-1-ol 18) (1R,4S)-4-{(2R)-2-[(1R,7aR)(4E)-octahydro-4-bromomethylene-7a-methyl-1H-inden-1-yl]-propyl}-1-methyl-2-cyclopenten-1-ol 19) (1S,4R)-4-{(2R)-2-[(1R,7aR)(4E)-octahydro-4-bromomethylene-7a-methyl-1H-inden-1-yl]-propyl}-1-methyl-2-cyclopenten-1-ol 20) (1S,4S)-4-{(2R)-2-[(1R,7aR)(4E)-octahydro-4-bromomethylene-7a-methyl-1H-inden-1-yl]-propyl}-1-methyl-2-cyclopenten-1-ol 21) (1R,4R)-4-{(2R)-2-[(1R,7aR)(4E)-octahydro-4-iodomethylene-7a-methyl-1H-inden-1-yl]-propyl}-1-methyl-2-cyclopenten-1-ol 22) (1R,4S)-4-{(2R)-2-[(1R,7aR)(4E)-octahydro-4-iodomethylene-7a-methyl-1H-inden-1-yl]-propyl}-1-methyl- 2-cyclopenten-1-ol 23) (1S,4R)-4-{(2R)-2-[(1R,7aR)(4E)-octahydro-4-iodomethylene-7a-methyl-1H-inden-1-yl]-propyl}-1-methyl-2-cyclopenten-1-ol 24) (1S,4S)-4-{(2R)-2-[(1R,7aR)(4E)-octahydro-4-iodomethylene-7a-methyl-1H-inden-1-yl]-propyl}-1-methyl-2-cyclopenten-1-ol According to the second aspect of the present invention, there is provided a vitamin $D_3$ derivative represented by the following formula (2-1):

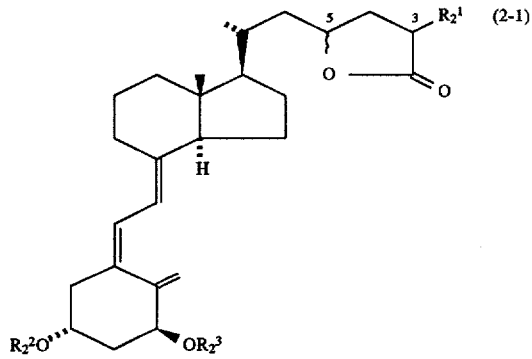

In the above formula (2-1), $R^1_2$ may be either of a methyl group or methylene group. Note that when $R^1_2$ is a methylene group, the bond between $R^1_2$ and the 3-position of the lactone ring is a double bond (same below). Further, when $R^1_2$ is a methyl group, the configuration of the asymmetric center of the 3-position of the lactone ring is the (S) configuration and the configuration of the asymmetric center of the 5-position may be either of the (S) or (R) configuration. Further, the derivative may be a mixture of any ratio of (S) and (R). Further, when $R^1_2$ is a methylene group, the configuration of the asymmetric center of the 5-position of the lactone ring may be either of the (S) or (R) configuration. Further, the derivative may be a mixture of any of (S) or (R). Among these, those where the asymmetric center of the 5-position is an (S) configuration are preferred.

In the above formula [1], $R^2_2$ and $R^3_2$ may be the same or different and represent a hydrogen atom, tri($C_1$ to $C_7$ hydrocarbon)silyl group, or $C_2$ to $C_8$ acyl group.

Here, when $R^2_2$ or $R^3_2$ is a tri($C_1$ to $C_7$ hydrocarbon)silyl group, examples of specific examples are preferably a tri($C_1$ to $C_4$ alkyl)silyl group such as a trimethylsilyl, triethylsilyl, and t-butyldimethylsilyl group, a phenyl($C_1$ to $C_4$ alkyl)silyl group such as a t-butyldiphenylsilyl group, and a tribenzylsilyl group. Further, a dimethyl(2,4,6-tri-t-butylphenoxy)silyl group may be used.

Further, when $R^2_2$ or $R^3_2$ is a $C_2$ to $C_8$ acyl group, the specific examples are preferably an acetyl, propionyl, n-butyryl, iso-butyryl, n-valeryl, iso-valeryl, caproyl, enanthyl, benzoyl, methoxycarbonyl, ethoxycarbonyl, benzyloxycarbonyl group, etc. Among these, a $C_2$ to $C_6$ acyl group, for example, an n-butyryl, iso-butyryl, methoxycarbonyl, ethoxycarbonyl group, and benzoyl group are preferred.

Preferable specific examples of the vitamin $D_3$ derivative represented by the above formula (2-1) of the second aspect of the present invention are as follows:

1) 1α-hydroxyvitamin $D_3$-26,23-lactone
2) 23(S),25(S)-1α-hydroxyvitamin $D_3$-26,23-lactone
S) 23(R),25(S)-1α-hydroxyvitamin $D_3$-26,23-lactone
4) 1α-hydroxy-25,27-dehydro-vitamin $D_3$-26,23-lactone
5) 23(S)-1α-hydroxy-25,27-dehydro-vitamin $D_3$-26,23-lactone
6) 23(R)-1α-hydroxy-25,27-dehydro-vitamin $D_3$-26,23-lactone The present invention further includes a process of production of the vitamin $D_3$ derivative of the above formula (2-1). That is, it provides a production process of the vitamin $D_3$ derivative represented by the above formula (2-1), characterized by reacting of a lactone compound represented by the following formula (2-2)

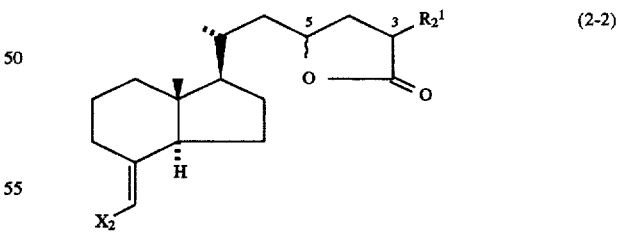

wherein $X_2$ is a bromine atom or iodine atom, $R^1_2$ is a methyl group or methylene group with an enyne compound represented by the following formula (2-10)

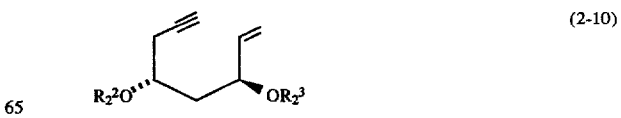

wherein, $R^2_2$ and $R^3_2$ are the same as defined above in the presence of a palladium catalyst.

This vitamin $D_3$ derivative can be made the vitamin $D_3$ derivative represented by the following formula (2-11)

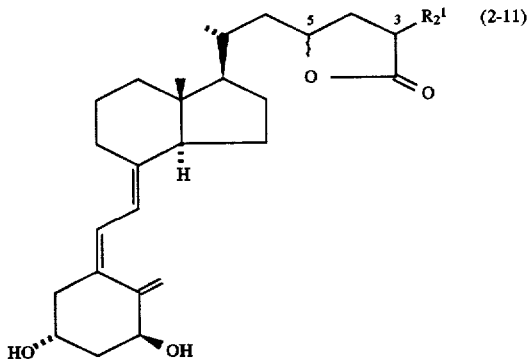

(2-11)

wherein, $R^1_2$ is the same as defined above optionally by effecting a deprotection reaction.

In the production process of the vitamin $D_3$ derivative according to the present invention, for the configurations of the 3-position and 5-position of the lactone ring of the lactone compound represented by the above formulas (2-2), (2-1), and (2-11), when $R^1_2$ is a methyl group, the 3-position is the (S) configuration, but the 5-position may be either of the (S) or (R) configuration. The derivative may also be any mixture thereof.

Further, when $R^1_2$ is a methylene group, the configuration of the 5-position of the lactone ring may be either of the (S) or (R) configuration. The derivative may also be any mixture thereof. For example, when a compound represented by the above formula (2-2) wherein the asymmetric center of the 3-position of the lactone ring is the (S) configuration and the asymmetric center of the 5-position is the (S) configuration is used, the configurations of these positions are preserved during the reaction and a lactone compound represented by the above formula (2-1) where the asymmetric center of the 3-position of the lactone ring is the (S) configuration and the asymmetric center of the 5-position is the (S) configuration is obtained.

In the same way, when a compound represented by the above formula (2-2) wherein the asymmetric center of the 3-position of the lactone ring is the (S) configuration and the asymmetric center of the 5-position is the (R) configuration is used, a lactone compound represented by the above formula (2-1) where the asymmetric center of the 3-position of the lactone ring is the (S) configuration and the asymmetric center of the 5-position is the (R) configuration is obtained.

The vitamin $D_3$ derivative represented by the above formula (2-11) is produced by reacting the lactone compound represented by the above formula (2-2) with an enyne compound represented by the above formula (2-10) in the presence of a palladium catalyst. Here, the palladium catalyst means, for example, a zero-valent or bivalent organopalladium. Examples of such a palladium compound are tetrakis(triphenylphosphine)palladium or a mixture of tris (dibenzylideneacetone)palladium, tris (dibenzylideneacetone)palladium chloroform, and palladium acetate with a phosphorus compound such as triphenylphosphine or tributylphosphine (molar ratio of 1:1 to 1:10). Among these, as the palladium catalyst, a combination of tris(dibenzylideneacetone)palladium and triphenylphosphine (1:1 to 1:10) or tris(dibenzylideneacetone) palladium chloroform and triphenylphosphine (1:1 to 1:10) is preferred.

Here, the lactone compound represented by the above formula (2-2) and the enyne compound represented by the above formula (2-10) stoichiometrically react equimolarly, but to ensure the reaction is reliably completed, it is usually preferable to use a slightly excess amount of either one of the two reactants, whichever is more readily available.

Further, the palladium catalyst is used in a range of 1 to 100 molar %, preferably 5 to 30 molar %, with respect to the lactone compound represented by the above formula (2-2).

Examples of the organic solvent used in the process of production, are a hydrocarbon type solvent such as hexane or toluene, an ether type solvent such as tetrahydrofuran or dioxane, a water-soluble solvent such as N,N-dimethylformamide or acetonitrile, and mixed solvents thereof. For all of these, it is important to sufficiently deaerate them before use.

As the reaction temperature, in general a range of from room temperature to the boiling point of the solvent is used. The reaction time differs according to the reaction solvent used and the reaction temperature, but usually the reaction is preferably performed until either of the lactone compound represented by the above formula (2-2) or the enyne compound represented by the above formula (2-10) is consumed as determined using an analytical means such as thin layer chromatography.

Further, in addition to the palladium catalyst, to trap the hydrogen halide, the reaction is preferably performed in the presence of a base such as, for example, triethylamine or diisopropylethylamine.

As the amount of the base, at least one equivalent of the lactone compound of the above formula (2-2) is preferable. The combined use as a solvent is also possible, if necessary.

Further, the vitamin $D_3$ derivative represented by the above formula (2-1) of the present invention may if necessary be made the vitamin $D_3$ derivative represented by the above formula (2-11) by deblocking.

As the deblocking reaction, for example, when deblocking the silyl groups, a known method (for example, Calvely, M. J., Tetrahedoron, 20, 4609 to 4619, 1987) may be used. Examples of the deblocking agent in this case are tetrabutylammonium fluoride, pyridinium-p-toluene sulfonate, etc.

The compound represented by the above formula (2-2) used as a starting material in the process of the present invention may, for example, be synthesized in accordance with the following scheme. When X is an iodine atom, the configuration differs in the same way.

[Synthesis scheme]
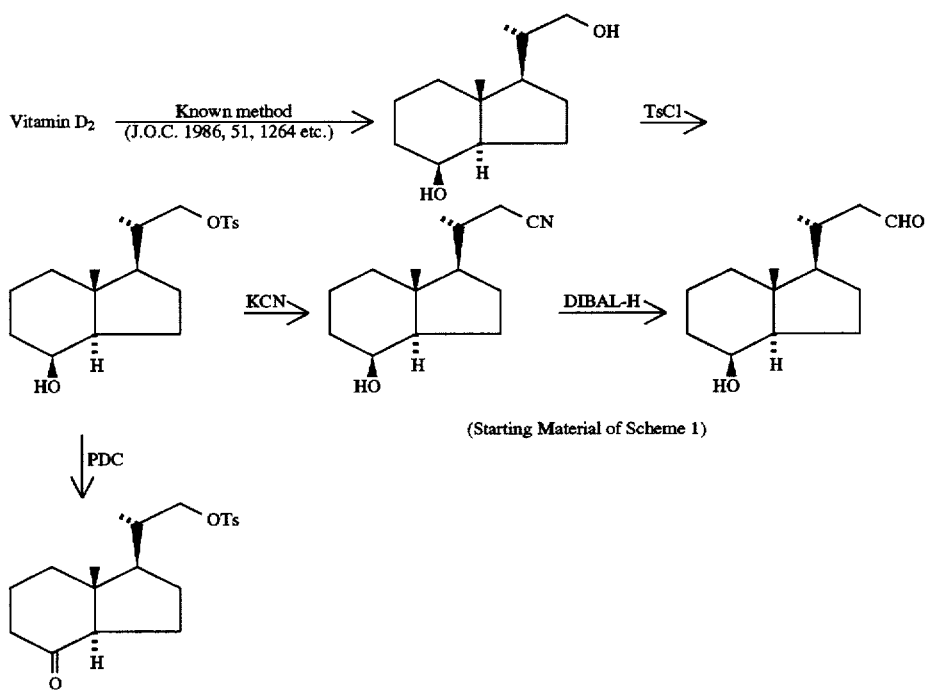
(Starting Material of Scheme 1)
(Starting Material of Scheme 2)
[Scheme 1]
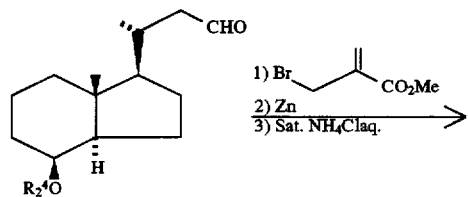
Wherein $R_2^4O$ is the same as defined above
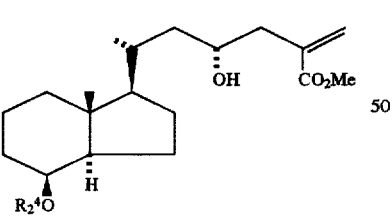
Example of (2-6)
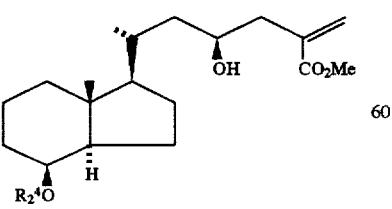
Example of (2-6)
-continued
[Scheme 1]
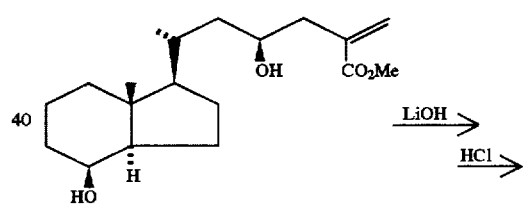
Example of (2-6)
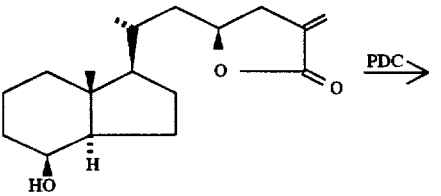
Example of (2-5)
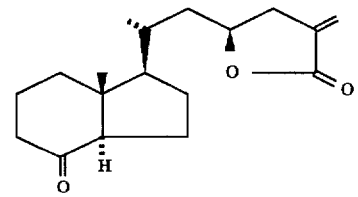
Example of (2-3)

15
-continued
[Scheme 1]
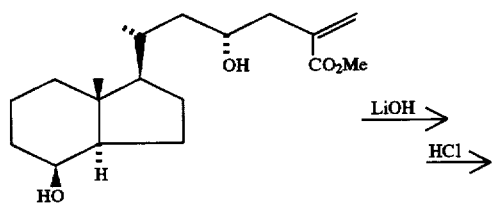
Example of (2-6)
LiOH →
HCl →
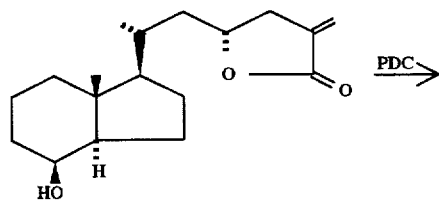
Example of (2-5)
PDC →
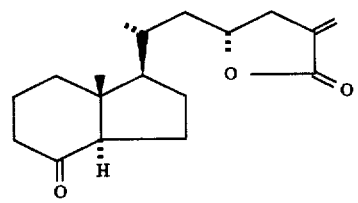
Example of (2-3)
H₂
Pd/C →
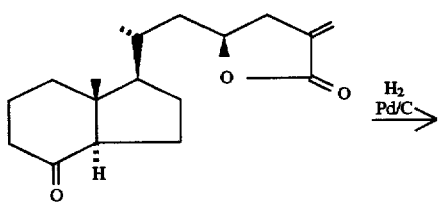
Example of (2-3)
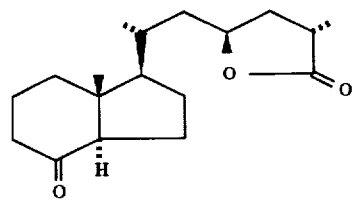
Example of (2-3)
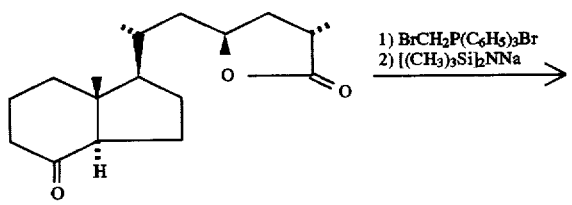
Example of (2-3)
1) BrCH₂P(C₆H₅)₃Br
2) [(CH₃)₃Si]₂NNa →
16
-continued
[Scheme 1]
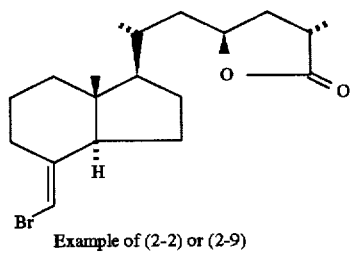
Example of (2-2) or (2-9)
[Scheme 2]
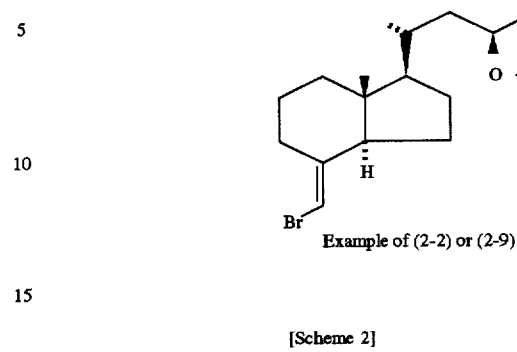
1) BrCH₂P(C₆H₅)₃Br
2) [(CH₃)₃Si]₂NNa →
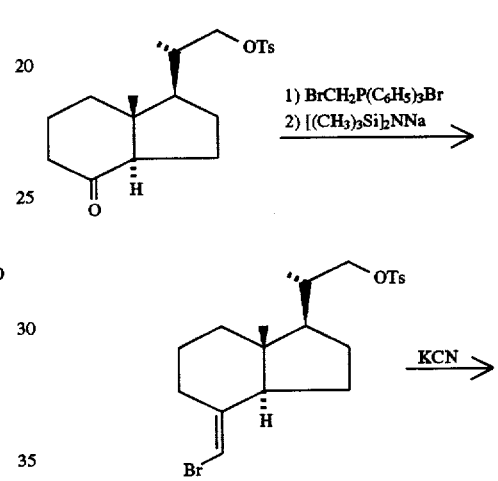
Example of (2-7)
KCN →
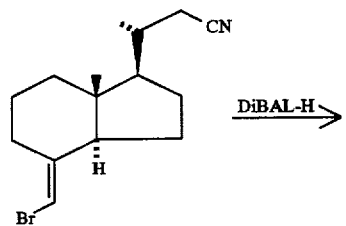
Example of (2-7)
DiBAL-H →
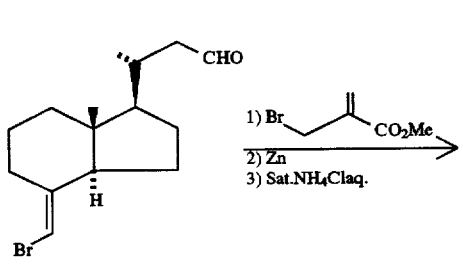
Example of (2-7)
1) Br‑CH₂‑C(=CH₂)‑CO₂Me
2) Zn
3) Sat.NH₄Cl aq.
→

[Scheme 2] -continued

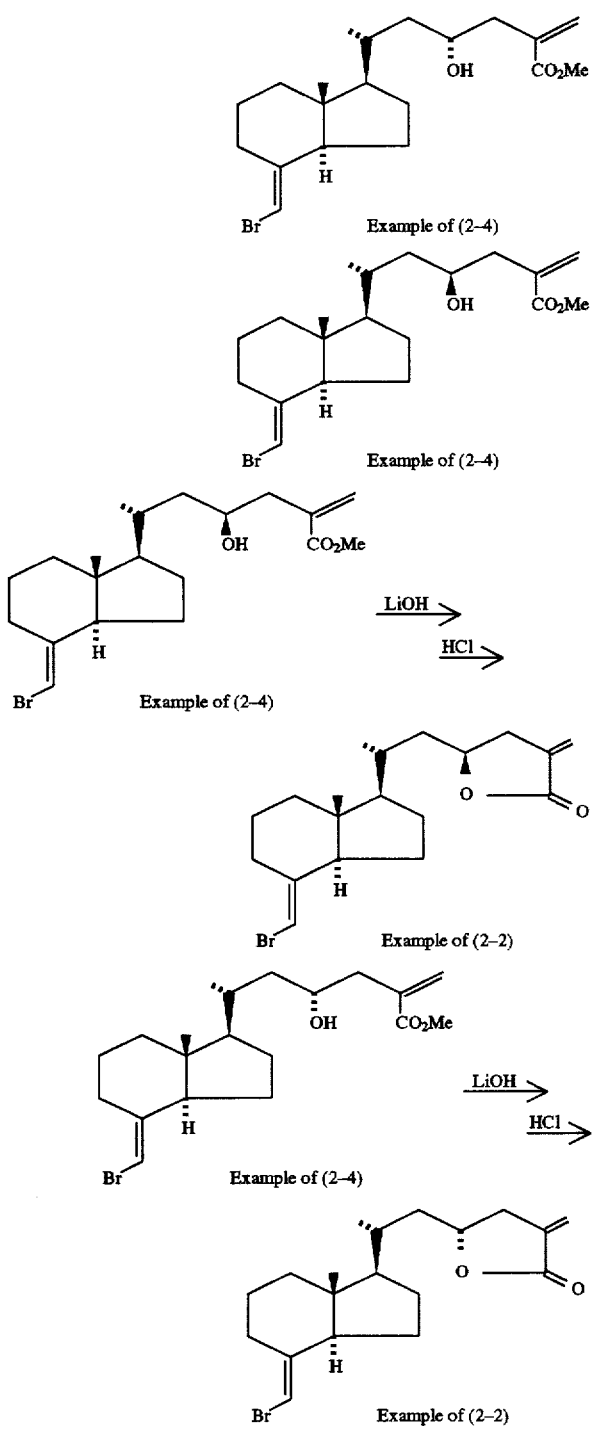

That is, the lactone compound represented by the above formula (2-2) is obtained by halomethylation of the lactone compound represented by the above formula (2-3). Further, the compound represented by the above formula (2-3) is obtained by deblocking, if necessary, and then oxidizing the lactone compound represented by the above formula (2-5). Further, the lactone compound represented by the above formula (2-5) may be synthesized from the heptanoic acid derivative represented by the above formula (2-6). On the other hand, the lactone compound represented by the above formula (2-2) may be derived from the heptanoic acid derivative represented by the above formula (2-4). Further, the heptanoic acid derivative represented by the above formula (2-4) may be synthesized from the compound represented by the above formula (2-7). These reactions will be shown more specifically in the Examples:

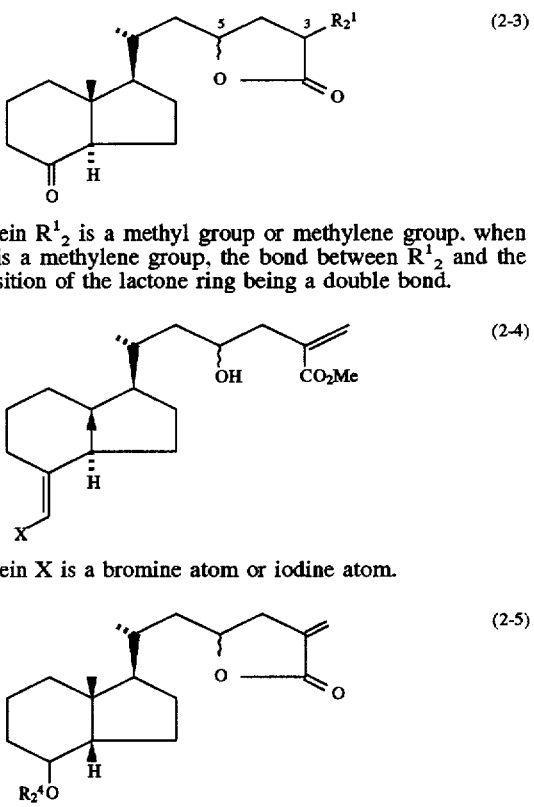

wherein $R^1_2$ is a methyl group or methylene group, when $R^1_2$ is a methylene group, the bond between $R^1_2$ and the 3-position of the lactone ring being a double bond.

wherein X is a bromine atom or iodine atom.

wherein $R^4_2$ is a hydrogen atom, tri($C_1$ to $C_7$ hydrocarbon) silyl group, $C_1$ to $C_7$ acyl group, or group forming an acetal group together with an oxygen atom of a hydroxyl group.

wherein $R^4_2$ is the same as defined above wherein X is a bromine atom or iodine atom, Y is a cyano group, formyl group, tosyl group, mesyl group, phenylsulfonyloxy group, tri($C_1$ to Chydrocarbon)silyl group, $C_1$ to $C_7$ acyl group, or hydroxyl group which may be blocked by an acetal group together with the oxygen atom of a hydroxyl group.

The present invention includes compounds represented by the above formulas (2-2), (2-3), (2-4), (2-5), (2-6), and (2-7)

serving as intermediates for the synthesis of the vitamin $D_3$ derivative represented by the above formula (2-1).

Here, when the $R^1$ of the lactone compound represented by the above formula (2-3) and (2-5) is a methyl group, the asymmetric center of the 3-position of the lactone ring is the (S) configuration and the asymmetric center of the 5-position may be either of the (R) configuration or (S) configuration. The derivative may also be any mixture thereof at any ratio.

Further, in the heptanoic acid derivative represented by the above formula (2-4) or (2-6), the asymmetric center of the 4-position may be either of the (R) configuration or (S) configuration. The derivative may also be a mixture of any ratio of the two.

Preferable specific examples of the compound represented by the above formula (2-2) according to the present invention are as follows:

1) (5S)-5-{(2R)-2-[(1R,7aR)-octahydro-4-bromomethylene-7a-methyl-1H-inden-1-yl]propyl}-3-methylene-dehydro-2(3H)-furanon 2) (5R)-5-{(2R)-2-[(1R,7aR)-octahydro-4-bromomethylene-7a-methyl-1H-inden-1-yl]propyl}-3-methylene-dehydro-2(3H)-furanon 3) (3S,5S)-5-{(2R)-2-[(1R,7aR)-octahydro-4-bromomethylene-7a-methyl-1H-inden-1-yl]propyl}-3-methyl-dehydro-2(3H)-furanon 4) (3S,5R)-5-{(2R)-2-[(1R,7aR)-octahydro-4-bromomethylene-7a-methyl-1H-inden-1-yl]propyl}-3-methyl-dehydro-2(3H)-furanon 5) (5S)-5-{(2R)-2-[(1R,7aR)-octahydro-4-iodomethylene-7a-methyl-1H-inden-1-yl]propyl}-3-methylene-dehydro-2(3H)-furanon 6) (5R)-5-{(2R)-2-[(1R,7aR)-octahydro-4-iodomethylene-7a-methyl-1H-inden-1-yl]propyl}-3-methylene-dehydro-2(3H)-furanon 7) (3S,5S)-5-{(2R)-2-[(1R,7aR)-octahydro-4-iodomethylene-7a-methyl-1H-inden-1-yl]propyl}-3-methyl-dehydro-2(3H)-furanon 8) (3S,5R)-5-{(2R)-2-[(1R,7aR)-octahydro-4-iodomethylene-7a-methyl-1H-inden-1-yl]propyl}-3-methyl-dehydro-2(3H)-furanon Preferable specific examples of the compound represented by the above formula (2-3) according to the present invention are as follows:

1) (5S)-5-{(2R)-2-[(1R,7aR)-octahydro-4-oxo-7a-methyl-1H-inden-1-yl]propyl}-3-methylene-dehydro-2(3H)-furanon 2) (5R)-5-{(2R)-2-[(1R,7aR)-octahydro-4-oxo-7a-methyl-1H-inden-1-yl]propyl}-3-methylene-dehydro-2(3H)-furanon 3) (3S,5S)-5-{(2R)-2-[(1R,7aR)-octahydro-4-oxo-7a-methyl-1H-inden-1-yl]propyl}-3-methyl-dehydro-2(3H)-furanon 4) (3S,5R)-5-{(2R)-2-[(1R,7aR)-octahydro-4-oxo-7a-methyl-1H-inden-1-yl]propyl}-3-methyl-dehydro-2(3H)-furanon Preferable specific examples of the compound represented by the above formula (2-4) according to the present invention are as follows:

1) (4S,6R)-6-[(1R,7aR)-octahydro-4-bromomethylene-7a-methyl-1H-inden-1-yl]-2-methoxycarbonyl-4-hydroxy-1-heptene 2) (4R,6R)-6-[(1R,7aR)-octahydro-4-bromomethylene-7a-methyl-1H-inden-1-yl]-2-methoxycarbonyl-4-hydroxy-1-heptene 3) (4S,6R)-6-[(1R,7aR)-octahydro-4-iodomethylene-7a-methyl-1H-inden-1-yl]-2-methoxycarbonyl-4-hydroxy-1-heptene 4) (4R,6R)-6-[(1R,7aR)-octahydro-4-iodomethylene-7a-methyl-1H-inden-1-yl]-2-methoxycarbonyl-4-hydroxy-1-heptene Preferable specific examples of the compound represented by the above formula (2-5) according to the present invention are as follows:

1) (5S)-5-{(2R)-2-[(1R,7aR)-octahydro-4-hydroxy-7a-methyl-1H-inden-1-yl]propyl}-3-methylene-dehydro-2(3H)-furanon 2) (5R)-5-{(2R)-2-[(1R,7aR)-octahydro-4-hydroxy-7a-methyl-1H-inden-1-yl]propyl}-3-methylene-dehydro-2(3H)-furanon 3) (3S,5S)-5-{(2R)-2-[(1R,7aR)-octahydro-4-hydroxy-7a-methyl-1H-inden-1-yl]propyl}-3-methyl-dehydro-2(3H)-furanon 4) (3S,5R)-5-{(2R)-2-[(1R,7aR)-octahydro-4-hydroxy-7a-methyl-1H-inden-1-yl]propyl}-3-methyl-dehydro-2(3H)-furanon 5) (5S)-5-{(2R)-2-[(1R,7aR)-octahydro-4-trimethylsilyloxy-7a-methyl-1H-inden-1-yl]propyl}-3-methylene-dehydro-2(3H)-furanon 6) (5R)-5-{(2R)-2-[(1R,7aR)-octahydro-4-trimethylsilyloxy-7a-methyl-1H-inden-1-yl]propyl}-3-methylene-dehydro-2(3H)-furanon 7) (3S,5S)-5-{(2R)-2-[(1R,7aR)-octahydro-4-rimethylsilyloxy-7a-methyl-1H-inden-1-yl]propyl}-3-methyl-dehydro-2(3H)-furanon 8) (3S,5R)-5-{(2R)-2-[(1R,7aR)-octahydro-4-trimethylsilyloxy-7a-methyl-1H-inden-1-yl]propyl}-3-methyl-dehydro-2(3H)-furanon 9) (5S)-5-{(2R)-2-[(1R,7aR)-octahydro-4-t-butyldimethylsilyloxy-7a-methyl-1H-inden-1-yl]propyl}-3-methylene-dehydro-2(3H)-furanon 10) (5R)-5-{(2R)-2-[(1R,7aR)-octahydro-4-t-butyldimethylsilyloxy-7a-methyl-1H-inden-1-yl]propyl}-3-methylene-dehydro-2(3H)-furanon 11) (3S,5S)-5-{(2R)-2-[(1R,7aR)-octahydro-4-t-butyldimethylsilyloxy-7a-methyl-1H-inden-1-yl]propyl}-3-methyl-dehydro-2(3H)-furanon 12) (3S,5R)-5-{(2R)-2-[(1R,7aR)-octahydro-4-t-butyldimethylsilyloxy-7a-methyl-1H-inden-1-yl]propyl}-3-methyl-dehydro-2(3H)-furanon Preferable specific examples of the compound represented by the above formula (2-6) according to the present invention are as follows:

1) (4S,6R)-6-[(1R,7aR)-octahydro-4-hydroxy-7a-methyl-1H-inden-1-yl]-2-methoxycarbonyl-4-hydroxy-1-heptene 2) (4R,6R)-6-[(1R,7aR)-octahydro-4-hydroxy-7a-methyl- 1H-inden-1-yl]-2-methoxycarbonyl-4-hydroxy-1-heptene 3) (4S,6R)-6-[(1R,7aR)-octahydro-4-trimethylsilyloxy-7a-methyl-1H-inden-1-yl]-2-methoxycarbonyl-4-hydroxy-1-heptene 4) (4R,6R)-6-[(1R,7aR)-octahydro-4-trimethylsilyloxy-7a-methyl-1H-inden-1-yl]-2-methoxycarbonyl-4-hydroxy-1-heptene 5) (4S,6R)-6-[(1R,7aR)-octahydro-4-t-butyldimethylsilyloxy-7a-methyl-1H-inden-1-yl]-2-methoxycarbonyl-4-hydroxy-1-heptene 6) (4R,6R)-6-[(1R,7aR)-octahydro-4-t-butyldimethylsilyloxy-7a-methyl-1H-inden-1-yl]-2-methoxycarbonyl-4-hydroxy-1-heptene Preferable specific examples of the compound represented by the above formula (2-7) according to the present invention are as follows:

1) (2R)-2-[(1R,7aR)-octahydro-4-bromomethylene-7a-methyl-1H-inden-1-yl]propylparatoluenes ulfonate 2) (3R)-3-[(1R,7aR)-octahydro-4-bromomethylene-7a-methyl-1H-inden-1-yl]butyronitrile 3) (3R)-3-[(1R,7aR)-octahydro-4-bromomethylene-7a-methyl-1H-inden-1-yl]butanal 4) (2R)-2-[(1R,7aR)-octahydro-4-iodomethylene-7a-methyl-1H-inden-1-yl]propylparatoluene-sulfonate 5) (3R)-3-[(1R,7aR)-octahydro-4-iodomethylene-7a-methyl-1H-inden-1-yl]butyronitrile 6) (3R)-3-[(1R,7aR)-octahydro-4-iodomethylene-7a-methyl-1H-inden-1-yl]butanal The vitamin $D_3$ derivative represented by the above formula (2-1) may be used as an agent for promoting bone growth. Further, the compounds represented by the above formulas (2-2), (2-3), (2-4), (2-5), (2-6), and (2-7) may be used as intermediates for the synthesis thereof.

That is, according to the third aspect of the present invention, there is provided a vitamin $D_3$ derivative represented by the following formula (3-1):

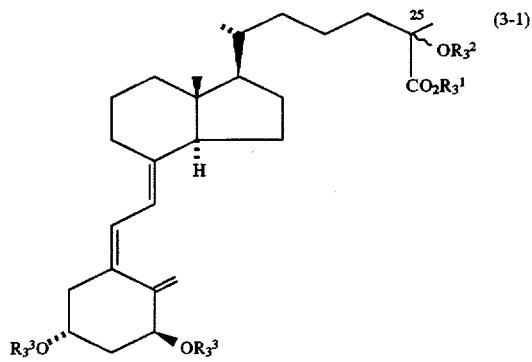

wherein $R^1_3$ is a hydrogen atom or $C_1$ to $C_3$ alkyl group $R^2_3$ is a hydrogen atom, or $R^1_3$ and $R^2_3$ together indicate a substitutable single methylene group $R^2_3$ is a hydrogen atom, tri($C_1$ to $C_7$ hydrocarbon)silyl group, $C_2$ to $C_8$ acyl group, or a group forming an acetal bond together with an oxygen atom of a hydroxyl group.

Here, when $R^1_3$ is a $C_1$ to $C_3$ alkyl group, specific examples are preferably methyl, ethyl, and propyl. Further, examples of the substituent, when $R^1_3$ and $R^2_3$ together represent a substitutable single methylene group, are preferably a t-butyl group, phenyl group, or methyl group. When $R^3_3$ is a tri($C_1$ to $C_7$ hydrocarbon)silyl group, a tri($C_1$ to C4 alkyl)silyl group such as a trimethylsilyl, triethylsilyl, or t-butyldimethylsilyl group or a phenyl($C_1$–$C_4$ alkyl)silyl group such as a t-butyldiphenylsilyl group are preferable.

Further, when $R^3_3$ is a $C_2$ to $C_8$ acyl group, an acetyl, propionyl, N-butyryl, pivaloyl, benzoyl, methoxycarbonyl, ethoxycarbonyl, or benzyloxycarbonyl group are preferable. Further, when $R^3_3$ is a group forming an acetal bond with an oxygen atom of a hydroxyl group, a methoxymethyl, 2-methoxy-ethoxymethyl, 2-methoxy-2-propyl, 2-tetrahydrofuranyl, or 2-tetrahydropyranyl group are preferable.

Here, the configuration of the 25-position of the vitamin $D_3$ derivative of the present invention may be either of the (R) configuration or (S) configuration. The derivative may also be any mixture thereof at any ratio of the two components. Specific examples of the vitamin $D_3$ derivative according to the third aspect of the present invention are given below:

1) 1α,25(R)-dihydroxyvitamin $D_3$-26-carboxylic acid 2) 1α,25(S)-dihydroxyvitamin $D_3$-26-carboxylic acid 3) 1α,25(R)-dihydroxyvitamin $D_3$-26-carboxylic acid methylester 4) 1α,25(S)-dihydroxyvitamin $D_3$-26-carboxylic acid methylester 5) 1α,25(R)-dihydroxyvitamin $D_3$-26-carboxylic acid ethylester 6) 1α,25(S)-dihydroxyvitamin $D_3$-26-carboxylic acid ethylester 7) 1α,25(R)-dihydroxyvitamin $D_3$-26-carboxylic acid methylester-1,3-bistrimethylsilylether 8) 1α,25(S)-dihydroxyvitamin $D_3$-26-carboxylic acid methylester-1,3-bistrimethylsilylether 9) 1α,25(R)-dihydroxyvitamin $D_3$-26-carboxylic acid ethylester-1,3-bistrimethylsilylether 10) 1α,25(S)-dihydroxyvitamin $D_3$-26-carboxylic acid ethylester-1,3-bistrimethylsilylether 11) 25,26,27-trinol-1α-hydroxy-24-[(2S,5R)-2-t-butyl-5-methyl-1,3-dioxolan-4-one-5-yl]-vitamin $D_3$ 12) 25,26,27-trinol-1α-hydroxy-24-[(2S,5R)-2-t-butyl-5-methyl-1,3-dioxolan-4-one-5-yl]-vitamin $D_3$-1,3-bistrimethylsilylether 13) 25,26,27-trinol-1α-hydroxy-24-[(2S,5R)-2-t-butyl-5-methyl-1,3-dioxolan-4-one-5-yl]-vitamin $D_3$-1,3-bis(t-butyldimethylsilylether)

Further, the present invention includes a production process of a vitamin $D_3$ derivative represented by the above formula (3-1).

That is, it provides a production process of a vitamin $D_3$ derivative represented by the above formula (3-1) characterized by reacting a heptanoic acid derivative represented by the following formula (3-2):

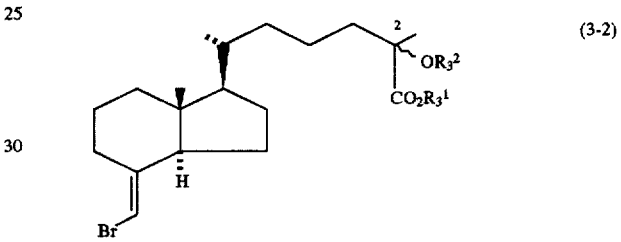

wherein $R^2_3$ and $R^3_3$ are the same as defined above with an enyne compound represented by the following formula (3-5):

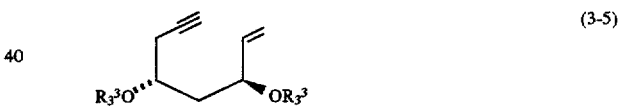

wherein $R^3_3$ is the same as defined above in the presence of a palladium catalyst.

In the production process of the vitamin $D_3$ derivative according to the present invention, the configuration of the asymmetric center of the 2-position of the starting material, that is, the heptanoic acid derivative represented by the above formula (3-2), may be either of the (R) configuration or (S) configuration. Further, the derivative may be any mixture of these stereo isomers at any ratio.

For example, when a heptanoic acid derivative represented by the above formula (3-2) where the asymmetric center of the 2-position is the (R) configuration is used, the configuration is preserved during the reaction and a vitamin $D_3$ derivative represented by the above formula (3-1) where the asymmetric center of the 25-position is the (R) configuration is obtained.

In the same way, when a heptanoic acid derivative represented by the above formula (3-2) where the asymmetric center of the 2-position is an (S) configuration is used, a vitamin $D_3$ derivative represented by the above formula (3-1) where the asymmetric center of the 25-position is the (R) configuration is obtained.

The vitamin $D_3$ derivative represented by the above formula (3-1) is produced by reacting the heptanoic acid derivative represented by the above formula (3-2) with the enyne compound represented by above formula (3-5) in the presence of a palladium catalyst. Here, as the palladium catalyst used, mention may be made for example of a zero-valent or bivalent organopalladium compound. Examples of such a palladium compound are tetrakis (triphenyl phosphine)palladium or a mixture of a tris (dibenzylidene-acetone palladium, tris (dibenzylideneacetone)palladium chloroform, palladium acetate, etc. with a phosphorus compound such as triphenylphosphine or tributylphosphine (molar ratio of 1:1 to 1:10). Among these, as the palladium catalyst, the combination of tris(dibenzyli-deneacetone)palladium and triphenylphosphine (1:1 to 1:10) or tris(dibenzylideneacetone) palladium chloroform and triphenylphosphine (1:1 to 1:10) is preferred.

Here, the heptanoic acid derivative represented by the above formula (3-2) and the enyne compound represented by the above formula (3-5) stoichiometrically react equimolarly, but it is desirable to use a slight excess of the more readily available compound. Further, the palladium catalyst is used in the range of 0.1 to 100 molar %, preferably 1 to 20 molar %, with respect to the heptanoic acid derivative represented by the above formula (3-2).

Examples of the reaction solvent used in this reaction are a hydrocarbon type solvent such as hexane or toluene, an ether type solvent such as ether, tetrahydrofuran, dioxane, or dimethoxyethane, a water soluble solvent such as N,N-dimethylformamide or acetonitrile, or any mixed solvents thereof. All of these are preferably used after sufficient deaeration.

As the reaction temperature, a range of from room temperature to the boiling point is used. The reaction time differs according to the reaction temperature, but usually it is preferable that the reaction be performed until one of the heptanoic acid derivative represented by the above formula (3-2) or enyne compound represented by the above formula (3-5) is consumed as determined using an analytical means such as thin layer chromatography.

Further, to trap the acids such as the hydrogen halides produced during the reaction, it is preferable to add a base such as, for example, triethylamine or diisopropylethylamine and cause a reaction. As the amount of the base, at least one equivalent of the heptanoic acid derivative represented by the above formula (3-2) is preferably used. It is also possible to use together as a solvent. Therefore, the vitamin $D_3$ derivative represented by the above formula (3-1) is produced in the reaction system, but it is further possible to effect a deblocking reaction, if necessary.

As the method of the deblocking reaction, it is possible to use a known method in the case of deblocking, for example, the silyl groups (for example, Calveley, M. J., Tetrahedron, 20, 4609 to 4619, 1987). Examples of the deblocking agent in this case are tetrabutylammonium fluoride and pyridinium-p-toluene sulfonate.

An example of the synthesis method of a heptanoic acid derivative represented by the above formula (3-2) used as a starting material in the process of the present invention is shown in the following scheme. The same applies when $R^2_3$ and $R^3_3$ are other groups.

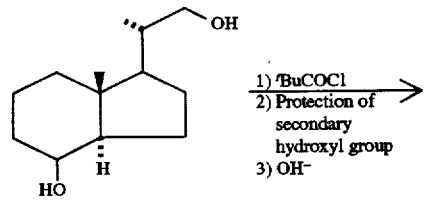

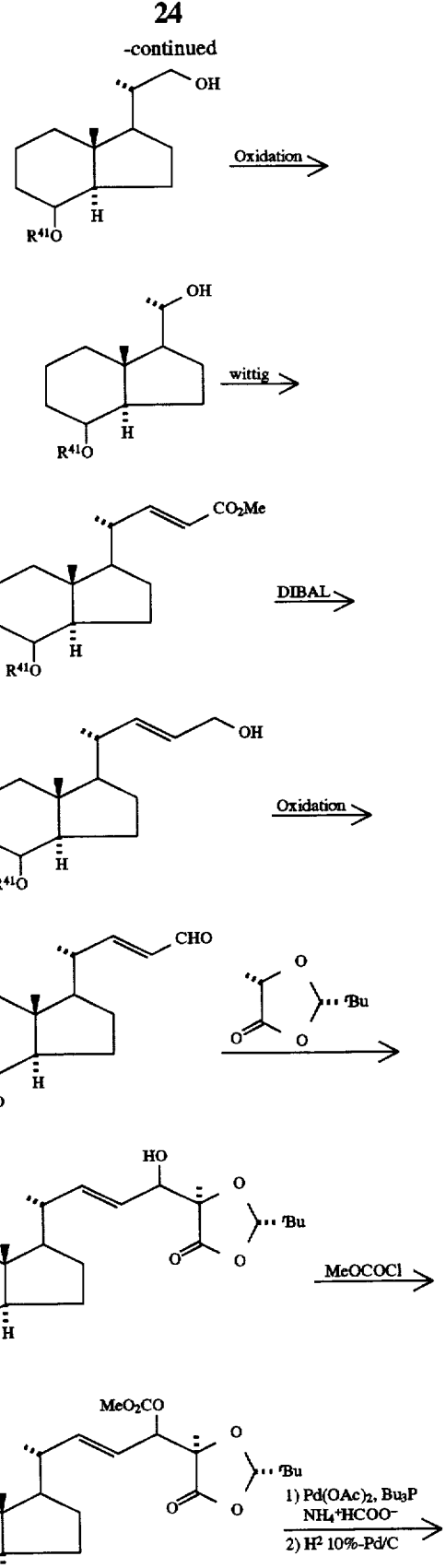

-continued

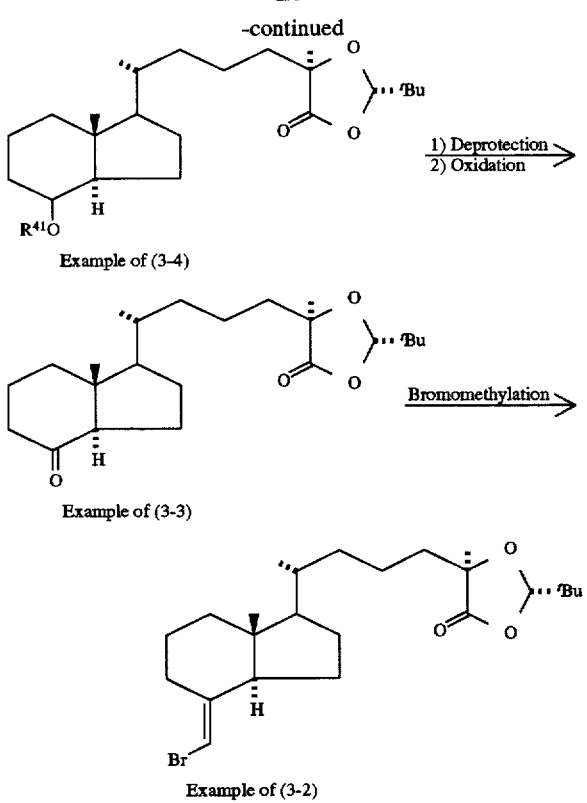

Example of (3-4)

Example of (3-3)

Example of (3-2)

wherein, in the above scheme, $R^{41}$ is a hydrogen atom, tri($C_1$ to $C_7$ hydrocarbon)silyl group, or a group forming an acetal bond with an oxygen atom of a hydroxyl group.

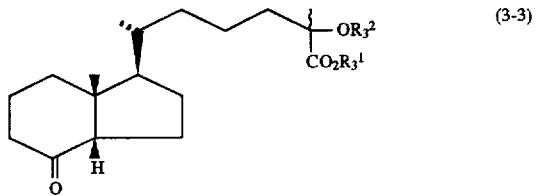
(3-3)

wherein, $R^1_3$ is a hydrogen atom or $C_1$ to $C_3$ alkyl group, $R^2_3$ is a hydrogen atom, or $R^1_3$ and $R^2_3$ together represent a substitutable single methylene group (examples of the substituent at this time are a $C_1$ to $C_6$ alkyl group such as methyl, t-butyl, or phenyl).

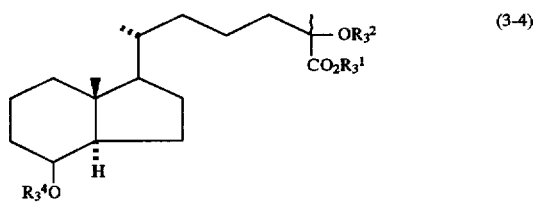
(3-4)

wherein, $R^1_3$ and $R^2_3$ are the same as defined above, and $R^4_3$ is a hydrogen atom, tri($C_1$ to $C_7$ hydrocarbon)silyl group, $C_1$ to $C_7$ acyl group, or represent an acetal group together with the oxygen atom of the hydroxyl group.

That is, the heptanoic acid derivative represented by the above formula (3-2) is obtained by bromomethylation of the heptanoic acid derivative represented by the above formula (3-3). Further, the heptanoic acid derivative represented by the above formula (3-3) is obtained by deprotecting the heptanoic acid derivative represented by the above (3-4) when necessary. Specific examples of these reactions are shown in the Examples. Here, the configuration of the 2-position of the heptanoic acid derivatives represented by the above formula (3-2), (3-3), or (3-4) may be either of the (R) configuration or (S) configuration. The derivative may also be any mixture thereof at any ratio.

The present invention includes intermediates for synthesis of the vitamin $D_3$ derivative according to the present invention represented by the above formulas (3-2), (3-3), or (3-4).

Preferable examples of the heptanoic acid derivative represented by the above formula (3-2) of the present invention are as follows:

1) (2S,5R)-5-{(4R)-4-[(1R,7aR)(4E)-octahydro-4-bromomethylene-7a-methyl-1H-inden-1-yl]pentyl}-2-t-butyl-5-methyl-1,3-dioxolan-4-one 2) (2R,5S)-5-{(4R)-4-[(1R,7aR)(4E)-octahydro-4-bromomethylene-7a-methyl-1H-inden-1-yl]pentyl}-2-t-butyl-5-methyl-1,3-dioxolan-4-one 3) (2S,5R)-5-{(4R)-4-[(1R,7aR)(4E)-octahydro-4-bromomethylene-7a-methyl-1H-inden-1-yl]pentyl}-2-phenyl-5-methyl-1,3-dioxolan-4-one 4) (2R,6R)-6-{(1R,7aR)(4E)-octahydro-4-bromomethylene-7a-methyl-1H-inden-1-yl}-2-hydroxy-2-methylheptanoic acid 5) (2S,6R)-6-{(1R,7aR)(4E)-octahydro-4-bromomethylene-7a-methyl-1H-inden-1-yl}-2-hydroxy-2-methylheptanoic acid 6) (2R,6R)-6-{(1R,7aR)(4E)-octahydro-4-bromomethylene-7a-methyl-1H-inden-1-yl}-2-hydroxy-2-methylheptanoic acid methylester 7) (2S,6R)-6-{(1R,7aR)(4E)-octahydro-4-bromomethylene-7a-methyl-1H-inden-1-yl}-2-hydroxy-2-methylheptanoic acid ethylester 8) (2R,6R)-6-{(1R,7aR)(4E)-octahydro-4-bromomethylene-7a-methyl-1H-inden-1-yl}-2-trimethylsilyloxy-2-methylheptanoic acid methylester 9) (2R,6R)-6-{(1R,7aR)(4E)-octahydro-4-bromomethylene-7a-methyl-1H-inden-1-yl}-2-t-butyldimethylsilyloxy-2-methylheptanoic acid methylester 10) (2R,6R)-6-{(1R,7aR)(4E)-octahydro-4-bromomethylene-7a-methyl-1H-inden-1-yl}-2-acetoxy-2-methylheptanoic acid methylester 11) (2R,6R)-6-{(1R,7aR)(4E)-octahydro-4-bromomethylene-7a-methyl-1H-inden-1-yl}-2-methoxymethyloxy-2-methylheptanoic acid methylester Further, preferable examples represented by the heptanoic acid derivative of the above (3-3) according to the present invention are as follows:

1) (2R,5S)-5-{(4R)-4-[(1R,7aR)-octahydro-4-oxo-7a-methyl-1H-inden-1-yl]pentyl}-2-t-butyl-5-methyl-1,3-dioxolan-4-one 2) (2R,5S)-5-{(4R)-4-[(1R,7aR)-octahydro-4-oxo-7a-methyl-1H-inden-1-yl]pentyl}-2-t-butyl-5-methyl-1,3-dioxolan-4-one 3) (2S,5R)-5-{(4R)-4-[(1R,7aR)-octahydro-4-oxo-7a-methyl-1H-inden-1-yl]pentyl}-2-phenyl-5-methyl-1,3-dioxolan-4-one 4) (2R,6R)-6-{(1R,7aR)-octahydro-4-oxo-7a-methyl-1H-inden-1-yl}-2-hydroxy-2-methylheptanoic acid 5(2S,6R)-6-{(1R,7aR)-octahydro-4-oxo-7a-methyl-1H-inden-1-yl}-2-hydroxy-2-methylheptanoic acid 6) (2R,6R)-6-{(1R,7aR)-octahydro-4-oxo-7a-methyl-1H-inden-1-yl}-2-hydroxy-2-methylheptanoic acid methylester 7(2S,6R)-6-{(1R,7aR)-octahydro-4-oxo-7a-methyl-1H-inden-1-yl}-2-hydroxy-2-methylheptanoic acid ethylester 8) (2R,6R)-6-{(1R,7aR)-octahydro-4-oxo-7a-methyl-1H-inden-1-yl}-2-trimethylsilyloxy-2-methylheptanoic acid methylester 9) (2R,6R)-6-{(1R,7aR)-octahydro-4-oxo-7a-methyl-1H-inden-1-yl}-2-t-butyldimethylsilyloxy-2methylheptanoic acid methylester 10) (2R,6R)-6-{(1R,7aR)-octahydro-4-oxo-7a-methyl-1H-inden-1-yl}-2-acetoxy-2-methylheptanoic acid methylester 11) (2R,6R)-6-{(1R,7aR)-octahydro-4-oxo-7a-methyl-1H-inden-1-yl}-2-methoxymethyloxy-2-methylheptanoic acid methylester Further, preferable examples of the heptanoic acid derivative represented by the above (3-4) according to the present invention are as follows:

1) (2S,5R)-5-{(4R)-4-[(1R,7aR)-octahydro-4-hydroxy-7a-methyl-1H-inden-1-yl]pentyl}-2-t-butyl-5-methyl-1,3-dioxolan-4-one 2) (2R,5S)-5-{(4R)-4-[(1R,7aR)-octahydro-4-hydroxy-7a-methyl-1H-inden-1-yl]pentyl}-2-t-butyl-5-methyl-1,3-dioxolan-4-one 3) (2S,5R)-5-{(4R)-4-[(1R,7aR)-octahydro-4-trimethylsilyloxy-7a-methyl-1H-inden-1-yl]pentyl}-2-phenyl-5-methyl-1,3-dioxolan-4-one 4) (2S,5R)-5-{(4R)-4-[(1R,7aR)-octahydro-4-acetoxy-7a-methyl-1H-inden-1-yl]pentyl}-2-phenyl-5-methyl-1,3-dioxolan-4-one 5(2S,5R)-5-{(4R)-4-[(1R,7aR)-octahydro-4-benzyloxy-7a-methyl-1H-inden-1-yl]pentyl}-2-phenyl-5-methyl-1,3-dioxolan-4-one 6) (2S,5R)-5-{(4R)-4-[(1R,7aR)-octahydro-4-methoxymethyloxy-7a-methyl-1H-inden-1-yl]pentyl}-2-phenyl-5-methyl-1,3-dioxolan-4-one 7) (2R,6R)-6-{(1R,7aR)-octahydro-4-hydroxy-7a-methyl-1H-inden-1-yl}-2-hydroxy-2-methylheptanoic acid 8) (2S,6R)-6-{(1R,7aR)-octahydro-4-hydroxy-7a-methyl-1H-inden-1-yl}-2-hydroxy-2-methylheptanoic acid 9) (2R,6R)-6-{(1R,7aR)-octahydro-4-trimethylsilyloxy-7a-methyl-1H-inden-1-yl}-2-hydroxy-2-methylheptanoic acid 10) (2S,6R)-6-{(1R,7aR)-octahydro-4-trimethylsilyloxy-7a-methyl-1H-inden-1-yl}-2-hydroxy-2-methylheptanoic acid 11) (2R,6R)-6-{(1R,7aR)-octahydro-4-acetoxy-7a-methyl-1H-inden-1-yl}-2-hydroxy-2-methylheptanoic acid 12) (2R,6R)-6-{(1R,7aR)-octahydro-4-trimethylsilyloxy-7a-methyl-1H-inden-1-yl}-2-hydroxy-2-methylheptanoic acid methylester 13) (2R,6R)-6-{(1R,7aR)-octahydro-4-acetoxy-7a-methyl-1H-inden-1-yl}-2-hydroxy-2-methylheptanoic acid methylester 14) (2R,6R)-6-{(1R,7aR)-octahydro-4-trimethylsilyloxy-7a-methyl-1H-inden-1-yl}-2-hydroxy-2-methylheptanoic acid ethylester 15) (2R,6R)-6-{(1R,7aR)-octahydro-4-hydroxy-7a-methyl-1H-inden-1-yl}-2-trimethylsilyloxy-2-methylheptanoic acid methylester 16) (2R,6R)-6-{(1R,7aR)-octahydro-4-acetoxy-7a-methyl-1H-inden-1-yl}-2-trimethylsilyloxy-2-methylheptanoic acid methylester 17) (2R,6R)-6-{(1R,7aR)-octahydro-4-trimethylsilyloxy-7a-methyl-1H-inden-1-yl}-2-acetoxy-2-methylheptanoic acid methylester 18) (2R, 6R)-6-{(1R, 7aR)-octahydro-4-trimethylsilyloxy-7a-methyl-1H-inden-1-yl}-2-methoxymethyloxy-2-methylheptanoic acid methylester The vitamin $D_3$ derivative represented by the above formula (3-1) may be used as an agent for promoting bone formation. Further, the heptanoic acid derivatives represented by the above formulas (3-2), (3-3), and (3-4) may be used as intermediates for the synthesis thereof.

According to the present invention, as a manufacturing intermediate for the vitamin $D_3$ derivative according to the present invention, there is the exomethylene derivative represented by the following formula (4-1):

$$\text{(4-1)}$$

wherein $R^1_4$ is a hydrogen atom, tri($C_1$ to $C_7$ hydrocarbon) silyl group, $C_2$ to $C_7$ acyl group, or group forming an acetal bond with an oxygen atom of a hydroxyl group, and $X_4$ is a bromine atom or iodine atom.

In the present invention, in the compound represented by the above formula (4-1), the configurations of the asymmetric centers of the C-3 position and C-5 position of the 2(3H)-furanon ring may respectively be either of the (R) configuration or (S) configuration. Further, the present invention includes mixtures of these four types of stereo isomers at any ratio. Among these, those where the asymmetric center of the C-3 position is the (R) configuration and the asymmetric center of the C-5 position is the (R) configuration and ones where the asymmetric center of the C-3 position is the (R) configuration and the asymmetric center of the C-5 position is the (S) configuration are preferred. Further, the configuration of the carbon-carbon double bond of the halomethylene portion is the (E) configuration.

Specific examples of the exomethylene derivative of the above formula (4-1) of the present invention are given below:

1) (3R,5R)-5-{(3R)-3-[(1R,7aR)-octahydro-4-bromomethylene-7a-methyl-1H-inden-1-yl]-butyl}-3-methyl-3-hydroxy-2(3H)-furanon 2) (3R,5S)-5-{(3R)-3-[(1R, 7aR)-octahydro-4-bromomethylene-7a-methyl-1H-inden-1-yl]-butyl}-3-methyl-3-hydroxy-2(3H)-furanon 3) (3S,5R)-5-{(3R)-3-[(1R,7aR)-octahydro-4-bromomethylene-7a-methyl-1H-inden-1-yl]-butyl}-3-methyl-3-hydroxy-2(3H)-furanon 4) (3S,5S)-5-{(3R)-3-[(1R,7aR)-octahydro-4-bromomethylene-7a-methyl-1H-inden-1-yl]-butyl}-3-methyl-3-hydroxy-2(3H)-furanon 5) (3R,5R)-5-{(3R)-3-[(1R,7aR)-octahydro-4-bromomethylene-7a-methyl-1H-inden-1-yl]-butyl}-3-methyl-3-trimethylsilyloxy-2(3H)-furanon 6) (3R,5S)-5-{(3R)-3-[(1R,7aR)-octahydro-4-bromomethylene-7a-methyl-1H-inden-1-yl]-butyl}-3-methyl-3-trimethylsilyloxy-2(3H)-furanon 7) (3S,5R)-5-{(3R)-3-[(1R,7aR)-octahydro-4-bromomethylene-7a-methyl-1H-inden-1-yl]-butyl}-3-methyl-3-trimethylsilyloxy-2(3H)-furanon 8) (3S,5S)-5-{(3R)-3-[(1R,7aR)-octahydro-4-bromomethylene-7a-methyl-1H-inden-1-yl]-butyl}-3-methyl-3-trimethylsilyloxy-2(3H)-furanon 9) (3R,5R)-5-{(3R)-3-[(1R,7aR)-octahydro-4-bromomethylene-7a-methyl-1H-inden-1-yl]-butyl}-3-methyl-3-(t-butyldimethylsilyloxy)-2(3H)-furanon 10) (3R,5S)-5-{(3R)-3-[(1R,7aR)-octahydro-4-bromomethylene-7a-methyl-1H-inden-1-yl]-butyl}-3-methyl-3-(t-butyldimethylsilyloxy)-2(3H)-furanon 11) (3S,5R)-5-{(3R)-3-[(1R,7aR)-octahydro-4-bromomethylene-7a-methyl-1H-inden-1-yl]-butyl}-3-methyl-3-(t-butyldimethylsilyloxy)-2(3H)-furanon 12) (3S,5S)-5-{(3R)-3-[(1R,7aR)-octahydro-4-bromomethylene-7a-methyl-1H-inden-1-yl]-butyl}-3-methyl-3-(t-butyldimethylsilyloxy)-2(3H)-furanon 13) (3R,5R)-5-{(3R)-3-[(1R,7aR)-octahydro-4-bromomethylene-7a-methyl-1H-inden-1-yl]-butyl}-3-methyl-3-acetoxy-2(3H)-furanon 14) (3R,5S)-5-{(3R)-3-[(1R,7aR)-octahydro-4-bromomethylene-7a-methyl-1H-inden-1-yl]-butyl}-3-methyl-3-acetoxy-2(3H)-furanon 15) (3S,5R)-5-{(3R)-3-[(1R,7aR)-octahydro-4-bromomethylene-7a-methyl-1H-inden-1-yl]-butyl}-3-methyl-3-acetoxy-2(3H)-furanon 16) (3S,5S)-5-{(3R)-3-[(1R,7aR)-octahydro-4-bromomethylene-7a-methyl-1H-inden-1-yl]-butyl}-3-methyl-3-acetoxy-2(3H)-furanon 17) (3R,5R)-5-{(3R)-3-[(1R,7aR)-octahydro-4-bromomethylene-7a-methyl-1H-inden-1-yl]-butyl}-3-methyl-3-ethoxycarbonyloxy-2(3H)-furanon 18) (3R,5S)-5-{(3R)-3-[(1R,7aR)-octahydro-4-bromomethylene-7a-methyl-1H-inden-1-yl]-butyl}-3-methyl-3-ethoxycarbonyloxy-2(3H)-furanon 19) (3S,5R)-5-{(3R)-3-[(1R,7aR)-octahydro-4-bromomethylene-7a-methyl-1H-inden-1-yl]-butyl}-3-methYl-3-ethoxycarbonyloxy-2(3H)-furanon 20) (3S,5S)-5-{(3R)-3-[(1R,7aR)-octahydro-4-bromomethylene-7a-methyl-1H-inden-1-yl]-butyl}-3-methyl-3-ethoxycarbonyloxy-2(3H)-furanon 21) (3R,5R)-5-{(3R)-3-[(1R,7aR)-octahydro-4-bromomethylene-7a-methyl-1H-inden-1-yl]-butyl}-3-methyl-3-methoxymethyloxy-2(3H)-furanon 22) (3R,5S)-5-{(3R)-3-[(1R,7aR)-octahydro-4-bromomethylene-7a-methyl-1H-inden-1-yl]-butyl}-3-methyl-3-methoxymethyloxy-2(3H)-furanon 23) (3S,5R)-5-{(3R)-3-[(1R,7aR)-octahydro-4-bromomethylene-7a-methyl-1H-inden-1-yl]-butyl}-3-methyl-3-methoxymethyloxy-2(3H)-furanon 24) (3S,5S)-5-{(3R)-3-[(1R,7aR)-octahydro-4-bromomethylene-7a-methyl-1H-inden-1-yl]-butyl}-3-methyl-3-methoxymethyloxy-2(3H)-furanon 25) (3R,5R)-5-{(3R)-3-[(1R,7aR)-octahydro-4-bromomethylene-7a-methyl-1H-inden-1-yl]-butyl}-3-methyl-3-tetrahydropyranyloxy-2(3H)-furanon 26) (3R,5S)-5-{(3R)-3-[(1R,7aR)-octahydro-4-bromomethylene-7a-methyl-1H-inden-1-yl]-butyl}-3-methyl-3-tetrahydropyranyloxy-2(3H)-furanon 27) (3S,5R)-5-{(3R)-3-[(1R,7aR)-octahydro-4-bromomethylene-7a-methyl-1H-inden-1-yl]-butyl}-3-methyl-3-tetrahydropyranyloxy-2(3H)-furanon 28) (3S,5S)-5-{(3R)-3-[(1R,7aR)-octahydro-4-bromomethylene-7a-methyl-1H-inden-1-yl]-butyl}-3-methyl-3-tetrahydropyranyloxy-2(3H)-furanon 29) (3R,5R)-5-{(3R)-3-[(1R,7aR)-octahydro-4-iodomethylene-7a-methyl-1H-inden-1-yl]-butyl}-3-methyl-3-hydroxy-2(3H)-furanon 30) (3R,5S)-5-{(3R)-3-[(1R,7aR)-octahydro-4-iodomethylene-7a-methyl-1H-inden-1-yl]-butyl}-3-methyl-3-hydroxy-2(3H)-furanon 31) (3S,5R)-5-{(3R)-3-[(1R,7aR)-octahydro-4-iodomethylene-7a-methyl-1H-inden-1-yl]-butyl}-3-methyl-3 -hydroxy-2(3H)-furanon 32) (3S,5S)-5-{(3R)-3-[(1R,7aR)-octahydro-4-iodomethylene-7a-methyl-1H-inden-1-yl]-butyl}-3-methyl-3-hydroxy-2(3H)-furanon 33) (3R,5R)-5-{(3R)-3-[(1R,7aR)-octahydro-4-iodomethylene-7a-methyl-1H-inden-1-yl]-butyl}-3-methyl-3-trimethylsilyloxy-2(3H)-furanon 34) (3R,5S)-5-{(3R)-3-[(1R,7aR)-octahydro-4-iodomethylene-7a-methyl-1H-inden-1-yl]-butyl}-3-methyl-3-trimethylsilyloxy-2(3H)-furanon 35) (3S,5R)-5-{(3R)-3-[(1R,7aR)-octahydro-4-iodomethylene-7a-methyl-1H-inden-1-yl]-butyl}-3-methyl-3-trimethylsilyloxy-2(3H)-furanon 36) (3S,5S)-5-{(3R)-3-[(1R,7aR)-octahydro-4-iodomethylene-7a-methyl-1H-inden-1-yl]-butyl}-3-methyl-3-trimethylsilyloxy-2(3H)-furanon Further, the present invention provides a process for producing the exomethylene derivative represented by the above formula (4-1).

That is, it provides a process causing a reaction of a 2(3H)-furanon derivative represented by the following formula (4-2)

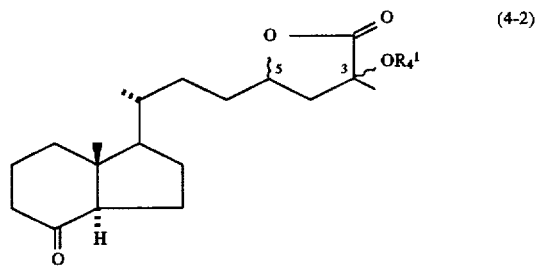

wherein $R^1_4$ is a hydrogen atom, tri($C_1$ to $C_7$ hydrocarbon) silyl group, $C_2$ to $C_7$ acyl group, or group forming an acetal bond together with an oxygen atom of a hydroxyl group with a halogenated methylenetriphenylphosphonium halide in the presence of a base so as to produce an exomethylene derivative represented by the following formula (4-1):

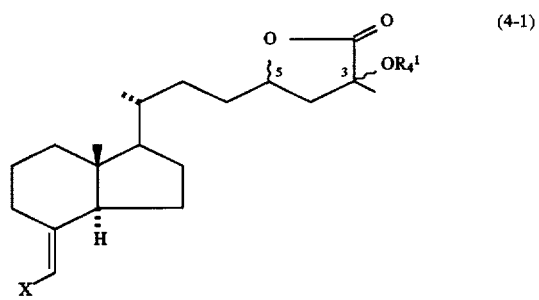

wherein, $R^1_4$ and X are the same as defined above.

In the production process of an exomethylene derivative according to the present invention, the configurations of the asymmetric center of the C-3 position and C-5 position of the 2(3)H-furanon ring of the starting material, that is, the 2(3)H-furanon derivative represented by the above formula (4-2), may respectively be either of the (R) configuration or (S) configuration. Further, the derivative may be any mixture of these stereo isomers at any ratio.

For example, when a 2(3H)-furanon derivative of the above formula (4-2) wherein the asymmetric center of the C-3 position of the 2(3H)-furanon ring is the (R) configuration and the asymmetric center of the C-5 position is the (R) configuration, the configuration of these portions are preserved during the reaction and an exomethylene derivative represented by the above formula (4-1) wherein the asymmetric center of the C-3 position of the 2(3H)-furanon ring is the (R) configuration and the asymmetric center of the C-5 position is the (R) configuration is obtained.

In the same way, when a 2(3H)-furanon derivative represented by the above formula (4-2) where the asymmetric center of the C-3 position of the (3H)-furanon ring is the (R) configuration and the asymmetric center of the C-5 position is the (S) configuration is used, an exomethylene derivative represented by the above formula (4-1) where the asymmetric center of the C-3 position of the 2(3H)-furanon ring is the (R) configuration and the asymmetric center of the C-5 position is the (S) configuration is obtained.

Here, when $R^1_4$ is a tri($C_1$ to $C_7$ hydrocarbon)silyl group, specific examples are preferably a tri($C_1$ to $C_4$ alkyl)silyl group such as a trimethylsilyl, triethylsilyl, or t-butyldimethylsilyl group or a phenyl($C_1$ to $C_4$ alkyl)silyl group such as a t-butyldiphenylsilyl group.

Further, when $R^1_4$ is a $C_2$ to $C_7$ acyl group, specific examples are preferably an acetyl, propionyl, N-butyryl, pivaloyl, benzoyl, methoxycarbonyl, ethoxycarbonyl, benzyloxycarbonyl group. Further, when $R^1_4$ is a group forming an acetal bond together with an oxygen atom of a hydroxyl group, specific examples are preferably a methoxymethyl, (2-methoxyethoxy)-methyl, 2-methoxy-2-propyl, 2-tetrahydrofuranyl, or 2-tetrahydropyranyl group.

The exomethylene derivative represented by the above formula (4-1) is produced by reacting the 2(3H)-furanon derivative represented by the above formula (4-2) with a halogenated methylenetriphenylphosphonium halide in the presence of a base. Here, as the halogenated methylenetriphenylphosphonium halide which is used, bromomethylenetriphenylphosphonium bromide etc. are preferred. Further, as the base used, lithium diisopropylamide, lithium bistrimethylsilyl-amide, sodium bistrimethylsilylamide, etc. may be exemplified as preferable examples. Further, as the amount of the base used, 1 to 10 times the amount of the 2(3H)-furanon derivative is preferable.

Here, as the amount of the halogenated methylenetriphenylphosphonium halide for reacting with the 2(3H)-furanon derivative of the above formula (4-2), 1 to 10 times the amount of the 2(3H)-furanon derivative is preferably used.

Examples of the reaction solvent used in this reaction are an ether type solvent such as diethyl ether, tetrahydrofuran, and dimethoxyethane. As the reaction temperature, a range of from $-60°$ C. to room temperature is used. The reaction time differs according to the reaction temperature, but usually that the reaction be continued until the 2(3H)-furanon derivative of the above formula (4-2) is consumed as determined using an analytical means such as thin layer chromatography.

The compound represented by the above formula (4-2) used as a starting material in the present invention may be synthesized, for example, in accordance with the following scheme:

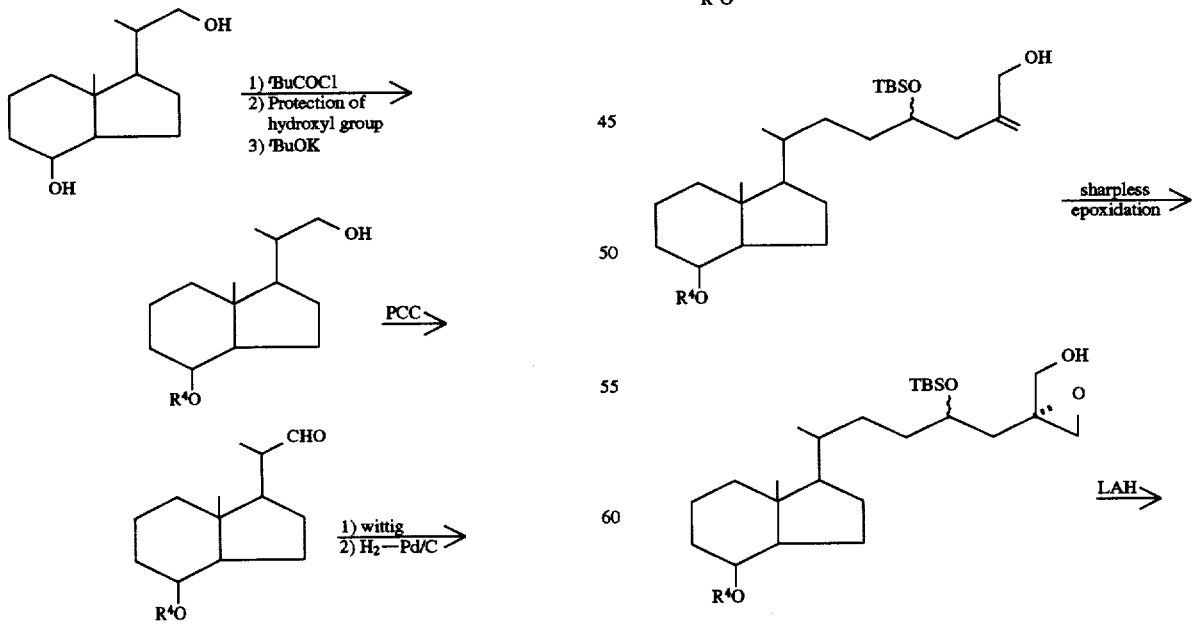

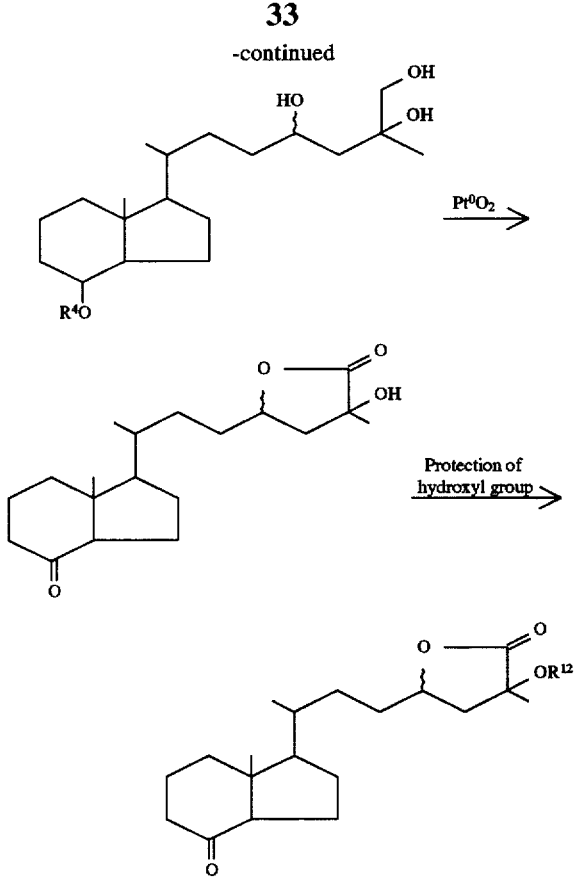

wherein, in the above scheme, $R^4$ and $R^{12}$ are a hydrogen atom, tri($C_1$ to $C_7$ hydrocarbon)silyl group, $C_2$ to $C_7$ acyl group, or group forming an acetal bond with an oxygen atom of a hydroxyl group.

Specific examples of the 2(3H)-furanon derivative represented by the chemical formula (4-2) preferred in the present invention are as follows:

1) (3R,5R)-5-{(3R)-3-[(1R,7aR)-octahydro-4-oxo-7a-methyl-1H-inden-1-yl]-butyl}-3-methyl-3-hydroxy-2(3H)-furanon 2) (3R,5S)-5-{(3R)-3-[(1R,7aR)-octahydro-4-oxo-7a-methyl-1H-inden-1-yl]-butyl}-3-methyl-3-hydroxy-2(3H)-furanon 3) (3S,5R)-5-{(3R)-3-[(1R,7aR)-octahydro-4-oxo-7a-methyl-1H-inden-1-yl]-butyl}-3-methyl-3-hydroxy-2(3H)-furanon 4) (3S,5S)-5-{(3R)-3-[(1R,7aR)-octahydro-4-oxo-7a-methyl-1H-inden-1-yl]-butyl}-3-methyl-3-hydroxy-2(3H)-furanon 5) (3R,5R)-5-{(3R)-3-[(1R,7aR)-octahydro-4-oxo-7a-methyl-1H-inden-1-yl]-butyl}-3-methyl-3-trimethylsilyloxy-2(3H)-furanon 6) (3R,5S)-5-{(3R)-3-[(1R,7aR)-octahydro-4-oxo-7a-methyl-1H-inden-1-yl]-butyl}-3-methyl-3-trimethylsilyloxy-2(3H)-furanon 7) (3S,5R)-5-{(3R)-3-[(1R,7aR)-octahydro-4-oxo-7a-methyl-1H-inden-1-yl]-butyl}-3-methyl-3-trimethylsilyloxy-2(3H)-furanon 8) (3S,5S)-5-{(3R)-3-[(1R,7aR)-octahydro-4-oxo-7a-methyl-1H-inden-1-yl]-butyl}-3-methyl-3-trimethylsilyloxy-2(3H)-furanon 9) (3R,5R)-5-{(3R)-3-[(1R,7aR)-octahydro-4-oxo-7a-methyl-1H-inden-1-yl]-butyl}-3-methyl-3-(t-butyl-dimethylsilyloxy)-2(3H)-furanon 10) (3R,5S)-5-{(3R)-3-[(1R,7aR)-octahydro-4-oxo-7a-methyl-1H-inden-1-yl]-butyl}-3-methyl-3-(t-butyl-dimethylsilyloxy)-2(3H)-furanon 11) (3S,5R)-5-{(3R)-3-[(1R,7aR)-octahydro-4-oxo-7a-methyl-1H-inden-1-yl]-butyl}-3-methyl-3-(t-butyl-dimethylsilyloxy)-2(3H)-furanon 12) (3S,5S)-5-{(3R)-3-[(1R,7aR)-octahydro-4-oxo-7a-methyl-1H-inden-1-yl]-butyl}-3-methyl-3-(t-butyl-dimethylsilyloxy)-2(3H)-furanon 13) (3R,5R)-5-{(3R)-3-[(1R,7aR)-octahydro-4-oxo-7a-methyl-1H-inden-1-yl]-butyl}-3-methyl-3-acetoxy-2(3H)-furanon 14) (3S,5S)-5-{(3R)-3-[(1R,7aR)-octahydro-4-oxo-7a-methyl-1H-inden-1-yl]-butyl}-3-methyl-3-acetoxy-2(3H)-furanon 15) (3S,5R)-5-{(3R)-3-[(1R,7aR)-octahydro-4-oxo-7a-methyl-1H-inden-1-yl]-butyl}-3-methyl-3-acetoxy-2(3H)-furanon 16) (3S,5S)-5-{(3R)-3-[(1R,7aR)-octahydro-4-oxo-7a-methyl-1H-inden-1-yl]-butyl}-3-methyl-3-acetoxy-2(3H)-furanon 17) (3R,5R)-5-{(3R)-3-[(1R,7aR)-octahydro-4-oxo-7a-methyl-1H-inden-1-yl]-butyl}-3-methyl-3-ethoxycarbonyloxy-2(3H)-furanon 18) (3R,5S)-5-{(3R)-3-[(1R,7aR)-octahydro-4-oxo-7a-methyl-1H-inden-1-yl]-butyl}-3-methyl-3-ethoxycarbonyloxy-2(3H)-furanon 19) (3S,5R)-5-{(3R)-3-[(1R,7aR)-octahydro-4-oxo-7a-methyl-1H-inden-1-yl]-butyl}-3-methyl-3-ethoxycarbonyloxy-2(3H)-furanon 20) (3S,5S)-5-{(3R)-3-[(1R,7aR)-octahydro-4-oxo-7a-methyl-1H-inden-1-yl]-butyl}-3-methyl-3-ethoxycarbonyloxy-2(3H)-furanon 21) (3R,5R)-5-{(3R)-3-[(1R,7aR)-octahydro-4-oxo-7a-methyl-1H-inden-1-yl]-butyl}-3-methyl-3-methoxymethyloxy-2(3H)-furanon 22) (3R,5S)-5-{(3R)-3-[(1R,7aR)-octahydro-4-oxo-7a-methyl-1H-inden-1-yl]-butyl}-3-methyl-3-methoxymethyloxy-2(3H)-furanon 23) (3S,5R)-5-{(3R)-3-[(1R,7aR)-octahydro-4-oxo-7a-methyl-1H-inden-1-yl]-butyl}-3-methyl-3-methoxymethyloxy-2(3H)-furanon 24) (3S,5S)-5-{(3R)-3-[(1R,7aR)-octahydro-4-oxo-7a-methyl- 1H-inden-1-yl]-butyl}-3-methyl-3-methoxymethyloxy-2(3H)-furanon 25) (3R,5R)-5-{(3R)-3-[(1R,7aR)-octahydro-4-oxo-7a-methyl-1H-inden-1-yl]-butyl}-3-methyl-3-tetrahydropyranyloxy-2(3H)-furanon 26) (3R,5S)-5-{(3R)-3-[(1R,7aR)-octahydro-4-oxo-7a-methyl-1H-inden-1-yl]-butyl}-3-methyl-3-tetrahydropyranyloxy-2(3H)-furanon 27) (3S,5R)-5-{(3R)-3-[(1R,7aR)-octahydro-4-oxo-7a-methyl-1H-inden-1-yl]-butyl}-3-methyl-3-tetrahydropyranyloxy-2(3H)-furanon 28) (3S,5S)-5-{(3R)-3-[(1R,7aR)-octahydro-4-oxo-7a-methyl-1H-inden-1-yl]-butyl}-3-methyl-3-tetrahydropyranyloxy-2(3H)-furanon

EXAMPLES

The present invention will now be explained in further detail by way of Examples, which, however, do not restrict the present invention in any way.

EXAMPLE 1-1

Production of (2R)-2-[(1R,7aR)-octahydro-4-trimethylsilyloxy-7a-methyl-1H-inden-1-yl]-propyl-p-toluenesulfonate

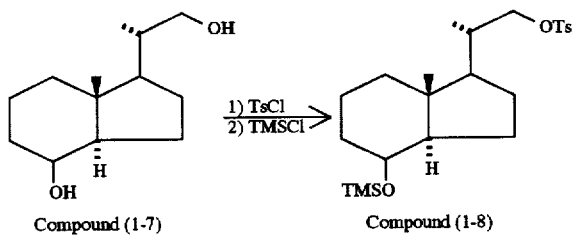

Compound (1-7)     Compound (1-8)

A 2.0 g amount of the compound (1-7), (2R)-2-[(1R,7aR)(4E)-octahydro-4-hydroxy-7a-methyl-1-H-inden-1-yl]-propanol, and 2.3 g of p-toluenesulfonyl chloride were placed into a 100 ml eggplant-shaped flask. These were dissolved in 10 ml of dried dichloromethane, then the solution was stirred under ice-cooling. A 4 ml amount of pyridine was added thereto, then the solution was stirred under ice cooling for 6 hours.

The reaction solution was poured into 100 ml of ethyl acetate and 20 ml of water and extracted. The organic layer was washed 2 times with a saturated aqueous solution of potassium hydrogensulfate, a saturated aqueous solution of sodium bicarbonate, and saturated saline, then was dried over anhydrous magnesium sulfate. The desiccant was filtered out, then the solvent was distilled off under reduced pressure to obtain a crude product in an amount of 4.2 g. This was placed in a 100 ml eggplant-shaped flask, then 2.04 g of imidazole was added. Thereto 20 ml of dried dichloromethane was added. The solution was then stirred under ice-cooling. Next, 1.91 ml of trimethylsilyl chloride was added thereto and the solution was stirred at room temperature over night. The reaction solution was poured into 100 ml of ethyl acetate and 20 ml of water and extracted. The organic layer was then washed 2 times with saturated saline, then was dried over anhydrous magnesium sulfate. The desiccant was filtered out and the solvent was distilled off under reduced pressure to obtain a crude product in an amount of 4.07 g. This was purified by a silica gel column (IR-60, 200 g, hexane/ethyl acetate=9/1) to obtain the desired product (1-8), (2R)-2-[(1R,7aR)-octahydro-4-trimethylsilyloxy-7a-methyl-1H-inden-1-yl]-propyl-p-toluenesulfonate in an amount of 3.27 g (yield 87%).

¹H-NMR (CDCl₃, δ ppm)

7.78 (d, 2H, J=18 Hz), 7.34 (d, 2H, J=18 Hz), 3.9 to 4.0 (m, 1H), 3.95 (dd, 1H, J=3 & 9.2 Hz), 3.79 (dd, 1H, J=4.3 & 9.2 Hz), 2.45(s, 3H), 1.00 to 2.00 (m, 13H), 0.89 (d, 3H J=18 Hz), 0.83 (s, 3H), 0.03 (s, 9H)

EXAMPLE 1-2

Process of production of (2R)-2-[(1R,7aR)-octahydro-4-trimethylsilyloxy-7a-methyl-1H-inden-1-yl]-iodopropane

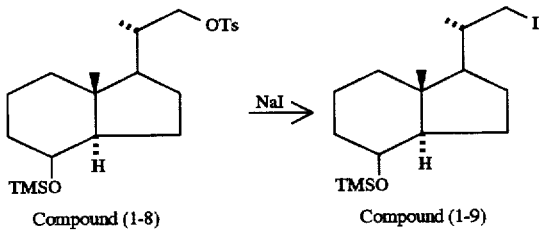

Compound (1-8)     Compound (1-9)

A 3.27 g amount of the compound (1-8), (2R)-2-[(1R,7aR)-octahydro-4-trimethylsilyloxy-7a-methyl-1H-inden-1-yl]-propyl-p-toluenesulfonate, was dissolved in 200 ml of acetone in a 500 ml eggplant-shaped flask. To this was added 5 g of sodium iodide. The solution was then heated and refluxed over night.

The reaction solution was allowed to cool, then the precipitate was filtered out and the solvent was distilled off under reduced pressure. A 300 ml amount of ether and 200 ml of water were added to the residue and separation performed. Extraction was performed from the aqueous layer by 200 ml of ether, then the organic layer was washed 2 times with a saturated aqueous solution of sodium hydrogencarbonate and saturated saline. The result was dried over anhydrous magnesium sulfate, the desiccant was filtered out, then the solvent was distilled off under reduced pressure to obtain a crude product in an amount of 4.5 g. This was purified by a silica gel column (IR-60, 80 g, hexane) to obtain the desired product (1-9), (2R)-2-[(1R,7aR)-octahydro-4-trimethylsilyloxy-7a-methyl-1H-inden-1-yl]-iodopropane, in an amount of 2.72 g (yield 94%).

¹H-NMR (CDCl₃, δ ppm)

3.99 (m, 1H), 3.33 (dd, 1H J=2 & 5 Hz), 3.17 (dd, 1H J=5 & 9 Hz), 1.00 to 2.00 (m, 13H), 0.99 (d, 3H, J=5.6 Hz), 0.92 (s, 3H), 0.05 (s, 9H)

EXAMPLE 1-3

Production of (4S)-4-{(2R)-2-[(1R,7aR)-octahydro-4-trimethylsilyloxy-7a-methyl-1H-inden-1-yl]-propyl}-2-cyclopenten-1-one

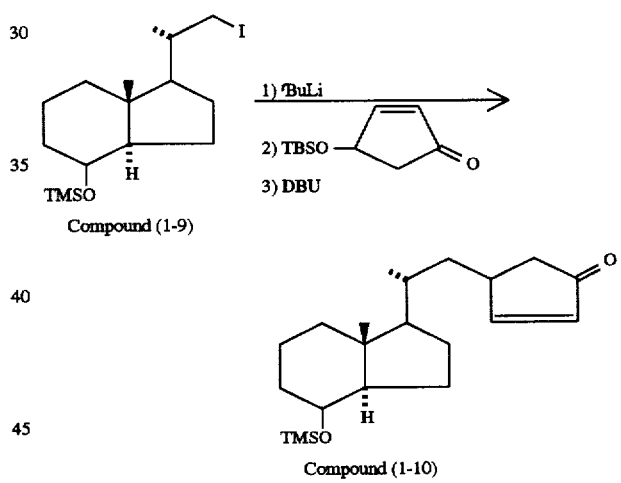

Compound (1-9)

Compound (1-10)

A 10 ml amount of ether was placed into a 100 ml eggplant-shaped flask and cooled to −78° C., followed by adding 14.3 ml of a hexane solution of t-butyllithium (1.54 mol/liter). A 3.94 g amount of the compound (1-9), (2R)-2-[(1R,7aR)-octahydro-4-trimethylsilyloxy-7a-methyl-1H-inden-1-yl]-iodopropane was dissolved in 10 ml of ether and then added to the above solution which was then stirred at −78° C. for 1 hour. A 2.1 g amount of copper iodide and 5.5 ml of tri(N-butyl)phosphine were dissolved in 10 ml of tetrahydrofuran, the solution was then added to the above reaction solution, then this was stirred at −78° C. for 1 hour. Thereto 2.54 g of (4S)-4-(t-butyldimethylsilyloxy)-2-cyclopenten-1-one dissolved in 10 ml of tetrahydrofuran was added. The solution was then stirred at −40° C. for 2 hours. This was poured into 30 ml of a saturated aqueous solution of ammonium chloride, then extraction was performed by 50 ml, 30 ml of ether. The organic layer was washed 2 times with saturated saline, then was dried over anhydrous sodium sulfate, the desiccant was filtered out, and the solvent was distilled off under reduced pressure to obtain a crude product in an amount of 11.7 g. This was dissolved in 150 ml of dichloromethane, 2 ml of 1,8-diazabicyclo[5.4.0]undecene was added, then the solution was stirred at room temperature over night. Thereto 400 ml of ether was added. This was then washed by a saturated aqueous solution of potassium hydrogensulfate, a saturated aqueous solution of sodium hydrogencarbonate, and saturated saline and was dried over anhydrous magnesium sulfate. The desiccant was filtered out, then the solvent was distilled off under reduced pressure to obtain a crude product in an amount of 10.9 g. This was purified by a silica gel column (IR-60, 400 g, hexane/ethyl acetate=40/1, 19/1, 9/1) to obtain the desired product (1-10), (4S)-4-{(2R)-2-[(1R,7aR)-octahydro-4-trimethylsilyloxy-7a-methyl-1H-inden-1-yl]-propyl}-2-cyclopenten-1-one in an amount of 1.76 g (yield 50%).

$^1$H-NMR (CD$_3$Cl, δ ppm)

7.57 (dd, 1H, J=2.3 & 5.6 Hz), 6.10 (dd, 1H J=2 & 5.6 Hz), 3.99 (m, 1H), 2.80 to 3.10 (m, 1H), 2.50 (dd, 1H, J=6.3 & 18.8 Hz), 1.00 to 2.00 (m, 16H), 0.97 (d, 3H J=6.3 Hz), 0.90 (s, 3H), 0.05 (s, 9H)

EXAMPLE 1-4

Production of (1R, 4S)-4-{(2R)-2-[(1R,7aR)-octahydro-4-trimethylsilyloxy-7a-methyl-1H-inden-1-yl]-propyl}-1-methyl-2-cyclopenten-1-ol and (1S,4S)-4-{(2R)-2-[(1R,7aR)-octahydro-4-trimethylsilyloxy-7a-methyl-1H-inden-1-yl]-propyl}-1-methyl-2-cyclopenten-1-ol

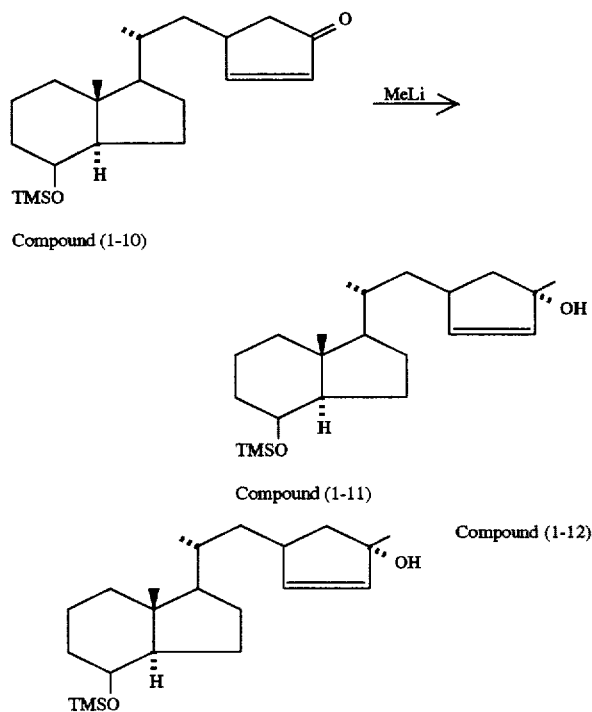

A 1.76 g amount of the compound (1-10), (4S)-4-{(2R)-2-[(1R, 7aR)-octahydro-4-trimethylsilyloxy-7a-methyl-1H-inden-1-yl]-propyl}-2-cyclopenten-1-one was placed into a 300 ml eggplant-shaped flask. A 150 ml amount of tetrahydrofuran was added and the solution stirred and cooled to −78° C., and then, 6.5 ml of an ether solution of methyllithium (1.16 mol/liter) was added, followed by stirring for 15 minutes. A 50 ml amount of saturated saline was added, the excess methyllithium was broken down, then 100 ml of ether was added for separation. The organic layer was washed with saturated saline, then was dried over anhydrous magnesium sulfate. The desiccant was filtered out, the solvent was distilled off under reduced pressure, and the crude product was purified by a silica gel column (Merck gel: 300 g, hexane/ethyl acetate=15/1 to 9/1) to obtain the desired product (1-11), (1R,4S)-4-{(2R)-2-[(1R,7aR)-octahydro-4-trimethylsilyloxy-7a-methyl-1H-inden-1-yl]-propyl}-1-methyl-2-cyclopenten-1-ol in an amount of 1.55 g (yield 84%) and the desired product (1-12), (1S,4S)-4-{(2R)-2-[(1R,7aR)-octahydro-4-trimethylsilyloxy-7a-methyl-1H-inden-1-yl]-propyl}-1-methyl-2-cyclopenten-1-ol, in an amount of 0.27 g (yield 14%).

Compound (1-11) $^1$H-NMR (D$_6$-acetone, δ ppm)

5.40 to 5.60 (m, 2H), 4.00 (brs, 1H), 2.50 to 2.70 (m, 1H), 0.90 to 2.20 (m, 18H), 1.18 (s, 3H), 0.88 (d, 3H J=5 Hz), 0.87 (s, 3H), 0.03 (s, 9H)

Compound (1-12) $^1$H-NMR (D$_6$-acetone, δ ppm)

5.54 (s, 2H), 3.90 to 4.00 (m, 1H), 2.80 to 3.00 (m, 1H), 0.90 to 2.10 (m, 18H), 1.26 (s, 3H), 0.87 (d, 3H, J=6.3 Hz), 0.87 (s, 3H), 0.03 (s, 9H)

EXAMPLE 1-5

Production of (1R,4S)-4-{(2R)-2-[(1R,7aR)-octahydro-4-hydroxy-7a-methyl-1H-inden-1-yl]-propyl}-1-methyl-2-cyclopenten-1-ol

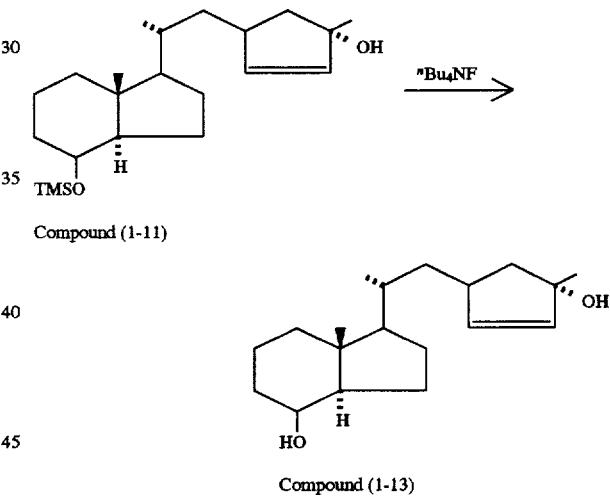

A 1.55 g amount of the compound (1-11), (1R,4S)-4-{(2R)-2-[(1R,7aR)-octahydro-4-trimethylsilyloxy-7a-methyl-1H-inden-1-yl]-propyl}-1-methyl-2-cyclopenten-1-ol was taken in a 100 ml eggplant-shaped flask, then 20 ml of THF was added and the solution stirred under ice-cooling. Then, 5.1 ml of a tetrahydrofuran solution (1 mol/liter) of tetra-n-butylammonium fluoride was added thereto and, then the solution was stirred for 1 hour. The reaction solution was poured in 100 ml of ether and 30 ml of water and extracted. The organic layer was washed 4 times with saturated saline, then was dried over anhydrous magnesium sulfate. The desiccant was filtered out and the solvent was distilled off under reduced pressure to obtain a crude product in an amount of 1.29 g. This was purified by a silica gel column (IR-60, 150 g, hexane/ethyl acetate=15/1 to 1/1) to obtain the desired product (1-13), (1R,4S)-4-{(2R)-2-[(1R,7aR)-octahydro-4-trimethylsilyloxy-7a-methyl-1H-inden-1-yl]-propyl}-1-methyl-2-cyclopenten-1-ol in an amount of 1.21 g (yield 97%).

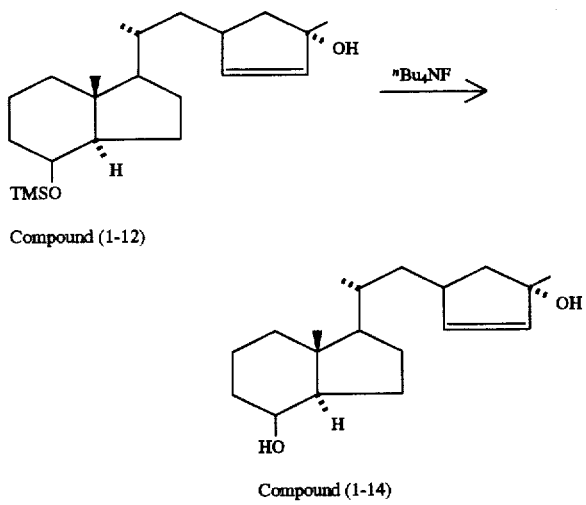

Compound (1-12)

Compound (1-14)

Similarly, 260 mg of the compound (1-12), (1S,4S)-4-{(2R)-2-[(1R,7aR)-octahydro-4-trimethylsilyloxy-7a-methyl-1H-inden-1-yl]-propyl}-1-methyl-2-cyclopenten-1-ol was treated in the same way to obtain the desired product (1-14), (1S,4S)-4-{(2R)-2-[(1R,7aR)-octahydro-4-hydroxy-7a-methyl-1H-inden-1-yl]-propyl}-1-methyl-2-cyclopenten-1-ol in an amount of 174 mg (yield 84%).

Compound (1-13) ¹H-NMR (D₆-acetone, δ ppm)

5.50 to 5.70 (m, 2H), 4.08 (brs, 1H), 2.60 to 2.80 (m, 1H), 1.00 to 2.20 (m, 19H), 1.32 (s, 3H), 1.06 (s, 3H), 1.03 (d, 3H, J=9.3 Hz)

Compound (1-14) ¹H-NMR (D₆-acetone, δ ppm)

5.59 (s, 2H), 4.08 (brs, 1H), 2.80 to 3.00 (m, 1H), 1.00 to 2.30 (m, 19H), 1.32 (s, 3H), 0.98 (s, 3H), 0.93 (d, 3H J=9.6 Hz)

EXAMPLE 1-6

Production of (1R,4S)-4-{(2R)-2-[(1R,7aR)-octahydro-4-oxo-7a-methyl-1H-inden-1-yl]-propyl}-1-methyl-2-cyclopenten-1-ol

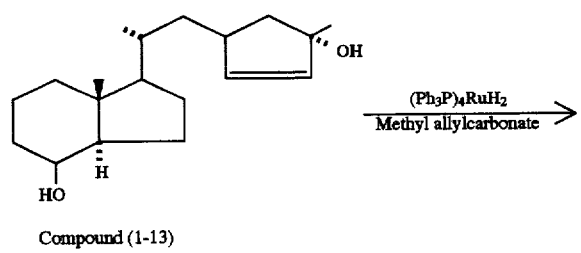

Compound (1-13)

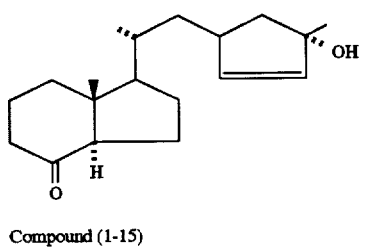

Compound (1-15)

A 277 mg amount of the compound (1-13), (1R,4S)-4-{(2R)-2-[(1R,7aR)-octahydro-4-hydroxy-7a-methyl-1H-inden-1-yl]-propyl}-1-methyl-2-cyclopenten-1-ol was dissolved in 25 ml of toluene in a 100 ml eggplant-shaped flask, then the solution was stirred under a nitrogen atmosphere. Thereafter, 115 mg of tetrakis-triphenylphosphine ruthenium dihydride and 5 ml of methylallyl carbonate was added thereto, and then the solution was stirred at 80° to 100° C. for 1 day. The reaction solution was filtered by Celite, the solvent was distilled off under reduced pressure, and the residue was purified by a silica gel column (IR-60, 80 g, hexane/ethyl acetate=3/1, 1/1) to obtain the desired product (1-15), (1R,4S)-4-{(2R)-2-[(1R,7aR)-octahydro-4-oxo-7a-methyl-1H-inden-1-yl]-propyloxy}-1-methyl-2-cyclopenten-1-ol, in an amount of 221 mg (yield 79%).

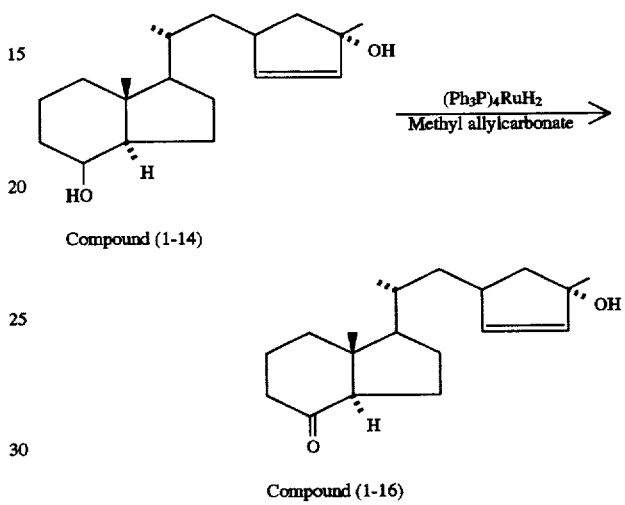

Compound (1-14)

Compound (1-16)

A 62 mg amount of the compound (1-14), (1S,4S)-4-{(2R)-2-[(1R,7aR)-octahydro-4-hydroxy-7a-methyl-1H-inden-1-yl]-propyl}-1-methyl-2-cyclopenten-1-ol, was treated in the same way to obtain the desired product (1-16), (1S,4S)-4-{(2R)-2-[(1R,7aR)-octahydro-4-oxo-7a-methyl-1H-inden-1-yl]-propyl}-1-methyl-2-cyclopenten-1-ol in an amount of 52 mg (yield 84%).

Compound (1-15) ¹H-NMR (CD₃Cl, δ ppm)

5.60 to 5.70 (m, 2H), 2.60 to 2.80 (m, 1H), 1.20 to 2.50 (m, 18H), 1.35 (s, 3H), 0.99 (d, 3H J=9.3 Hz), 0.65 (s, 3H)

Compound (1-16) ¹H-NMR (CD₃Cl, δ ppm)

5.60 to 5.70 (m, 2H), 2.80 to 3.00 (m, 1H), 1.00 to 2.50 (m, 18H), 1.43 (s, 3H), 0.99 (d, 3H, J=9.3 Hz), 0.66 (s, 3H)

EXAMPLE 1-7

Production of (1R,4S)-4-{(2R)-2-[(1R,7aR)-octahydro-4-oxo-7a-methyl-1H-inden-1-yl]-propyl}-1-methyl-1-trimethylsilyloxy-2-cyclopentene

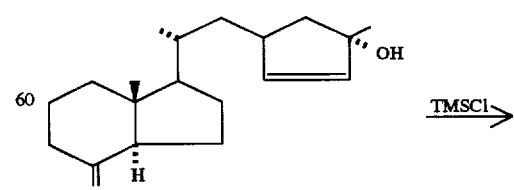

Compound (1-15)

-continued

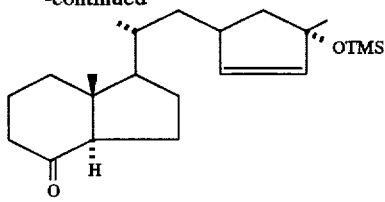

Compound (1-17)

A 177 mg amount of the compound (1-15), (1R,4S)-4-{(2R)-2-[(1R,7aR)-octahydro-4-oxo-7a-methyl-1H-inden-1-yl]-propyloxy}-1-methyl-2-cyclopenten-1-ol, and 128 mg of imidazole were placed in a 100 ml eggplant-shaped flask. Next, 20 ml of dried dichloromethane was added and the solution was stirred. A 120 μl amount of trimethylsilyl chloride was added under ice cooling, then the solution was stirred at the same temperature for 30 minutes. The reaction solution was poured in 50 ml of ether and 30 ml of water and extracted. The organic layer was washed 2 times with saturated saline, then was dried over anhydrous magnesium sulfate. The desiccant was filtered out and the solvent was distilled off under reduced pressure. The obtained residue was purified by a silica gel column (IR-60, 80 g, hexane/ethyl acetate=19/1, 4/1) to obtain the desired product (1-17), (1R, 4S)-4-{(2R)-2-[(1R,7aR)-octadehydro-4-oxo-7a-methyl-1H-inden-1-yl]-propyloxy}-1-methyl-1-trimethylsilyloxy-2-cyclopentene in an amount of 188 mg (yield 85%).

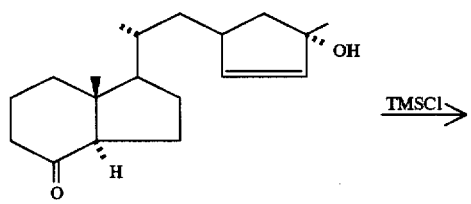

Compound (1-16)

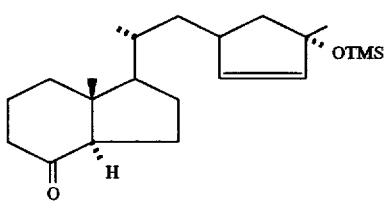

Compound (1-18)

A 52 mg amount of the compound (1-16), (1S,4S)-4-{(2R)-2-[(1R,7aR)-octahydro-4-oxo-7a-methyl-1H-inden-1-yl]-propyl}-1-methyl-2-cyclopenten-1-ol, was treated in the same way to obtain the desired product (1-18), (1S,4S)-4-{(2R)-2-[(1R,7aR)-octahydro-4-oxo-7a-methyl-1H-inden-1-yl]-propyl}-1-methyl-2-cyclopenten-1-ol in an amount of 49 mg (yield 75%).

Compound (1-17) $^1$H-NMR (CD$_3$Cl, δ ppm)

5.71 (dd, 1H, J=2 & 5.6 Hz), 5.56 (dd, 1H, J=1.65 & 5.6 Hz), 2.60 to 2.80 (m, 1H), 1.10 to 2.50 (m, 17H), 1.31 (s, 3H), 0.98 (d, 3H, J=9.3 Hz), 0.65 (s, 3H), 0.12 (s, 9H)

Compound (1-18) $^1$H-NMR (CD$_3$Cl, δ ppm)

5.50 to 5.65 (m, 2H), 2.80 to 2.90 (m, 1H), 1.10 to 2.50 (m, 17H), 1.31 (s, 3H), 0.98 (d, 3H J=9.3 Hz), 0.56 (s, 3H), 0.07 (s, 9H)

EXAMPLE 1-8

Production of (1R,4S)-4-{(2R)-2-[(1R,7aR)-octahydro-4-bromomethylene-7a-methyl-1H-inden-1-yl]-propyl}-1-methyl-2-cyclopenten-1-ol

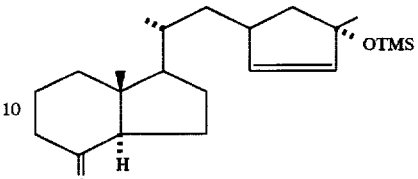

Compound (1-17)

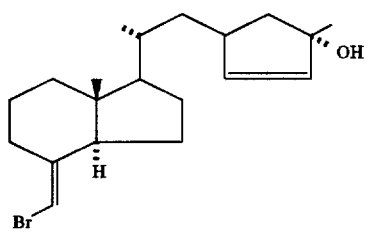

Compound (1-19)

A 5.30 g amount of bromomethylene-triphenylphosphonium bromide was taken in a 200 ml eggplant-shaped flask, 30 ml of dried tetrahydrofuran was added, and the solution was stirred and cooled by a –65° C. bath. Next, 12.2 ml of a 1M solution of sodium bistrimethylsilylamide in tetrahydrofuran was added dropwise and the solution stirred at the same temperature for 1 hour. Thereafter, 10 ml of a tetrahydrofuran solution of 882 mg of the compound (1-17), (1R,4S)-4-{(2R)-2-[(1R,7aR)-octahydro-4-oxo-7a-methyl-1H-inden-1-yl]-propyloxy}-1-methyl-1-trimethylsilyloxy-2-cyclopentene was added dropwise, the cooling bath was removed, then the solution was stirred at room temperature for 30 minutes. Further, hexane was added to the reaction solution which was then further stirred. The precipitate was filtered out and the solvent was distilled off under reduced pressure. The obtained residue was dissolved in 10 ml of tetrahydrofuran and the solution stirred while cooling by ice. To this was added 5 ml of a tetrahydrofuran solution (1 mol/liter) of tetra(n-butyl)ammonium fluoride, then the solution was stirred under ice cooling for 1 hour. The reaction solution was poured in 100 ml of ethyl acetate and 30 ml of water and separated. The organic layer was washed with saline, then was dried over anhydrous magnesium sulfate. The desiccant was filtered out, then the solvent was distilled off under reduced pressure and the obtained residue was purified by a silica gel column (IR-60, 200 g, hexane/ethyl acetate=19/1 to 2/1) to obtain the desired product (1-19), (1R, 4S)-4-{(2R)-2-[(1R,7aR)-octahydro-4-bromomethylene-7a-methyl-1H-inden-1-yl]-propyl}-1-methyl-2-cyclopenten-1-ol in an amount of 422 mg (yield 47%).

$^1$H-NMR (CDCl$_3$, δ ppm)

5.50 to 5.70 (br, 3H), 2.80 to 2.90 (m, 1H), 2.60 to 2.80 (m, 1H), 2.10 to 2.25 (m, 1H), 1.20 to 2.00 (m, 16H), 1.35 (s, 3H), 0.96 (d, 3H J=6.3 Hz), 0.57 (s, 3H)

EXAMPLE 1-9

Production of (1R,4S)-4-{(2R)-2-[(1R,7aR)-octahydro-4-bromomethylene-7a-methyl-1H-inden-1-yl]-propyl}-1-methyl-1-trimethylsilyloxy-2-cyclopentene

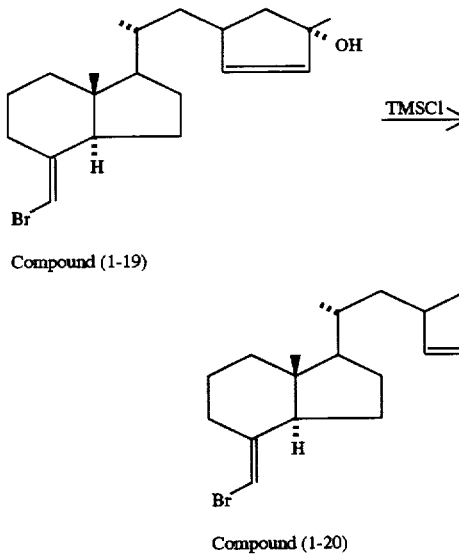

Compound (1-19)

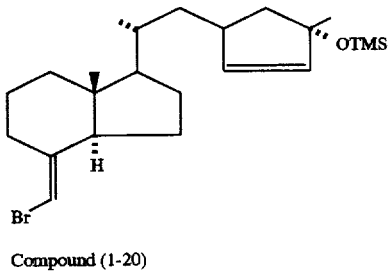

Compound (1-20)

A 422 mg amount of the compound (1-19), (1R,4S)-4-{(2R)-2-[(1R,7aR)-octahydro-4-bromomethylene-7a-methyl-1H-inden-1-yl]-propyl}-1-methyl-2-cyclopenten-1-ol and 158 mg of imidazole were added to a 100 ml eggplant-shaped flask. Next, 5 ml of dried dichloromethane was added and stirred in, then 175 μl f trimethylsilyl chloride was added under ice cooling and the solution stirred at the same temperature for 30 minutes. The reaction solution was poured into 50 ml of ether and 20 ml of water and extracted. The organic layer was washed 2 times with saturated saline, then was dried over anhydrous magnesium sulfate, the desiccant was filtered out, the solvent was distilled off under reduced pressure, and the obtained residue was purified by a silica gel column (IR-60, 150 g, hexane/ethyl acetate=50/1 to 19/1) to obtain the desired product (1-20), (1R,4S)-4-{(2R)-2-[(1R,7aR)-octahydro-4-bromomethylene-7a-methyl-1H-inden-1-yl]-propyl}-1-methyl-2-cyclopenten-1-ol in an amount of 422 mg (yield 84%).

¹H-NMR (CDCl₃, δ ppm)

5.50 to 5.70 (m, 2H), 5.53 (s, 1H), 1.10 to 3.00 (m, 18), 1.35 (s, 3H), 0.94 (d, 3H, J=6.3 Hz), 0.56 (s, 3H), 0.11 (s, 9H)

EXAMPLE 1-10

Production of 23,24,25,26,27-pentanol-1α-hydroxy-22-[(1R,4S)-1-trimethylsilyloxy-1-methyl-2-cyclopenten-4-yl]-vitamin D₃-1α,3-bistrimethylsilylether

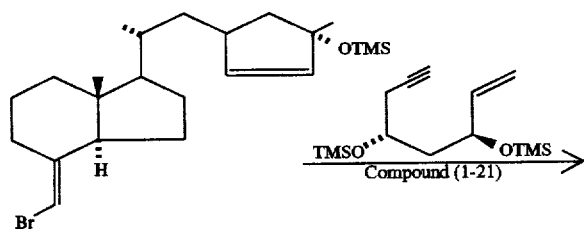

Compound (1-20)

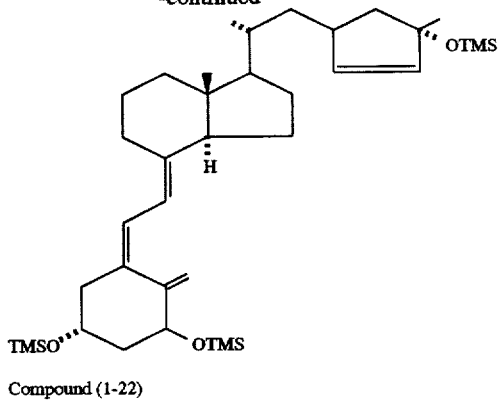

Compound (1-22)

A 63.7 mg amount of triphenylphosphine was taken in a dried eggplant-shaped flask and deaerated. To this was added 20 mg of tris(dibenzylideneacetone)dipalladium chloroform, followed by further deaeration. A 7.2 ml amount of a mixed solvent of distilled toluene/diisopropylethylamine=1/1 was added under a nitrogen atmosphere, then the solution was stirred at room temperature for 20 minutes. Next, 88 mg of the compound (1-20), (1R,4S)-4-{(2R)-2-[(1R,7aR)-octahydro-4-bromomethylene-7a-methyl-1H-inden-1-yl]-propyl}-1-methyl-1-trimethylsilyloxy-2-cyclopentene and 57 mg of the compound (1-21), (3S,5R)-bistrimethylsilyloxy-1-octen-7-yne were dissolved in 2 ml of a mixed solvent of distilled toluene/diisopropylethylamine=1/1 and then added dropwise to the above reaction solution. The solution was heated and refluxed for 1.5 hours, then returned to room temperature. The reaction solution was poured into 50 ml of ethyl acetate and 10 ml of a saturated aqueous solution of potassium hydrogensulfate and extracted. The organic layer was washed by a saturated aqueous solution of sodium hydrogencarbonate and saturated saline, then was dried over anhydrous magnesium sulfate. The desiccant was filtered out and the solvent was distilled off under reduced pressure to obtain a crude product in an amount of 300 mg. This was purified by a silica gel column (Merck gel, 200 g, hexane/ethyl acetate=100/1 to 20/1) to obtain the desired product (1-22), 23,24,25,26,27-pentanol-1α, 3-hydroxy-22-[(1R,4S)-1-trimethylsilyloxy-1-methyl-2-cyclopenten-4-yl]-vitamin D₃-1α,3-bistrimethylsilyl-ether in an amount of 58.8 mg (yield 46%).

¹H-NMR (CDCl₃, δ ppm)

6.27 (d-like, 1H), 6.04 (d-like, 1H), 5.50 to 5.60 (m, 2H), 5.20 (s, 1H), 4.90 (brs, 1H), 4.30 to 4.40 (m, 1H), 4.10 to 4.20 (m, 1H), 1.10 to 3.00 (m, 22H), 1.32 (s, 3H), 0.94 (d, 3H J=6.3 Hz), 0.55 (s, 3H), 0.00 to 0.20 (m, 18H)

EXAMPLE 1-11

Production of 23,24,25,26,27-pentanol-1α-hydroxy-22-[(1R, 4S)-1-hydroxy-1-methyl-2-cyclopenten-4-yl]-vitamin D₃

45

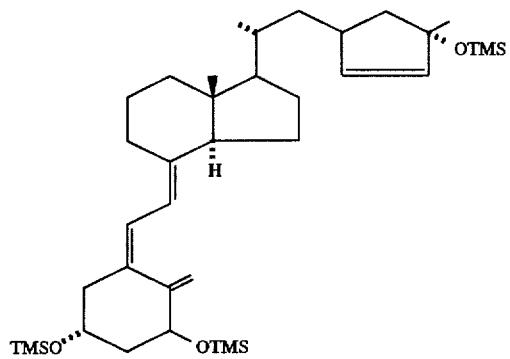

Compound (1-22)

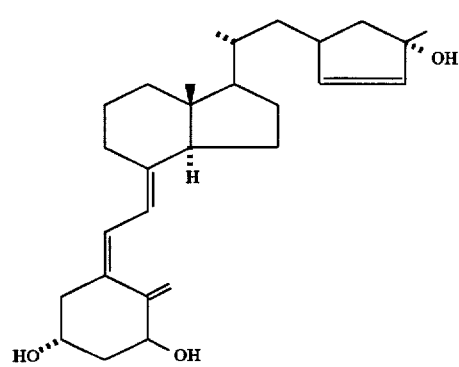

Compound (1-23)

A 58.8 mg amount of the compound (1-22), 23,24,25,26, 27-pentanol-1α-hydroxy-22-[(1R,4S)-1-trimethylsilyloxy-1-methyl-2-cyclopenten-4-yl]-vitamin D₃-1α,3-bistrimethylsilylether, was taken in a 25 ml eggplant-shaped flask, then 5 ml of dried tetrahydrofuran was added and the solution stirred. A 0.5 ml amount of a 1M solution of

46 tetrabutylammoniumfluoride in tetrahydrofuran was added and the solution stirred under ice cooling for 3 hours. The reaction solution was poured in 50 ml of ethyl acetate and 10 ml of a saturated aqueous solution of potassium hydrogensulfate and extracted. The organic layer was washed with a saturated aqueous solution of sodium bicarbonate and saturated saline, then was dried over anhydrous magnesium sulfate. The desiccant was filtered out, the solvent was distilled off under reduced pressure, and the obtained crude product was purified by a silica gel column (IR-60 Merck gel, 250 g, hexane/ethyl acetate=1/1 to 1/3) to obtain the desired product (1-23),23,24,25,26,27-pentanol-1α-hydroxy-22-[(1R, 4S)-1-hydroxy-1-methyl-2-cyclopenten-4-yl]-vitamin D₃ in an amount of 22.1 mg (yield 57%).

¹H-NMR (CDCl₃, δ ppm)

6.38 (d, 1H, J=11.2 Hz), 6.01 (d, 1H, J=11.2 Hz), 5.64 (s, 2H), 5.33 (s, 1H), 5.00 (s, 1H), 4.40 to 4.50 (m, 1H), 4.15 to 4.30 (m, 1H), 1.20 to 2.90 (m, 25H), 1.32 (s, 3H), 0.96 (d, 3H J=6.3 Hz), 0.55 (s, 3H)

EXAMPLE 2-1

Production of (4S,6R)-6-[(1R,7aR)-octahydro-4-hydroxy-7a-methyl-1H-inden-1-yl]-2-methoxycarbonyl-4-hydroxy-1-heptene and (4R,6R)-6-[(1R,7aR)-octahydro-4-hydroxy-7a-methyl-1H-inden-1-yl]-2-methoxycarbonyl-4-hydroxy-1-heptene

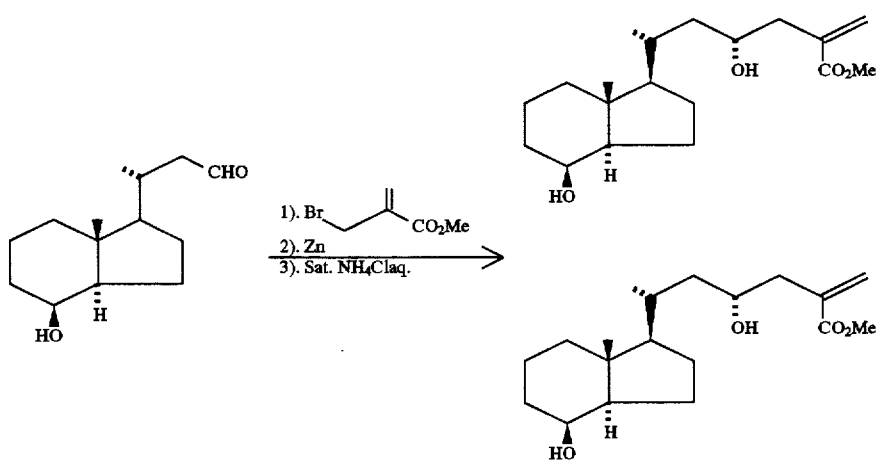

A 3.0 g amount of (3R)-3-[(1R,7aR)-octahydro-4-hydroxy-7a-methyl-1H-inden-1-yl]butanal was placed in a 500 ml eggplant-shaped flask, 100 ml of tetrahydrofuran was added, and the solution was stirred and cooled by an ice-cooled bath. A 3.2 ml amount of methyl-2-bromomethylacrylate was added dropwise to this. Next, 1.37 g of zinc powder and 390 ml of a saturated aqueous solution of ammonium chloride were added and the solution was stirred at the same temperature for 45 minutes.

A 150 ml amount of ethyl acetate was added to the reaction solution for extraction. The organic layer was washed 2 times with saturated saline, then was dried over anhydrous magnesium sulfate. The desiccant was filtered out and the solvent was distilled off under reduced pressure to obtain a crude product in an amount of 5.0 g. This was purified by a silica gel column (Merck gel, 250 g, hexane/ethyl acetate=9/1 to 3/1) to obtain (4S,6R)- 6-[(1R,7aR)-octahydro-4-hydroxy-7a-methyl-1H-inden-1-yl]-2-methoxycarbonyl-4-hydroxy-1-heptene (more polar) in an amount of 2.03 g and (4R,6R)-6-[(1R,7aR)-octahydro-4-hydroxy-7a-methyl-1H-inden-1-yl]-2-methoxycarbonyl-4-hydroxy-1-heptene (less polar) in an amount of 1.522 g (yield 81%).

¹H-NMR (CDCl₃, δ ppm)

6.25 (d, 1H, J=2 Hz), 5.66 (d, 1H, J=2 Hz), 4.07 (br, 1H), 3.82 to 3.88 (br, 1H), 3.77 (s, 3H), 2.51 (dd, 1H, J1=1 Hz, J2=9 Hz), 2.36 (dd, 1H, J1=8 Hz, J2=14 Hz), 0.96 (s, 1H), 0.94 (d, 3H, J=6 Hz), 6.27 (d, 1H, J=1 Hz), 5.69 (d, 1H, J=1 Hz), 4.07 (br, 1H), 3.80 to 3.86 (br, 1H), 3.77 (s, 3H), 2.69 (dd, 1H, J1=1 Hz, J2=10 Hz), 2.18 (dd, 1H, J1=9 Hz, J2=14 Hz), 0.98 (d, 3H, J=7 Hz), 0.95 (s, 3H).

EXAMPLE 2-2

Production of (5S)-5-{(2R)-2-[(1R,7aR)-octahydro-4-hydroxy-7a-methyl-1H-inden-1-yl]propyl}-3-methylene-dehydro-2(3H)-furanon

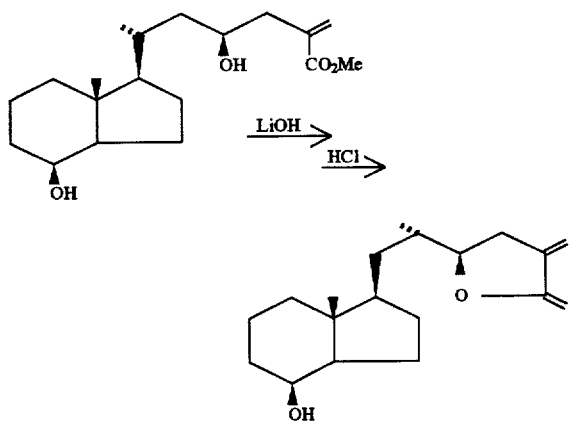

A 1.00 g amount of (4S,6R)-6-[(1R,7aR)-octahydro-4-hydroxy-7a-methyl-1H-inden-1-yl]-2-methoxycarbonyl-4-hydroxy-1-heptene was taken in a 100 ml eggplant-shaped flask, then 15 ml of tetrahydrofuran was added to dissolve it. Further, 15 ml of water was added and the solution was stirred and cooled by an ice-cooled bath. To this was added 6 ml of a 4N aqueous solution of lithium hydroxide, then the solution was stirred at the same temperature for 1 hour. Next, at the same temperature, concentrated hydrochloric acid was dropwise added to adjust the pH to 2, then the solution was stirred at room temperature for 3 hours. To the reaction solution were added 50 ml of water and 200 ml of ethyl acetate for extraction. The organic layer was further washed 3 times with water and was washed 2 times with saturated saline, then was dried over anhydrous magnesium sulfate. The desiccant was filtered out and the solvent was distilled off under reduced pressure to obtain (5S)-5-{(2R)-2-[(1R,7aR)-octahydro-4-hydroxy-7a-methyl-1H-inden-1-yl]propyl}-3-methylene-dehydro-2(3H)-furanon in an amount of 880 mg.

¹H-NMR (CDCl₃, δ ppm)

6.22 (t, 1H, J=3 Hz), 5.62 (t, 1H, J=2 Hz), 4.58 (dd, 1H, J1=7 Hz, J2=14 Hz), 4.08 (d, 1H, J=3 Hz), 3.01 to 3.10 (m, 1H), 2.56 to 2.6 (m, 1H), 1.00 (d, 3H, J=7 Hz), 0.95 (s, 3H).

EXAMPLE 2-3

Production of (5R)-5-{(2R)-2-[(1R,7aR)-octahydro-4-hydroxy-7a-methyl-1H-inden-1-yl]propyl}-3-methylenedehydro-2(3H)-furanon

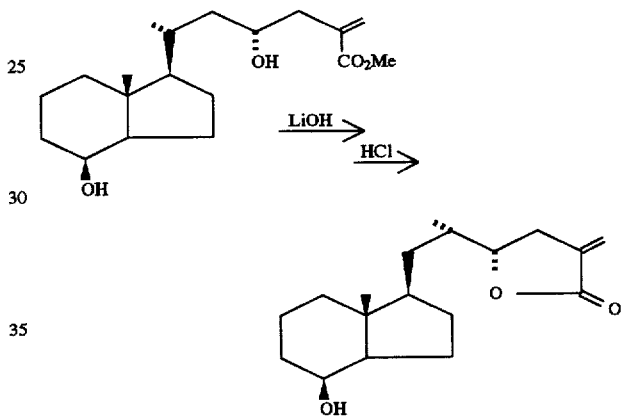

A 570 mg amount of (4R,6R)-6-[(1R,7aR)-octahydro-4-hydroxy-7a-methyl-1H-inden-1-yl]-2-methoxycarbonyl-4-hydroxy-1-heptene was taken in a 100 ml eggplant-shaped flask, then 5 ml of tetrahydrofuran was added to dissolve it. Further, 5 ml of water was added and the solution stirred and cooled by an ice-cooled bath. To this was added 3 ml of a 4 N aqueous solution of lithium hydroxide. The solution was stirred at the same temperature for 1 hour. Next, under the same temperature, concentrated hydrochloric acid was added dropwise to adjust the pH to 2, then the solution was stirred at room temperature for hours. To the reaction solution were added 50 ml of water and 200 ml of ethyl acetate for extraction. The organic layer was further washed 3 times with water and 2 times with saturated saline, then was dried over anhydrous magnesium sulfate. The desiccant was filtered out and the solvent was distilled off under reduced pressure to obtain (5R)-5-{(2R)-2-[(1R,7aR)-octahydro-4-hydroxy-7a-methyl-1H-inden-1-yl]propyl}-3-methylenedehydro-2(3H)-furanon in an amount of 451 mg.

EXAMPLE 2-4

Production of (5S)-5-{(2R)-2-[(1R,7R)-octahydro-4-oxo-7a-methyl-1H-inden-1-yl]propyl}-3-methylenedehydro-2(3H)-furanon

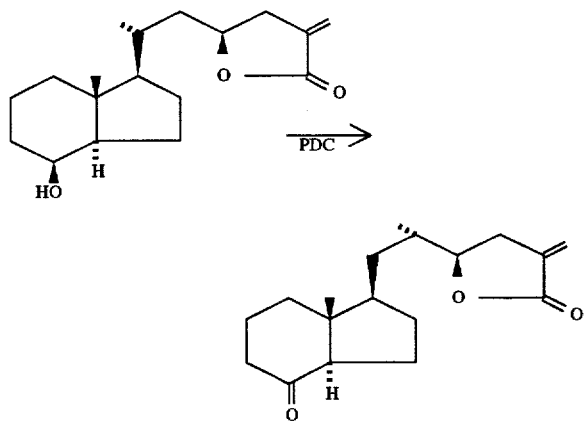

A 2.38 g amount of pyridinium bichromate was taken in a 200 ml eggplant-shaped flask, 50 ml of dimethyl formamide was added, then the solution was cooled by an ice-cooled bath. Thereafter, a solution of 880 mg of (5S)-5-{(2R)-2-[(1R,7R)-octahydro-4-hydroxy-7a-methyl-1H-inden-1-yl]propyl}-3-methylene-dehydro-2(3H)-furanon dissolved in 20 ml of dimethyl formamide was dropwise added and the solution was stirred at room temperature for 3 hours. A 200 ml amount of ether was added to the reaction solution, the insolubles were filtered out, then the result was washed with water and then saturated saline, then was dried over anhydrous magnesium sulfate. The desiccant was filtered out and the solvent was distilled off under reduced pressure to obtain a crude product in an amount of 1.02 g. This was purified by a silica gel column (Daiso gel IR-60, 150 g, hexane/ethyl acetate=3/1 to 2/1) to obtain (5S)-{(2R)-2-[(1R,7aR)-octahydro-4-oxo-7a-methyl-1H-inden-1-yl]propyl}-3-methylene-dehydro-2 (3H)-furanon in an amount of 700 mg (yield 69%).

$^1$H-NMR (CDCl$_3$, δ ppm)

6.23 (t, 1H, J=3 Hz), 5.63 (t, 1H, J=2 Hz), 4.6 to 4.7 (m, 1H), 3.0 to 3.13 (m, 1H), 2.4 to 2.6 (m,1H), 1.05 (d, H, J=7 Hz), 0.67 (s, 3H).

EXAMPLE 2-5

Production of (5R)-5-{(2R)-2-[(1R,7aR)-octahydro-4-oxo-7a-methyl-1H-inden-1-yl]propyl}-3-methylene-dehydro-2 (3H)-furanon

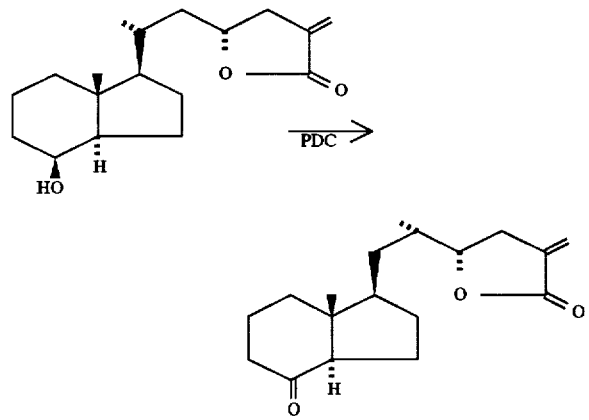

A 648 mg amount of pyridinium bichromate was taken in a 200 ml eggplant-shaped flask, 10 ml of dimethyl formamide was added, and the solution was cooled by an ice-cooled bath. Thereafter a solution of 240 mg of (5R)-5-{(2R)-2-[(1R,7aR)-octahydro-4-hydroxy-7a-methyl-1H-inden-1-yl]propyl}-3-methylene-dehydro-2(3H)-furanon dissolved in 10 ml of dimethyl formamide was dropwise added and the solution was stirred at room temperature for 3 hours. A 100 ml amount of ether was added to the reaction solution, the insolubles were filtered out, then the result was washed with water and saturated saline, then was dried over anhydrous magnesium sulfate. The desiccant was filtered out and the solvent was distilled off under reduced pressure to obtain a crude product in an amount of 600 mg. This was purified by a silica gel column (Daiso gel IR-60, 100 g, hexane/ethyl acetate=3/1 to 2/1) to obtain (5R)-{(2R)-2-[(1R,7aR)-octahydro-4-oxo-7a-methyl-1H-inden-1-yl]propyl}-3-methylene-dehydro-2(3H)-furanon in an amount of 327 mg.

$^1$H-NMR (CDCl$_3$, δ ppm)

6.23 (t, 1H, J=3 Hz), 5.63 (t, 1H, J=2 Hz), 4.59 (t, 1H, J=7 Hz), 3.0 to 3.10 (m, 1H), 2.4 to 2.6 (m, 1H), 1.07 (d, 3H, J=6 Hz), 0.66 (s, 3H).

EXAMPLE 2-6

Production of (3S,5S)-5-{(2R)-2-[(1R,7aR)-octahydro-4-oxo-7a-methyl-1H-inden-1-yl]propyl}-3-methyl-dehydro-2 (3H)-furanon

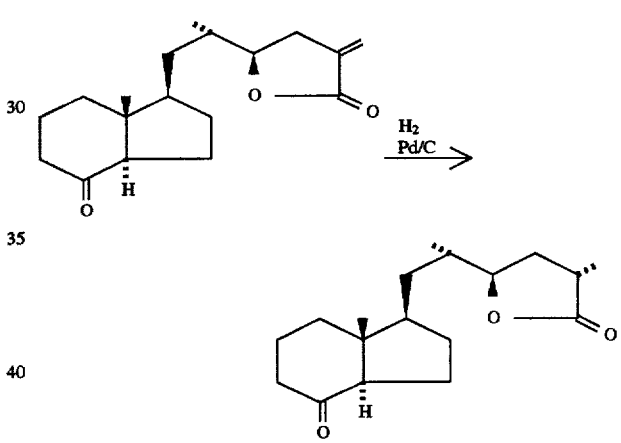

A 200 mg amount of (5S)-5-{(2R)-2-[(1R,7aR)-octahydro-4-oxo-7a-methyl-1H-inden-1-yl]propyl}-3-methylene-dehydro-2(3H)-furanon was taken in a 100 ml eggplant-shaped flask, 50 ml of ethanol was added, and the solution was stirred for dissolution. A 50 mg amount of 10% Pd/carbon was added under a nitrogen atmosphere, the atmosphere was replaced with hydrogen (balloon), then the solution was stirred at room temperature for 3 hours. The atmosphere was replaced with nitrogen, then the catalyst was filtered out and the solvent was distilled off under reduced pressure to obtain (3S,5S)-5-{(2R)-2-[(1R,7aR)-octahydro-4-oxo-7a-methyl-1H-inden-1-yl]propyl}-3-methyl-dehydro-2(3H)-furanon in an amount of 185 mg.

$^1$H-NMR (CDCl$_3$, δ ppm)

4.40 to 4.51 (m, 1H), 2.62 to 2.72 (m, 1H), 2.41 to 2.51 (m, 2H), 2.27 (d, 3H, J=7 Hz), 1.03 (d, 3H, J=7 Hz), 0.66 (s, 3H).

EXAMPLE 2-7

Production of (3S,5S)-5-{(2R)-2-[(1R,7aR)-octahydro-4-bromomethylene-7a-methyl-1H-inden-1-yl]propyl}-3-methyl-dehydro-2(3H)-furanon

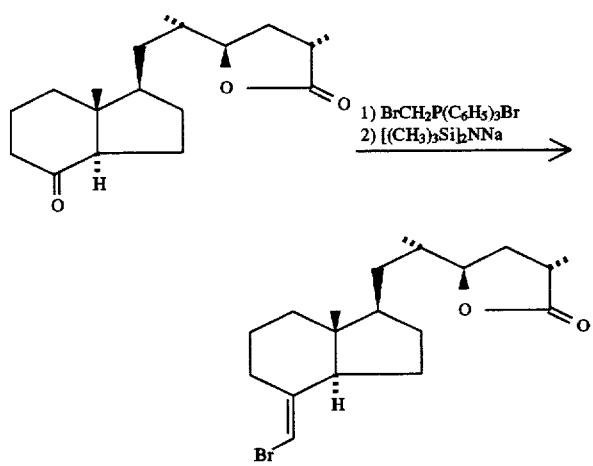

A 1.79 g amount of bromomethylenetriphenylphosphonium bromide was taken in a 100 ml eggplant-shaped flask, 20 ml of dried tetrahydrofuran was added, and the solution was stirred and cooled by a −70° C. cooling bath. Thereafter 3.9 ml of a 1 M [(CH₃)₃Si]₂NNA/tetrahydrofuran solution was dropwise added, then the solution was stirred at the same temperature for 1 hour. Next, a solution of 120 mg of (3S,5S)-5-{(2R)-2-[(1R,7aR)-octahydro-4-oxo-7a-methyl-1H-inden-1-yl]propyl}-3-methyl-dehydro-2(3H)-furanon dissolved in 5 ml of dried tetrahydrofuran was dropwise added to this. The cooling bath was removed, then the solution was stirred for 2 hours. Next, hexane was added and the insolubles filtered out, then the solvent was distilled off under reduced pressure to obtain a crude product in an amount of 1.2 g. This was purified by a silica gel column (Daiso gel IR-60, 80 g, hexane/ethyl acetate=15/1) to obtain (3S,5S)-5-{(2R)-2-[(1R,7aR)-octahydro-4-bromomethylene-7a-methyl-1H-inden-1-yl]propyl}-3-methyl-dehydro-2(3H)-furanon in an amount of 69 mg (yield 46%).

¹H-NMR (CDCl₃, δ ppm)

5.65 (d,1H, J=2 Hz), 4.40 to 4.50 (m, 1H), 2.85 to 2.90 (m, 1H), 2.62 to 2.72 (m, 1H), 2.41 to 2.50 (m, 1H), 2.67 (d, 3H, J=7 Hz), 1.00 (d, 3H, J=7 Hz), 0.58 (s, 3H).

EXAMPLE 2-8

Production of (2R)-2-[(1R,7aR)-octahydro-4-bromomethylene-7a-methyl-1H-inden-1-yl]propylparatoluene sulfonate

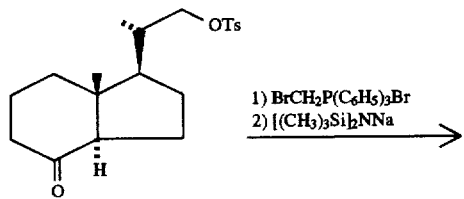

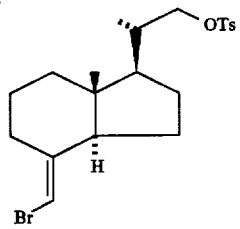

A 2.39 g amount of bromomethylenetriphenylphosphonium bromide was taken in a 100 ml eggplant-shaped flask, 40 ml of dried tetrahydrofuran was added, and the solution was stirred and cooled by a −70° C. cooling bath. Thereafter 5.28 ml of a 1 M [(CH₃)₃Si]₂ NNa/tetrahydrofuran solution was dropwise added, then the solution was stirred at the same temperature for 1 hour. Next, a solution of 300 mg of (2R)-2-[(1R,7aR)-octahydro-4-oxo-7a-methyl-1H-inden-1-yl]propylparatoluene sulfonate dissolved in 10 ml of dried tetrahydrofuran was added dropwise. The cooling bath was removed and then the solution was stirred for 1 hour. Next, hexane was added and the insolubles were filtered out, then the solvent was distilled off under reduced pressure to obtain a crude product in an amount of 2.5 g. This was purified by a silica gel column (Merck gel, 100 g, hexane/ethyl acetate=14/1, 9/1) to obtain {(2R)-2-[(1R,7aR)-octahydro-4-bromomethylene-7a-methyl-1H-inden-1-yl]propylparatoluene sulfonate in an amount of 178 mg (yield 48%).

¹H-NMR (CDCl₃, δ ppm)

7.78 (d, 2H, J=8 Hz), 7.35 (d, 2H, J=8 Hz), 5.64 (s,1H), 3.96 (dd, 1H, J1=3 Hz, J2=9 Hz), 3.82 (dd, 1H, J1=6 Hz, J2=9 Hz), 2.45 (s, 3 Hz), 0.99 (d, 3H, J=7 Hz), 0.53 (s, 3H).

EXAMPLE 2-9

Production of (3R)-3-[(1R,7aR)-octahydro-4-bromomethylene-7a-methyl-1H-inden-1-yl]butyronitrile

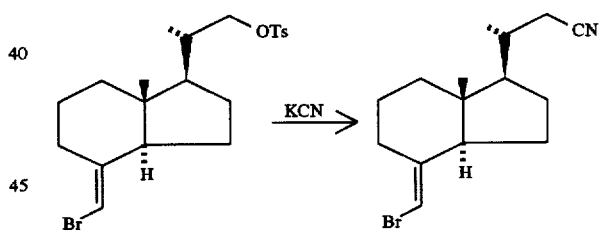

A 178 mg amount of (2R)-2-[(1R,7aR)-octahydro-4-bromomethylene-7a-methyl-1H-inden-1-yl]propylparatoluenes sulfonate was taken in a 50 ml eggplant-shaped flask, then 6 ml of dimethyl formamide was added for dissolution. To this was then charged 215 mg of KCN, then the solution was stirred in a 50° C. bath for 24 hours. To the reaction solution was added 50 ml of water, then extraction was performed with ether. The organic layer was washed with water and saturated saline, then was dried over anhydrous magnesium sulfate and the desiccant was filtered out. The solvent was distilled off under reduced pressure to obtain a crude product in an amount of 110 mg. This was purified by a silica gel column (Daiso gel, hexane/ethyl acetate=14/1) to obtain (3R)-3-[(1R,7aR)-octahydro-4-bromomethylene-7a-methyl-1H-inden-1-yl]butyronitrile in an amount of 84 mg (yield 69%).

¹H-NMR (CDCl₃, δ ppm)

5.67 (s, 1H), 2.86 to 2.91 (m, 1H), 2.21 to 2.35 (m, 2H), 1.18 (d, 3H, J=6 Hz), 0.59 (s, 3H).

EXAMPLE 2-10

Production of (3R)-3-[(1R,7aR)-octahydro-4-bromomethylene-7a-methyl-1H-inden-1-yl]butanol

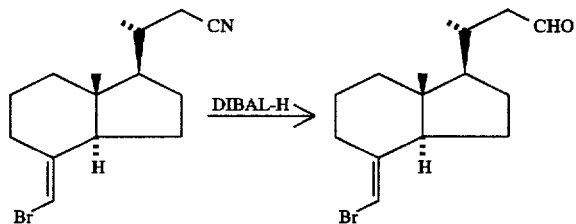

A 84 mg amount of (3R)-3-[(1R,7aR)-octahydro-4-bromomethylene-7a-methyl-1H-inden-1-yl]butyronitrile was taken in a 25 ml eggplant-shaped flask, then 5 ml of dried dichloromethane was then added to dissolve the same. The solution was cooled by a −70° C. bath, then 660 μl of a 1.5 M [(CH$_3$)$_2$CHCH$_2$]$_2$AlH/toluene solution was added dropwise. The solution was stirred at the same temperature for 1 hour, then 0.5 ml of a saturated aqueous solution of sodium sulfate, 0.3 ml of methanol, 0.5 ml of 2 N hydrochloric acid, and 15 ml of ethyl acetate were added and the solution stirred for 30 minutes. The reaction solution was filtered by Celite, then was washed by a saturated solution of ammonium chloride and saturated saline, then was dried over anhydrous magnesium sulfate and the desiccant filtered out. The solvent was distilled off under reduced pressure to obtain (3R)-3-[(1R,7aR)-octahydro-4-bromomethylene-7a-methyl-1H-inden-1-yl]butanol in an amount of 85 mg.

EXAMPLE 2-11

Production of (4S,6R)-6-[(1R,7aR)-octahydro-4-bromomethylene-7a-methyl-1H-inden-1-yl]-2-methoxycarbonyl-4-hydroxy-1-heptene and (4R,6R)-6-[(1R,7aR)-octahydro-4-bromomethylene-7a-methyl-1H-inden-1-yl]-2-methoxycarbonyl-4-hydroxy-1-heptene

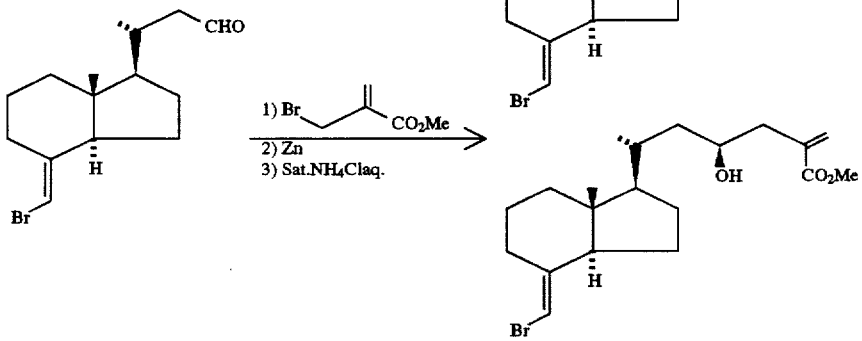

A 105 mg amount of (3R)-3-[(1R,7aR)-octahydro-4-bromomethylene-7a-methyl-1H-inden-1-yl]butanol was taken in a 50 ml eggplant-shaped flask, then 8 ml of dried tetrahydrofuran was then added to dissolve the same. The solution was cooled by an ice cooled bath, then 84 ml of methyl-2-bromomethylacrylate was added dropwise. Further, 35 mg of zinc powder and 10 ml of a saturated aqueous solution of ammonium chloride were added, then the solution was stirred at the same temperature for 1 hour. The reaction solution was extracted by ethyl acetate, the organic layer was washed with saturated saline, then was dried over anhydrous magnesium sulfate. The desiccant was filtered out, then the solvent was distilled off under reduced pressure to obtain a crude product in an amount of 166 mg. This was purified by a silica gel column (Merck gel, hexane/ethyl acetate=9/1) to obtain (4S,6R)-6-[(1R,7aR)-octahydro-4-bromomethylene-7a-methyl-1H-inden-1-yl]-2-methoxycarbonyl-4-hydroxy-1-heptene in an amount of 43 mg and (4R,6R)-6-[(1R,7aR)-octahydro-4-bromomethylene-7a-methyl-1H-inden-1-yl]-2-methoxycarbonyl-4-hydroxy-1-heptene in an amount of 55 mg.

$^1$H-NMR (CDCl$_3$, δ ppm)

6.269 (d, 1H, J=1 Hz), 5.66 (d, 2H, J=10 Hz), 3.77 (s, 3H), 2.84 to 2.93 (m, 1H), 2.65 to 2.72 (m, 1H), 2.13 to 2.27 (m, 1H), 1.02 (d, 3H, J=7 Hz), 0.58 (s, 3H), 6.249 (d, 1H, J=1 Hz), 5.65 (d, 2H, J=5 Hz), 3.77 (s, 3H), 2.84 to 2.90 (m, 1H), 2.53 to 2.55 (m, 1H), 2.31 to 2.39 (m, 1H), 0.97 (d, 3H, J=7 Hz), 0.59 (s, 3H)

EXAMPLE 2-12

Production of (5S)-5-{(2R)-2-[(1R,7aR)-octahydro-4-bromomethylene-7a-methyl-1H-inden-1-yl]propyl}-3-methylene-dehydro-2(3H)-furanon

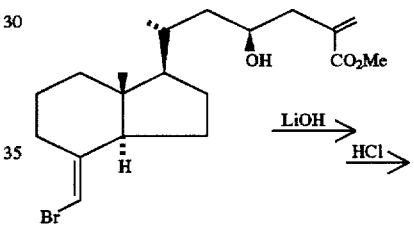

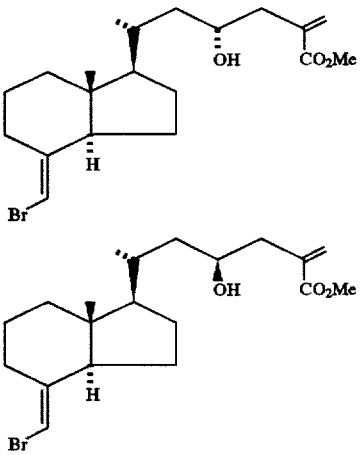

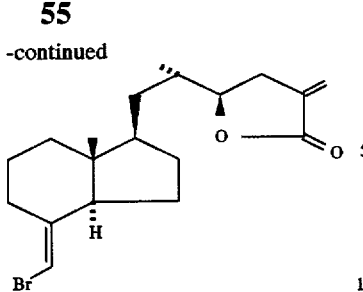

A 55 mg amount of (4S,6R)-6-[(1R,7aR)-octahydro-4-bromomethylene-7a-methyl-1H-inden-1-yl]-2-methoxycarbonyl-4-hydroxy-1-heptene was taken in a 50 ml eggplant-shaped flask, then 6 ml of tetrahydrofuran was added to dissolve the same. Further, 6 ml of water was added, the solution was cooled by an ice-cooled bath, 0.25 ml of 4 N lithium hydroxide was added dropwise, and the solution was stirred at the same temperature for 1 hour. Next, concentrated hydrochloric acid was added dropwise under the same temperature to adjust the pH to 2 and the solution was stirred at room temperature for 3 hours. To the reaction solution were added 10 ml of water and 100 ml of ethyl acetate for extraction. The organic layer was washed 3 times with water and 2 times with saturated saline, then was dried over anhydrous magnesium sulfate. The desiccant was filtered out and the solvent was distilled off under reduced pressure to obtain (5S)-5-{(2R)-2-[(1R,7aR)-octahydro-4-bromomethylene-7a-methyl-1H-inden-1-yl]propyl}-3-methylene-dehydro-2(3H)-furanon in an amount of 51 mg.

$^1$H-NMR (CDCl$_3$, δ ppm)

6.23 (t, 1H, J=3 Hz), 5.62 (t, 1H, J=2 Hz), 5.65 (d, H, J=2 Hz), 4.12 (dd, 1H, J1=7 Hz, J2=14 Hz), 3.00 to 3.11 (m, 1H), 2.85 to 2.9 (m, 1H), 2.47 to 2.57 (m, 1H), 1.03 (d, 3H, J=7 Hz), 0.58 (s, 3H).

EXAMPLE 2-13

Production of (5R)-5-{(2R)-2-[(1R,7aR)-octahydro-4-bromomethylene-7a-methyl-1H-inden-1-yl]propyl}-3-methylene-dehydro-2(3H)-furanon

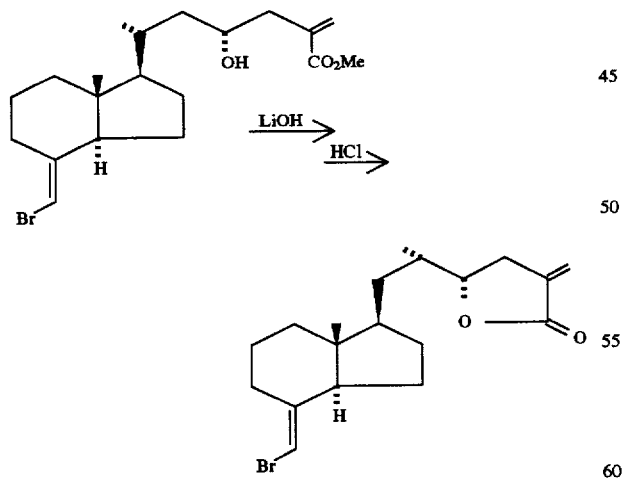

A 70 mg amount of (4R,6R)-6-[(1R,7aR)-octahydro-4-bromomethylene-7a-methyl-1H-inden-1-yl]-2-methoxycarbonyl-4-hydroxy-1-heptene was taken in a 50 ml eggplant-shaped flask, then 6 ml of tetrahydrofuran was added for dissolution. Further, 6 ml of water was added, the solution was cooled by an ice-cooled bath, 0.35 ml of 4 N lithium hydroxide was added dropwise, and the solution was stirred at the same temperature for 1 hour. Next, concentrated hydrochloric acid was added dropwise under the same temperature to adjust the pH to 2 and the solution was stirred at room temperature for 3 hours. To the reaction solution were added 10 ml of water and 100 ml of ethyl acetate for extraction. The organic layer was washed 3 times with water and 2 times with saturated saline, then was dried over anhydrous magnesium sulfate. The desiccant was filtered out and the solvent was distilled off under reduced pressure to obtain (5R)-5-{(2R)-2-[(1R,7aR)-octahydro-4-bromomethylene-7a-methyl-1H-inden-1-yl]propyl}-3-methylene-dehydro-2(3H)-furanon in an amount of 60 mg.

$^1$H-NMR (CDCl$_3$, δ ppm)

6.23 (t, 1H, J=3 Hz), 5.62 (t, 1H, J=2 Hz), 5.65 (d, 1H, J=2 Hz), 4.59 to 4.69 (m, 1H), 3.01 to 3.12 (m, 1H), 2.85 to 2.9 (m, 1H), 2.47 to 2.57 (m, 1H), 1.02 (d, 3H, J=7 Hz), 0.59 (s, 3H).

EXAMPLE 2-14

Production of 23(S),25(S)-1a-hydroxyvitamin D$_3$-26,23-lactone

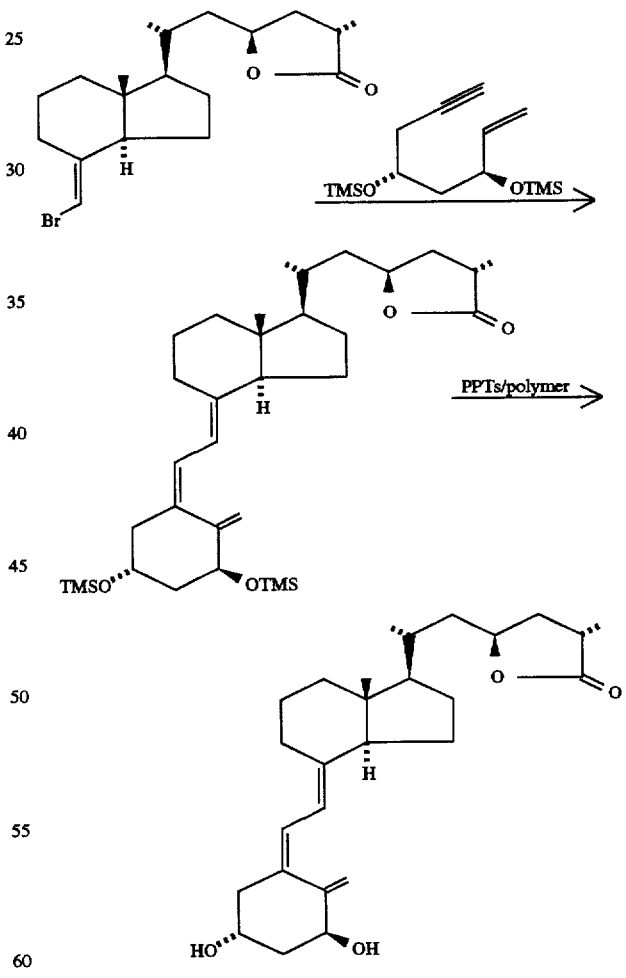

A 28 mg amount of triphenylphosphine was taken in a dried eggplant-shaped flask and deaerated. Thereafter, 19 mg of tris(dibenzylideneacetone)dipalladium chloroform was added, followed by further deaeration, then 6 ml of a mixed solvent of distilled toluene/diisopropylethylamine =1/1 was added under nitrogen and the solution was stirred at 50° C. for 20 minutes. Next, a solution of 65 mg of (3S,5S)-5-{(2R)-2-[(1R,7aR)-octahydro-4-bromomethylene-7a-methyl-1H-inden-1-yl]propyl}-3-methyldehydro-2(3H)-furanon and 60 mg of (3S),(5R)-3,5-bis(trimethylsilyloxy)-1-octen-7-yne dissolved in 3 ml of a mixed solvent of distilled toluene/diisopropylethylamine= 1/1 was added dropwise. This reaction solution was stirred at 100° C. for 1.5 hours. This was returned to room temperature, then the reaction solution was poured into 50 ml of ethyl acetate and 10 ml of a saturated aqueous solution of potassium hydrogensulfate for extraction. The organic layer was washed with a saturated aqueous solution of sodium hydrogencarbonate and saturated saline, then was dried over anhydrous sodium sulfate. The desiccant was filtered out and the solvent was distilled off under reduced pressure to obtain a crude product in an amount of 120 mg. This was purified by a silica gel column (Merck gel, hexane/ethyl acetate=14/1 to 9/1) to obtain 23(S),25(S)-1a-hydroxy-vitamin D$_3$-26,23-lactone-1,3-bistrimethylsilylether in an amount of 52 mg (yield 50%). This was placed in a 25 ml eggplant-shaped flask, then 5 ml of methanol was added to dissolve it. The solution was cooled by an ice-cooled bath, then 100 mg of polymer-bonded pyridinium toluene-4-sulfonate was added and the solution stirred for 15 hours. The reaction solution was filtered by Celite, then the solvent was distilled off under reduced pressure to obtain a crude product in an amount of 110 mg. This was purified by a silica gel column (Merck gel, hexane/ethyl acetate=2/1 to 1/1) to obtain 23(S),25(S)-1a-hydroxyvitamin D$_3$-26,23-lactone in an amount of 28 mg (yield 72%).

$^1$H-NMR (CDCl$_3$, δ ppm)

6.37 (d, 1H, J=11 Hz), 6.00 (d, 1H, J=11 Hz), 5.33 (s, 1H), 5.01 (s, 1H), 4.44 (br, 2H), 4.24 (br, 1H), 1.265 (d, 3H, J=8 Hz), 0.99 (d, 3H, J=6 Hz), 0.56 (s, 3H)

EXAMPLE 2-15

Production of 23(S)-1a-hydroxy-25,27-dehydro-vitamin D$_3$-26,23-lactone

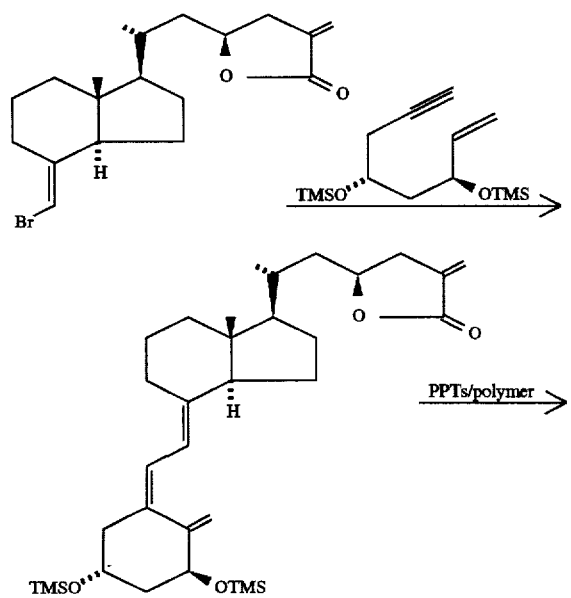

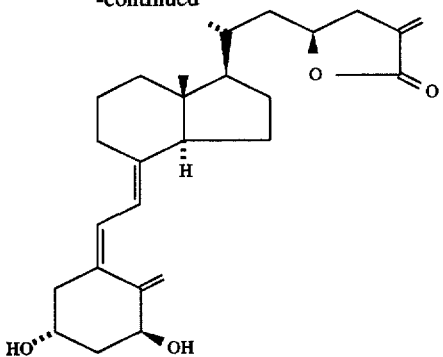

A 22 mg amount of triphenylphosphine was taken in a dried eggplant-shaped flask and then deaearated. Thereafter, 14 mg of tris(dibenzylideneacetone) dipalladium chloroform was added, followed by further deaeration, then 3 ml of a mixed solvent of distilled toluene/diisopropylethylamine= 1/1 was added under nitrogen and the solution was stirred at 50° C. for 20 minutes. Next, a solution of 51 mg of (5S)-5-{(2R)-2-[(1R,7aR)-octahydro-4-bromomethylene-7a-methyl-1H-inden-1-yl]propyl}-3-methylene-dehydro-2(3H)-furanon and 61 mg of (3S),(5R)-3,5-bis(trimethylsilyloxy)-1-octene-7-in dissolved in 4 ml of a mixed solvent of distilled toluene/diisopropylethylamine= 1/1 was added dropwise. This reaction solution was stirred at 100° C. for 1.5 hours, then was returned to room temperature. The reaction solution was poured into 50 ml of ethyl acetate and 10 ml of a saturated aqueous solution of potassium hydrogensulfate for extraction. The organic layer was washed with a saturated aqueous solution of sodium hydrogencarbonate and saturated saline, then was dried over anhydrous sodium sulfate. The desiccant was filtered out and the solvent was distilled off under reduced pressure to obtain a crude product in an amount of 120 mg. This was purified by a silica seppack (Waters, hexane/ethyl acetate=19/1 to 9/1) to obtain 23(S)-1a-hydroxy-25,27-dehydro-vitamin D$_3$-23,26-lactone-1a,3-bistrimethylsilylether in an amount of 46 mg (yield 50%). This was placed in a 25 ml eggplant-shaped flask, then 5 ml of methanol was added for dissolution. The solution was cooled by an ice-cooled bath, 50 mg of polymer-bonded pyridinium toluene-4-sulfonate was added, then the solution was stirred for 15 hours. The reaction solution was filtered by Celite, then the solvent was distilled off under reduced pressure to obtain a crude product in an amount of 110 mg. This was purified by a silica seppack (Waters, hexane/ethyl acetate=3/1 to 1/1) to obtain 23(S)-1a-hydroxy-25,27-dehydro-vitamin D$_3$-26,23-lactone in an amount of 12 mg (yield 40%).

$^1$H-NMR (CDCl$_3$, δ ppm)

6.37 (d, 1H, J=12 Hz), 6.22 (t, 1H, J=3 Hz), 6.00 (d, 1H, J=11 Hz), 5.62 (t, 1H, J=3 Hz), 5.323 (d, 1H, J=1 Hz), 5.00 (s, 1H), 4.59 (t, 1H, J=7 Hz), 4.43 to 4.54 (br, 1H), 4.22 to 4.24 (br, 1H), 2.99 to 3.11 (m, 1H), 2.79 to 2.85 (m, 1H), 2.48 to 2.61 (m, 2H), 2.28 to 2.35 (m, 1H), 1.03 (d, 3H, J=6 Hz), 0.56 (s, 3H)

EXAMPLE 2-16

Production of 23(R)-1a-hydroxy-25,27-dehydro-vitamin D$_3$-26,23-lactone

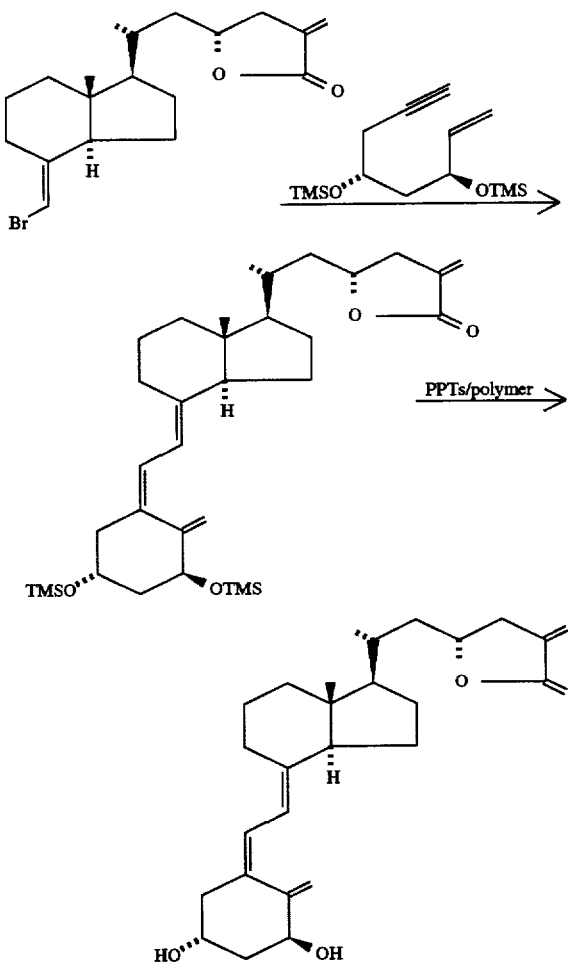

A 26 mg amount of triphenylphosphine was taken in a dried eggplant-shaped flask and deaerated. To this was further added 20 mg of tris(dibenzylideneacetone) dipalladium chloroform followed by further deaeration, then 3 ml of a mixed solvent of distilled toluene/ diisopropylethylamine=1/1 was added under nitrogen and the solution was stirred at 50° C. for 20 minutes. Next, a solution of 70 mg of (5R)-5-{(2R)-2-[(1R,7aR)-octahydro-4-bromomethylene-7a-methyl-1H-inden-1-yl]propyl}-3-methylene-dehydro-2(3H)-furanon and 84 mg of (3S),(5R)-3,5-bis(trimethylsilyloxy)-1-octen-7-yne dissolved in 4 ml of a mixed solvent of distilled toluene/ diisopropylethylamine=1/1 was added dropwise. This reaction solution was stirred at 100° C. for 1.5 hours, then was returned to room temperature. The reaction solution was poured into 50 ml of ethyl acetate and 10 ml of a saturated aqueous solution of potassium hydrogensulfate for extraction. The organic layer was washed with a saturated aqueous solution of sodium hydrogencarbonate and saturated saline, then was dried over anhydrous sodium sulfate. The desiccant was filtered out and the solvent was distilled off under reduced pressure to obtain a crude product in an amount of 190 mg. This was purified by a silica gel seppack (Waters, hexane/ethyl acetate=19/1 to 9/1) to obtain 23(R)-1a-hydroxy-25,27-dehydro-vitamin $D_3$-26,23-lactone-1a,3-bistrimethylsilylether in an amount of 50 mg (yield 40%). This was placed in a 25 ml eggplant-shaped flask, then 5 ml of methanol was added to dissolve it. The solution was cooled by an ice-cooled bath, then 100 mg of pyridinium toluene-4-sulfonate bonded to a polymer was added, then the solution was stirred for 15 hours. The reaction solution was filtered by Celite, then the solvent was distilled off under reduced pressure to obtain a crude product in an amount of 110 mg. This was purified by silica seppack (Waters, hexane/ethyl acetate =3/1 to 1/1) to obtain 23(R)-1a-hydroxy-25,27-dehydro-vitamin $D_3$-26,23-lactone in an amount of 14 mg (yield 43%).

$^1$H-NMR (CDCl$_3$, δ ppm)

6.37 (d, 1H, J=11 Hz), 6.225 (t, 1H, J=3 Hz), 6.00 (d, H, J=11 Hz), 5.62 (t, 1H, J=2 Hz), 5-33 (t, 1H, J=2 Hz), 5.00 (s, 1H), 4.59 to 4.69 (m, 1H), 4.41 to 4.45 (m, 1H), 4.21 to 4.25 (m, 1H), 3.01 to 3.10 (m, 1H), 2–79 to 2.85 (m, 1H), 2.47 to 2.58 (m, 2H), 2.28 to 2.35 (m, 1H), 1.02 (d, 3H, J=6 Hz), 0.58 (s, 3H)

REFERENCE EXAMPLE 3-1

Production of (2R)-2-[(1R, 7aR)-octahydro-4-trimethylsilyloxy-7a-methyl-1H-inden-1-yl]propanol

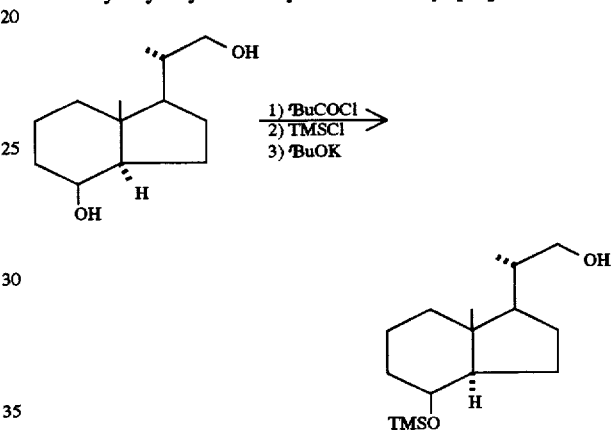

A 10.78 g amount of (2R)-2-[(1R, 7aR)(4E)-octahydro-4-hydroxy-7 a-methyl-1H-inden-1-yl]propanol dissolved in 80 ml of pyridine was added to a 100 ml eggplant-shaped flask and the solution was stirred under ice-cooling. Thereafter, 6.57 ml of pivaloyl chloride was added, then the solution was stirred over night.

To this reaction solution was added 150 ml of water. The solution was then extracted 3 times by 200 ml of ether. The organic layer was washed 2 times each by a saturated aqueous solution of potassium hydrogensulfate, a saturated aqueous solution of sodium bicarbonate, and saturated saline, then was dried over anhydrous magnesium sulfate. The desiccant was filtered out and the solvent was distilled off under reduced pressure to obtain a crude product in an amount of 14.7 g. This was placed in a 200 ml eggplant-shaped flask, 10.9 g of imidazole was added, 60 ml of dried dichloromethane was added, and the solution was stirred under ice-cooling. To this was added 10.2 ml of trimethylsilyl chloride, then the solution was stirred over night at room temperature. The reaction solution was poured in 300 ml of ethyl acetate and 100 ml of water for extraction. The organic layer was washed 2 times each by a saturated aqueous solution of potassium hydrogensulfate, a saturated aqueous solution of sodium bicarbonate, and saturated saline, then was dried over anhydrous magnesium sulfate. The desiccant was filtered out and the solvent was distilled off under reduced pressure to obtain a crude product in an amount of 18.11 g. A 17.2 g amount of t-butoxy potassium was placed in a 1-liter eggplant-shaped flask, then 440 ml of ether was added and the solution was stirred under ice-cooling. A 2.1 ml amount of water was added, then a solution of 8.11 g of the above residue dissolved in 120 ml of ether was added and the solution was stirred over night at room temperature. A 200 ml amount of water was poured into the reaction solution for separation, then extraction was performed with 500 ml of ether. The organic layer was washed 2 times with saturated saline, then was dried over anhydrous magnesium sulfate. The desiccant was filtered out and the solvent was distilled off under reduced pressure to obtain a crude product in an amount of 15.2 g. This was purified by a silica gel column (IR-60, 1 kg, hexane/ethyl acetate=19/1 to 6/1) to obtain (2R)-2-[(1R, 7aR)-octahydro-4-trimethylsilyloxy-7a-methyl-1H-inden-1-yl]propanol in an amount of 12.6 g (yield 87%).

$^1$H-NMR (CDCl$_3$, δ ppm)

3.95 (d, 1H, J=3 Hz), 3.58 (m, 1H), 3.31 (m, 1H), 1.00 to 2.00 (m, 14H), 0.96 (d, 3H, J=8 Hz), 0.85 (s, 3H), 0.03 (s, 9H)

REFERENCE EXAMPLE 3-2

Production of (2R)-2-[(1R,7aR)-octahydro-4-trimethylsilyloxy-7a-methyl-1H-inden-1-yl]propanal

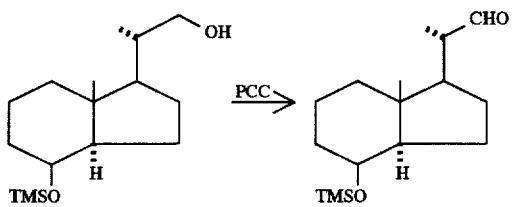

A 427 mg amount of cellite, 37 mg of sodium acetate, and 444 mg of pyridinum chlorochromate were placed in a 50 ml eggplant-shaped flask, then 10 ml of dichloromethane was added and the solution stirred. Thereafter, a dichloromethane solution (3 ml) of 426 mg of (2R)-2-[(1R, 7aR)-octahydro-4-trimethylsilyloxy-7a-methyl-1H-inden-1-yl]propanol was added, then the solution was stirred at room temperature for 3.5 hours.

The reaction solution was filtered by Celite, then was concentrated and the obtained residue was purified by a silica gel column to obtain (2R)-2-[(1R, 7aR)-octahydro-4-trimethylsilyloxy-7a-methyl-1H-inden-1-yl]propanal in an amount of 254 mg (yield 60%).

$^1$H-NMR (CDCl$_3$, δ ppm)

9.56 (d, 1H J=3 Hz), 3.90 to 4.00 (m, 1H), 2.20 to 2.50 (m, 1H), 1.00 to 2.00 (m, 12H), 0.92 (d, 3H, J=6.3 Hz), 0.91 (s, 3H), 0.05 (s, 9H)

REFERENCE EXAMPLE 3-3

Production of methyl(4R)-4-[(1R,7aR)-octahydro-4-trimethylsilyloxy-7a-methyl-1H-inden-1-yl]-2-pentenoate

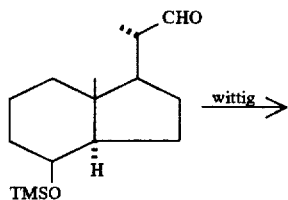

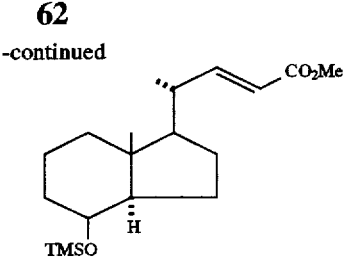

A 3.27 g amount of (2R)-2-[(1R,7aR)-octahydro-4-trimethylsilyloxy-7a-methyl-1H-inden-1-yl]propanal and 11.9 g of methyl(triphenylphosphoranilidene)acetate were placed in a 200 ml eggplant-shaped flask, 70 ml of toluene was added, and the solution was stirred at 80° C. over night. This was cooled to room temperature, then 100 ml of hexane was added, the precipitated deposit was filtered out, and the filtrate was concentrated under reduced pressure to obtain a crude product in an amount of 4.1 g. This was purified by a silica gel column (IR-60, 200 g, hexane/ethyl acetate=40/1) to obtain methyl(4R)-4-[(1R, 7aR)-octahydro-4-trimethylsilyloxy-7a-methyl-1H-inden-1-yl]-2-pentenoate in an amount of 3.82 g (yield 96%).

$^1$H-NMR (CDCl$_3$, δ ppm)

6.83 (dd, 1H, J=9.9 & 16 Hz), 5.73 (d, 1H, 16 Hz), 3.99 (brs, 1H), 3.72 (s, 3H), 2.10 to 2.30 (m, 2H), 1.00 to 2.00 (m, 15H), 1.00 (d, 3H, J=6.6 Hz), 0.92 (s, 3H), 0.05 (s, 9H)

REFERENCE EXAMPLE 3-4

Production of (4R)-4-[(1R,7aR)-octahydro-4-trimethylsilyloxy-7a-methyl-1H-inden-1-yl]-2-penten-1-ol

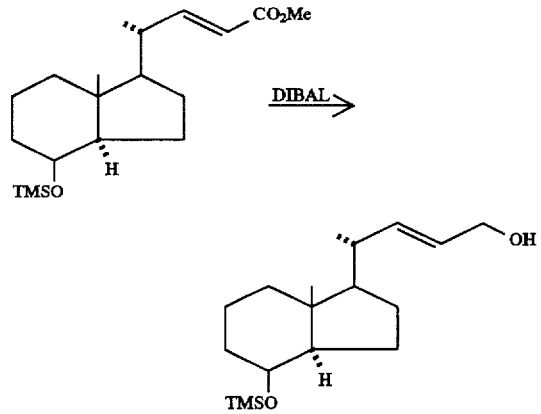

A 3.66 g amount of methyl(4R)-4-[(1R,7aR)-octahydro-4-trimethylsilyloxy-7a-methyl-1H-inden-1-yl]-2-pentenoate was placed in a 500 ml eggplant-shaped flask, and 100 ml of hexane and 40 ml of toluene were then added to dissolve it. The solution was cooled to −95° C., then 12.2 ml of diisobutylaluminum hydride was slowly added and the solution stirred at the same temperature for 1 hour. Next, a further 24 ml of diisobutylaluminum hydride was added, followed by stirring for 2 hours. The consumption of the material was confirmed by thin layer chromatography, then the excess reducing agent was broken down by methanol and a saturated aqueous solution of sodium sulfate and then 300 ml of ethyl acetate and 80 ml of a saturated aqueous solution of ammonia chloride were added for separation. Extraction was performed from the aqueous layer by 100 ml of ethyl acetate, then the organic layer was washed with saturated saline and was dried by anhydrous magnesium sulfate. The desiccant was filtered out, then the filtrate was concentrated under reduced pressure to obtain a crude product in an amount of 3.61 g. This was purified by a silica column (hexane/ethyl acetate=19/1 to 4/1) to obtain (4R)-4-[(1R, 7aR)-octahydro-4-trimethylsilyloxy-7a-methyl-1H-inden-1-y l]-2-penten-1-ol in an amount of 3.31 g (98%).

$^1$H-NMR (CDCl$_3$, δ ppm)

5.5 to 5.6 (m, 2H), 4.07 (brd, 2H), 3.99 (brs, 1H), 1.0 to 2.2 (m, 14H), 1.00 (d, J=6.6 Hz, 3H), 0.90 (s, 3H), 0.05 (s, 9H)

REFERENCE EXAMPLE 3-5

Production of (4R)-4-[(1R,7aR)-octahydro-4-trimethylsilyloxy-7a-methyl-1H-inden-1-yl]-2-penten-1-al

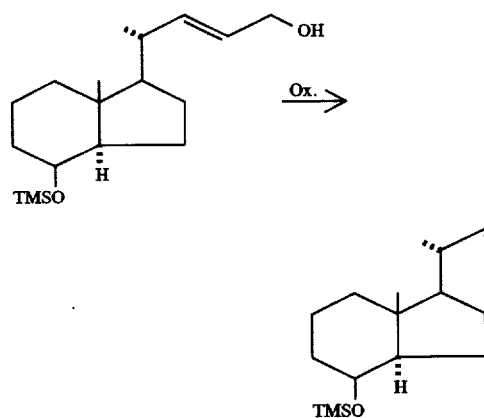

A 1.34 g amount of (4R)-4-[(1R,7aR)-octahydro-4-trimethylsilyloxy-7a-methyl-1H-inden-1-yl]-2-penten-1-ol and 760 mg of N-methylmorpholine-N-oxide were placed in a 100 ml eggplant-shaped flask, then were dissolved in 30 ml of acetone. Thereafter, RuCl$_2$ (PPh$_3$)$_3$ was added, then the solution was stirred at room temperature for 1.5 hours.

To the reaction solution were added 50 ml of hexane and 1.5 g of Celite, the solution was stirred for 15 minutes, then was filtered and the solvent distilled off under reduced pressure. The residue was purified by a silica gel column (hexane/ethyl acetate=50/1 to 30/1) to obtain (4R)-4-[(1R, 7aR)-octahydro-4-trimethylsilyloxy-7a-methyl-1H-inden-1-yl]-2-penten-1-al in an amount of 0.854 g (yield 86%).

$^1$H-NMR (CDCl$_3$, δ ppm)

9.51 (d, J=7.9 Hz, 1H), 6.71 (dd, J=8.6 & 16 Hz, 1H), 6.04 (dd, J=7.9 & 16 Hz, 1H), 4.01 (brs, 1H), 2.3 to 2.4 (m, 1H), 1.1 to 2.2 (m, 12H), 1.11 (d, J=6.6 Hz, 3H), 0.94 (s, 3H), 0.05 (s, 9H)

REFERENCE EXAMPLE 3-6

Production of (5R,2S)-5-{(4R)-4-[(1R,7aR)-octahydro-4-trimethylsilyloxy-7a-methyl-1H-inden-1-yl]-1-hydroxy-2-penten-1-yl}-5-methyl-2-t-butyl-1, 3-dioxolan-4-one

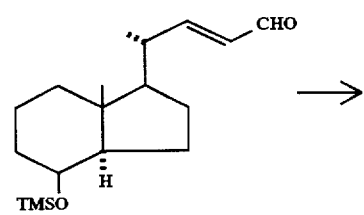

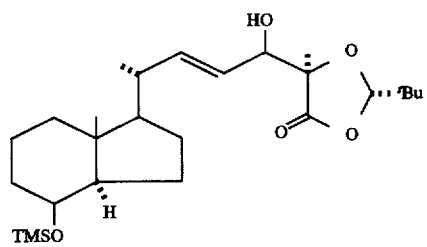

A 15 ml amount of tetrahydrofuran and 910 μl of diisopropylamine were placed in a 100 ml eggplant-shaped flask, then the solution was cooled to −78° C. Thereafter, 2.52 ml of n-BuLi was added, then the solution was stirred at the same temperature for 15 minutes, was stirred at 0° C. for 30 minutes, then was again cooled to −78° C. and was stirred for 15 minutes. To this was added a tetrahydrofuran solution (6 ml) of 627 mg of (5S,2S)-5-methyl-2-t-butyl-1,3-dioxolan-4-one. The solution was stirred at the same temperature for 15 minutes, then a tetrahydrofuran solution (8 ml) of 854 mg of (4R)-4-[(1R, 7aR)-octahydro-4-trimethylsilyloxy-7a-methyl-1H-inden-1-yl]-2-penten-1-al was added and the solution was reacted at −78° C. for 30 minutes.

To the reaction solution were added a saturated aqueous solution of ammonium chloride and ether for separation, then extraction was performed from the aqueous layer by ethyl acetate. The organic layer was washed with saturated saline, then was dried over anhydrous magnesium sulfate and filtered, then the solvent was distilled off under reduced pressure. The residue was purified by a silica gel column (hexane/ethyl acetate=15/1 to 4/1) to obtain (5R,2S)-5-{(4R)-4-[(1R,7aR)-octahydro-4-trimethylsilyloxy-7a-methyl-1H-inden-1-yl]-1-hydroxy-2-penten-1-yl}-5-methyl-2t-butyl-1,3-dioxolan-4-one in an amount of 1.24 g (yield 96%).

$^1$H-NMR (CDCl$_3$, δ ppm)

5.0 to 5.7 (m, 3H), 4.1 to 4.2 (m, 1H), 3.99 (brs, H), 1.0 to 2.2 (m, 17H), 0.88 to 1.0 (m, 15H), 0.04 (s,

REFERENCE EXAMPLE 3-7

Production of (5R,2S)-5-{(4R)-4-[(1R,7aR)-octahydro-4-trimethylsilyloxy-7a-methyl-1H-inden-1-yl]-1-methoxycarbonyloxy-2-penten-1-yl}-5-methyl-2-t-butyl-1, 3-dioxolan-4-one

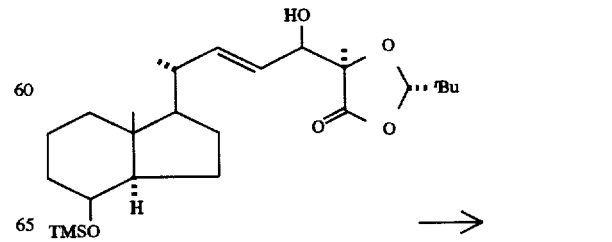

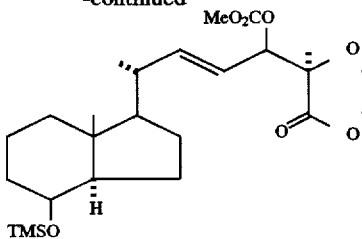

A 1.24 g amount of (5R,2S)-5-{(4R)-4-[(1R, 7aR)-octahydro-4-trimethylsilyloxy-7a-methyl-1H-inden-1-yl]-1-hydroxy-2-penten-1-yl}-5-methyl-2-t-butyl-1,3-dioxolan-4-one and 1.0 g of 4-dimethylaminopyridine were dissolved in 15 ml of dichloromethane in a 50 ml eggplant-shaped flask. The solution was stirred under ice-cooling while slowly adding 315 µl of methyl chloroformate, then was stirred at the same temperature for 15 minutes and at room temperature for 1.5 hours. A 100 ml amount of ethyl acetate and 30 ml of water were added for separation, and extraction was performed from the aqueous layer by 50 ml of ethyl acetate. The organic layer was washed by a saturated aqueous solution of potassium hydrogensulfate, a saturated aqueous solution of sodium hydrogencarbonate, and saturated saline and was dried over anhydrous magnesium sulfate. The desiccant was filtered out, then the filtrate was concentrated under reduced pressure to obtain a crude product in an amount of 3.61 g. This was purified by a silica column (hexane/ethyl acetate=19/1 to 9/1) to obtain (5R,2S)-5-{(4R)-4-[(1R,7aR)-octahydro-4-trimethylsilyloxy-7a-methyl-1H-inden-1-yl]-1-methoxycarbonyloxy-2-penten-1-yl}-5-methyl-2-t-butyl-1,3-dioxolan-4-one in an amount of 1.388 g (98%).

$^1$H-NMR (CDCl$_3$, δ ppm)

5.3 to 5.9 (m, 2H), 5.25 (s, 1H), 5.11 (d, J=7 Hz, 1H), 3.99 (brs, 1H), 3.78 & 3.75 (s, 3H), 1.0 to 2.2 (m, 16H), 0.8 to 1.0 (m, 15H), 0.05 (s, 9H)

EXAMPLE 3-1

Production of (5R,2S)-5-{(4R)-4-[(1R, 7aR)-octahydro-4-trimethylsilyloxy-7a-methyl-1H-inden-t-yl]pentyl}-5-methyl-2-t-butyl-1,3-dioxolan-4-one

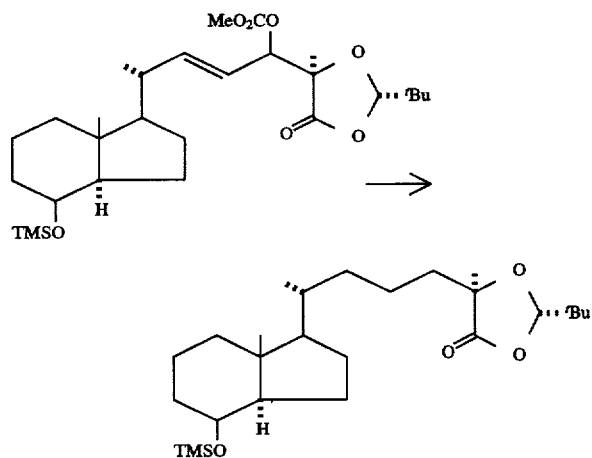

Pd(OAc)$_2$ was placed in a 100 ml eggplant-shaped flask and dissolved in 50 ml of tetrahydrofuran. Further, 0.54 ml of n-Bu$_3$P was added, the solution stirred at room temperature for 15 minutes, 681 mg of ammonium formate was added, a tetrahydrofuran solution (10 ml) of 1.38 g of (5R,2S)-5-{(4R)-4-[(1R,7aR)-octahydro-4-trimethylsilyloxy-7a-methyl-1H-inden-1-yl]-1-methoxycarbonyloxy-2-penten-1-yl}-5-methyl-2-t-butyl-1,3-dioxolan-4-one was added, and the solution was reacted at 40° C. over night.

To the reaction solution were added 50 ml of hexane and 50 ml of ether 50 ml, the solution was filtered, then the solvent was distilled off under reduced pressure to obtain 920.8 mg of any oily substance. This was subjected to the following reaction divided into two times without purification. A 398 mg amount of the oily substance was dissolved in ethyl acetate, 10% Pd/C was placed in Microspatel Cup, then this was stirred over night under a flow of hydrogen. The solution was filtered, then concentrated to obtain a crude product in an amount of 0.43 g. A 520 mg amount of the remaining oily substance was treated in the same way to obtain 0.494 g. These were combined and purified to obtain 0.867 mg of (5R,2S)-5-{(4R)-4-[(1R,7aR)-octahydro-4-trimethylsilyloxy-7a-methyl-1H-inden-1-yl]pentyl}-5-methyl-2-t-butyl-1,3-dioxolan-4-one (yield 73%).

$^1$H-NMR (CDCl$_3$, δ ppm)

5.19 (s, 1H), 3.99 (brs, 1H), 1.41 (s, 3H), 1.0 to 2.0 (m, 19H), 0.96 (s, 9H), 0.88 (d-like, 3H), 0.87 (s, 3H), 0.05 (s, 9H)

EXAMPLE 3-2

Production of (5R,2S)-5-{(4R)-4-[(1R,7aR)-octahydro-4-hydroxy-7a-methyl-1H-inden-1-yl]pentyl}-5-methyl-2-t-butyl-1,3-dioxolan-4-one

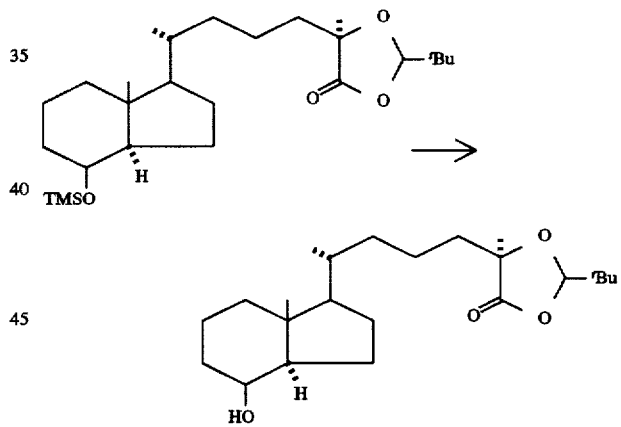

A 913 mg amount of (5R,2S)-5-{(4R)-4-[(1R,7aR)-octahydro-4-trimethylsilyloxy-7a-methyl-1H-inden-1-yl]pentyl}-5-methyl-2-t-butyl-1,3-dioxolan-4-one was placed in a 100 ml eggplant-shaped flask and dissolved in 10 ml of tetrahydrofuran. A tetrahydrofuran solution (1 M, 2.5 ml) of tetrabutylammonium fluoride was added under ice cooling, then the solution was stirred at the same temperature for 15 minutes, was returned to room temperature, then was stirred for 1 hour. Thereafter, 100 ml of ether and 20 ml of water for separation were added, extraction was performed from the aqueous layer by ether, then the organic layer was washed with saline and then was dried over anhydrous magnesium sulfate. Further, this was concentrated, then purified by a silica column (hexane/ethyl acetate=9/1 to 6/1) to obtain (5R,2S)-5-{(4R)-4-[(1R,7aR)-octahydro-4-hydroxy-7a-methyl-1H-inden-1-yl]pentyl}-5-methyl-2-t-butyl-1,3-dioxolan-4-one in an amount of 764 mg (99%).

¹H-NMR (CDCl₃, δ ppm)

5.19 (s, 1H), 4.08 (brs, 1H), 1.44 (s, 3H), 1.0 to 2.1 (m, 20H), 0.96 (s, 9H), 0.93 (s, 3H), 0.90 (d, 3H, J=6.6 Hz)

EXAMPLE 3-3

Production of (5R,2S)-5-{(4R)-4-[(1R,7aR)-octahydro-4-oxo-7a-methyl-1H-inden-1-yl]pentyl}-5-methyl-2-t-butyl-1,3-dioxolan-4-one

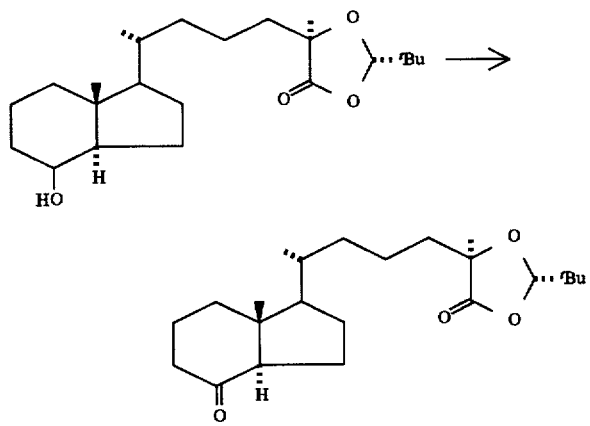

A 384 mg amount of (5R,2S)-5-{(4R)-4-[(1R,7aR)-octahydro-4-hydroxy-7a-methyl-1H-inden-1-yl]pentyl}-5-methyl-2-t-butyl-1,3-dioxolan-4-one and 74 mg of RuH₂(PPh₃)₄ were placed in a 100 ml two-necked flask and dissolved in 20 ml of toluene. Thereafter, 8 ml of methylallyl carbonate was added, then the solution was stirred at 100° C. over night.

The reaction solution was allowed to cool, then the precipitate was filtered out, the solvent was distilled off under reduced pressure, and the residue was purified by a silica gel column (hexane/ethyl acetate=19/1 to 10/1) to obtain (5R,2S)-5-{(4R)-4-[(1R,7aR)-octahydro-4-oxo-7a-methyl-1H-inden-1-yl]pentyl}-5-methyl-2-t-butyl-1,3-dioxolan-4-one in an amount of 370 mg (yield 96%).

¹H-NMR (CDCl₃, δ ppm)

5.19 (s, 1H), 1.44 (s, 3H), 1.0 to 2.0 (m, 19H), 0.96 (brs, 12H), 0.64 (s, 3H)

EXAMPLE 3-4

Production of (5R,2S)-5-{(4R)-4-[(1R,7aR)(4E)-octahydro-4-bromomethylene-7a-methyl-1H-inden-1-yl]pentyl}-5-methyl-2-t-butyl-1,3-dioxolan-4-one

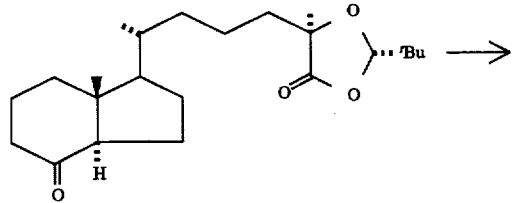

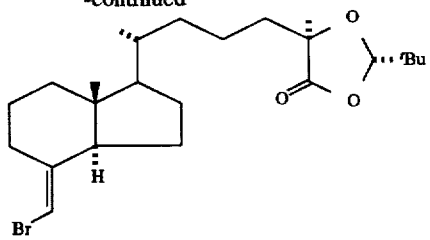

A 5.19 g amount of PPh₃CH2Br•Br was placed in a 100 ml eggplant-shaped flask, was suspended in 30 ml of tetrahydrofuran, and stirred at −78° C. Thereafter, 11.3 ml of TMS₂NNa (1 M-THF) was added, then the solution was stirred at room temperature for 1 hour and, then, was further added a tetrahydrofuran solution (10 ml) of 449 mg of (5R,2S)-5-{(4R)-4-[(1R,7aR)-octahydro-4-oxo-7a-methyl-1H-inden-1-yl]pentyl}-5-methyl-2-t-butyl-1,3-dioxolan-4-one, then the solution was returned to room temperature and stirred for 30 minutes. To the reaction solution was added ether, the solution was stirred at room temperature, then the precipitate was filtered out and the solvent was distilled off under reduced pressure. The result was purified by a silica gel column (hexane/ethyl acetate=100/0 to 100/1 to 4/1) to obtain (5R, 2S)-5-{(4R)-4-[(1R,7aR)(4E)-octahydro-4-bromomethylene-7a-methyl-1H-inden-1-yl]pentyl}-5-methyl-2-t-butyl-1,3-dioxolan-4-one in an amount of 242 mg (yield 45%).

¹H-NMR (CDCl₃, δ ppm)

5.65 (s, 1H), 5.19 (s, 1H), 2.80 to 3.00 (m, 1H), 1.44 (s, 3H), 1.0 to 2.1 (m, 18H), 0.96 (s, 9H), 0.93 (d, 3H J=6 Hz), 0.56 (s, 3H)

EXAMPLE 3-5

Production of 25,26,27-trinol-1α-hydroxy-24-{(5R,2S)-5-methyl-2-t-butyl-1,3-dioxolan-4-on-5-yl}-vitamin D₃-1α,3-bistrimethylsilylether

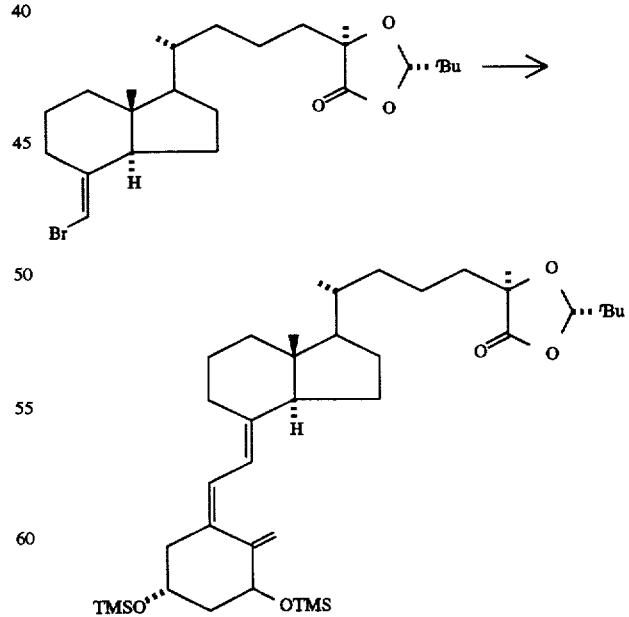

A 17 mg amount of Pd₂(dibenzylideneacetone)₃•CHCl₃ and 51.7 mg of PPh₃ were placed in a 100 ml two-neck eggplant-shaped flask and dissolved in 9 ml of toluene and 9 ml of diisopropylethylamine. Thereafter, 141.5 mg of (5R,2S)-5-{(4R)-4-[(1R,7aR)(4E)-octahydro-4-bromomethylene-7a-methyl-1H-inden-1-yl]pentyl}-5-methyl-2-t-butyl-1,3-dioxolan-4-one dissolved in 2 ml of toluene and 2 ml of diisopropylethylamine was added, then the solution was heated and refluxed for 1.5 hours. The solution was allowed to cool, then 20 ml of hexane was added, the precipitate filtered out, and the filtrate was washed with a saturated solution of potassium hydrogensulfate and saturated saline, then was dried over anhydrous magnesium sulfate, filtered and concentrated. The obtained residue was purified by a silica gel column (hexane/ethyl acetate=100/1 to 30/1) to obtain 25,26,27-trinol-1a-hydroxy-24-{(5R,2S)-5-methyl-2-t-butyl-1,3-dioxolan-4-on-5-yl}-vitamin $D_3$-1a,3-bistrimethylsilylether in an amount of 118.5 mg (yield 58%).

$^1$H-NMR (CDCl$_3$, δ ppm)

6.27 (d, 1H, J=12 Hz), 6.04 (d, 1H, J=12 Hz), 5.19 (brs, 2H), 4.90 (brs, 1H), 4.30 to 4.40 (m, 1H), 4.15 to 4.25 (m, 1H), 1.0 to 2.9 (m, 23H), 1.43 (s, 3H), 0.96 (s, 9H), 0.93 (d, 3H, J=6 Hz), 0.54 (s, 3H), 0.12 (s, 18H)

EXAMPLE 3-6

Production of 25,26,27-trinol-1a-hydroxy-24-{(5R,2S)-5-methyl-2-t-butyl-1,3-dioxolan-4-on-5-yl}vitamin $D_3$

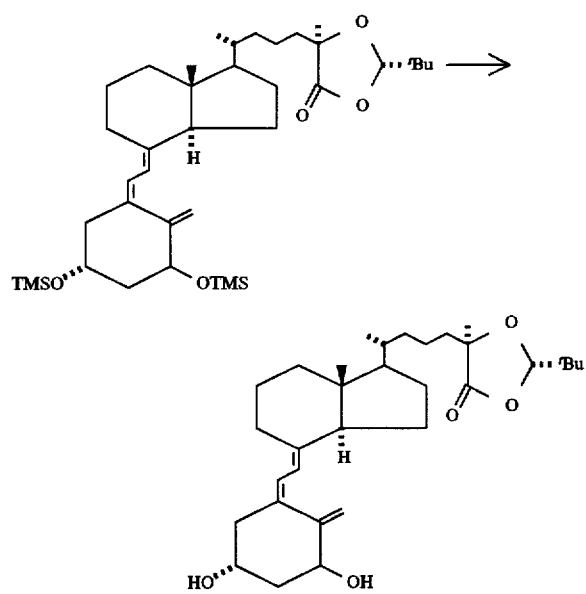

A 112 mg amount of 25,26,27-trinol-1a-hydroxy-24-{(5R, 2S)-5-methyl-2-t-butyl-1,3-dioxolan-4-on-5-yl}-vitamin $D_3$-1a,3-bistrimethylsilylether was placed in a 50 ml eggplant-shaped flask and dissolved in 30 ml of methanol, then 50 mg of pyridinium-para-toluene sulfonate was added and the solution stirred at room temperature for 2 hours. The reaction solution was filtered, the filtrate was concentrated, and the obtained residue was purified by a silica gel column (hexane/ethyl acetate=1/1) to obtain 25,26,27-trinol-1a-hydroxy-24-{(5R,2S)-5-methyl-2-t-butyl-1,3-dioxolan-4-on-5-yl}-vitamin D3 in an amount of 40.2 mg (yield 46%).

$^1$H-NMR (CDCl$_3$, δ ppm)

6.38 (d, 1H, J=11 Hz), 6.01 (d, 1H, J=11 Hz), 5.32 (s, 1H), 5.19 (s, 1H), 5.00 (s, 1H), 4.40 to 4.50 (m, 1H), 4.20 to 4.30 (m, 1H), 1.0 to 2.9 (m, 25H), 1.44 (s, 3H), 0.96 (s, 9H), 0.93 (d, 3H, J=6 Hz), 0.54 (s, 3H)

EXAMPLE 3-7

Production of 1a,25-dihydroxyvitamin $D_3$-26-carboxylic acid methylester

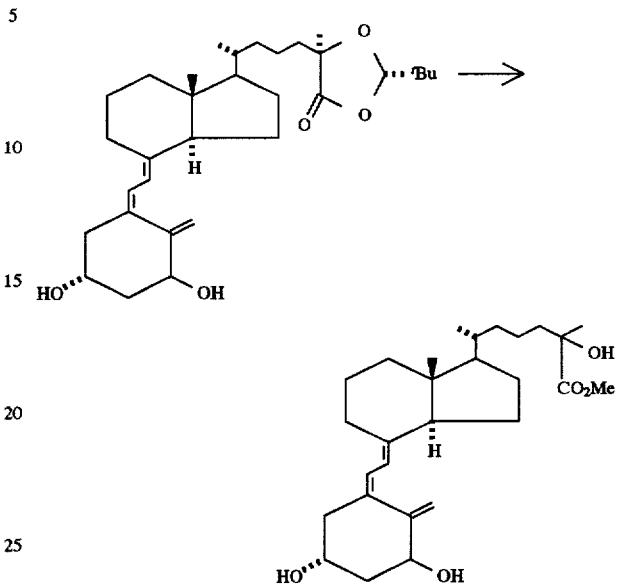

A 40 mg amount of 25,26,27-trinol-1a-hydroxy-24-{(5R, 2S)-5-methyl-2-t-butyl-1,3-dioxolan-4-on-5-yl}-vitamin $D_3$ was placed in a 50 ml eggplant-shaped flask and dissolved in 5 ml of methanol, then 4 N lithium hydroxide was added and the solution was stirred at room temperature for 1 hour. The reaction solution was neutralized, tetrahydrofuran was added, the solution was washed five times by saturated saline, then was dried over anhydrous magnesium sulfate. The solution was filtered and concentrated, the obtained residue was dissolved in benzene/methanol (4/1), 0.8 ml of a hexane solution (about 10%) of trimethylsilyldiazomethane was added, and the solution was stirred at room temperature for 1 hour. The excess reagent was broken down by formic acid, then the solution was concentrated. The obtained residue was purified by a silica gel column (hexane/ethyl acetate=⅔ to ⅓) to obtain 1a,25-dihydroxyvitamin $D_3$-26-carboxylic acid methylester in an amount of 24.4 mg (yield 68%).

$^1$H-NMR (CDCl$_3$, δ ppm)

6.38 (d, 1H, J=11 Hz), 6.01 (d, 1H, J=11 Hz), 5.33 (s, 1H), 5.00 (s, 1H), 4.35 to 4.45 (m, 1H), 4.20 to 4.30 (m, 1H), 3.79 (s, 3H), 1.0 to 3.1 (m, 26H), 1.40 (s, 3H), 0.90 (d, 3H, J=6 Hz), 0.53 (s, 3H)

EXAMPLE 4-1

Production of (2R)-2-[(1R,7aR)-octahydro-4-trimethylsilyloxy-7a-methyl-1H-inden-1-yl]-propanol

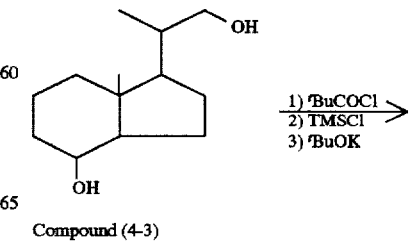

Compound (4-3)

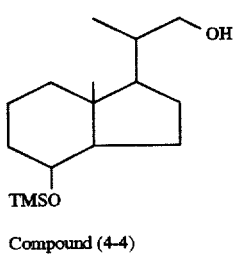

Compound (4-4)

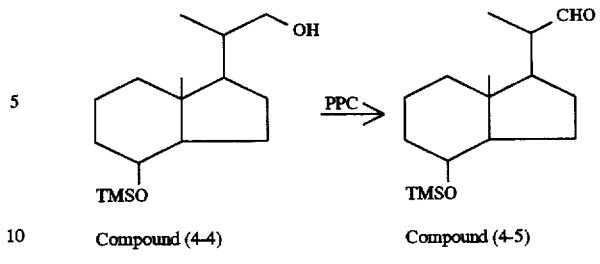

Compound (4-4)　　　Compound (4-5)

A 10.78 g amount of the compound (4-3), (2R)-2-[(1R, 7aR)(4E)-octahydro-4-hydroxy-7a-methyl-1-H-inden-1-yl]-propanol was dissolved in 80 ml of pyridine in a 100 ml eggplant-shaped flask, then was stirred under ice cooling. To this was added 6.57 ml of pivaloyl chloride, then the solution was stirred over night.

Into the reaction solution was placed 150 ml of water, then extraction was performed 3 times by 200 ml of ether. The organic layer was washed 2 times each with a saturated aqueous solution of potassium hydrogensulfate, saturated aqueous solution of sodium bicarbonate, and saturated saline, was dried over anhydrous magnesium sulfate, the desiccant was filtered out, and the solvent was distilled off under reduced pressure to obtain a crude product in an amount of 14.7 g. This was placed in a 200 ml eggplant-shaped flask, 10.9 g of imidazole was added, then 60 ml of dried dichloromethane was further added and the solution stirred under ice-cooling. To this was added 10.2 ml of trimethylsilyl chloride and the solution was stirred at room temperature over night. The reaction solution was poured into 300 ml of methyl acetate and 100 ml of water for extraction. The organic layer was washed two times by each of a saturated aqueous solution of potassium hydrogensulfate, saturated aqueous solution of sodium bicarbonate, and saturated saline, then was dried over anhydrous magnesium sulfate. The desiccant was filtered out and the solvent was distilled off under reduced pressure to obtain a crude product in an amount of 18.11 g. A 17.2 g amount of t-butoxy potassium was placed in a 1-liter eggplant-shaped flask, 440 ml of ether was added, and the solution was stirred under ice-cooling. A 2.1 ml amount of water was added, then a solution comprised of 18.11 g of the above residue dissolved in 120 ml of ether was added and the solution was stirred at room temperature over night. A 200 ml amount of water was poured into the reaction solution for separation, then extraction was performed by 500 ml of ether. The organic layer was washed 2 times with saturated saline, then was dried over anhydrous magnesium sulfate. The desiccant was filtered out and the solvent was distilled off under reduced pressure to obtain a crude product in an amount of 15.2 g. This was purified by a silica gel column (IR-60, 1 kg, hexane/ethyl acetate =19/1 to 6/1) to obtain the desired product (4-4), (2R)-2-[(1R,7aR)-octahydro-4-trimethylsilyloxy-7a-methyl-1H-inden-1-yl]-propanol in an amount of 12.6 g (yield 87%).

$^1$H-NMR (CDCl$_3$, δ ppm)

3.95 (d, 1H, J=3 Hz), 3.58 (m, 1H), 3.31 (m, 1H), 1.00 to 2.00 (m, 14H), 0.965 (d, 3H, J=8 Hz), 0.85 (s, 3H), 0.03 (s, 9H)

EXAMPLE 4-2

Production of (2R)-2-[(1R,7aR)-octahydro-4-trimethylsilyloxy-7a-methyl-1H-inden-1-yl]-propanal A 427 amount of Celite, 37 mg of sodium acetate, and 444 mg of pyridinium chlorochromate were placed in a 50 ml eggplant-shaped flask, then 10 ml of dichloromethane was added and the solution stirred. Thereafter, a dichloromethane solution (3 ml) of 426 mg of the compound (4-4), that is, (2R)-2-[(1R,7aR)-octahydro-4-trimethylsilyloxy-7a-methyl-1H-inden-1-yl]-propanol was added and the solution stirred at room temperature for 3.5 hours.

The reaction solution was filtered by Celite, then concentrated and the obtained residue was purified by a silica gel column to obtain the desired product (4-5), (2R)-2-[(1R, 7aR)-octahydro-4-trimethylsilyloxy-7a-methyl-1H-inden-1-yl]-propanol in an amount of 254 mg (yield 60%).

$^1$H-NMR (CDCl$_3$, δ ppm)

9.56 (d, 1H, J=3 Hz), 3.90 to 4.00 (m, 1H), 2.20 to 2.50 (m, 1H), 1.00 to 2.00 (m, 12H), 0.92 (d, 3H, J=6.3 Hz), 0.91 (s, 3H), 0.05 (s, 9H)

EXAMPLE 4-3

Production of methyl(4R)-4-[(1R,7aR)-octahydro-4-trimethylsilyloxy-7a-methyl-1H-inden-1-yl]-heptanoate

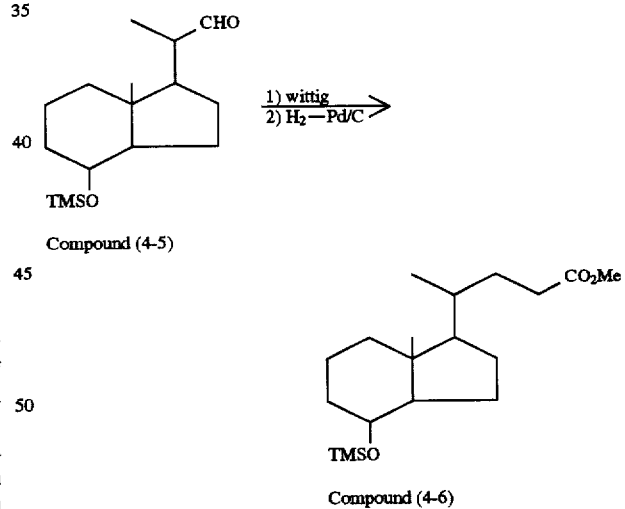

Compound (4-5)

Compound (4-6)

A 3.27 g amount of the compound (4-5), (2R)-2-[(1R, 7aR)-octahydro-4-trimethylsilyloxy-7a-methyl-1H-inden-1-yl]-propanal and 11.9 g of methyl (triphenylphosphoranilidene)acetate were placed in a 200 ml eggplant-shaped flask, 70 ml of toluene was added, and the solution was stirred at 80° C. over night. The solution was cooled to room temperature, then 100 ml of hexane was added, the precipitated deposit was filtered out, and the filtrate was concentrated under reduced pressure to obtain a crude product in an amount of 4.1 g. This was purified by a silica gel column (IR-60, 200 g, hexane/ethyl acetate=40/1 up) to obtain an oily substance in an amount of 3.82 g. This was dissolved in 200 ml of ethanol, then 0.5 g of 10% Pd/C was added, and the solution was stirred under a flow of hydrogen at room temperature over night. The Pd/C was removed by Celite filtration, then the result was concentrated to obtain 3.66 g of a crude product. This was purified by a silica gel column (hexane/ethyl acetate =20/1) to obtain the desired product methyl(4-6), (4R)-4-[(1R,7aR)-octahydro-4-trimethylsilyloxy-7a-methyl-1H-inden-1-yl]-heptanoate in an amount of 2.66 g [yield 67%, from compound (4-5)].

$^1$H-NMR (CDCl$_3$, δ ppm)

4.10 (brs, 1H), 3.66 (s, 3H), 2.10 to 2.30 (m, 2H), 1.00 to 2.00 (m, 15H), 0.93 (s, 3H), 0.90 (d, 3H, J=6.6 Hz), 0.05 (s, 9H)

EXAMPLE 4-4

Production of (4R)-4-[(1R, 7aR)-octahydro-4-trimethylsilyloxy-7a-methyl-1H-inden-1-yl]-p

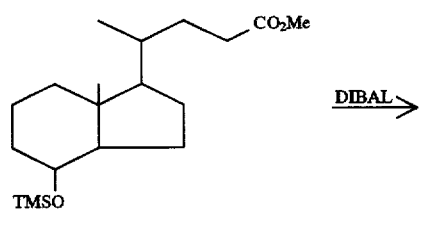

Compound (4-6)

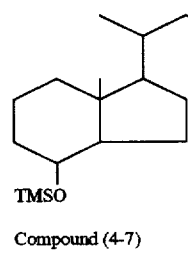

Compound (4-7)

A 3.79 g amount of the compound (4-6), methyl(4R)-4-[(1R,7aR)-octahydro-4-trimethylsilyloxy-7a-methyl-1H-inden-1-yl]-heptanoate was taken in a 300 ml eggplant-shaped flask, 100 ml of hexane was added, and the solution was stirred and cooled to −95° C. Thereafter 12.3 ml of a hexane solution (0.93 mol/liter) of diisobutylaluminum hydride was added and the solution stirred for 1 hour. A 100 ml amount of methanol was used to break down the excess reducing agent, then 30 ml of a saturated aqueous solution of ammonia chloride and 50 ml of ether were added and the solution was stirred at room temperature for 1 hour. The insolubles were removed by filtration by Celite, then the solution was separated and the aqueous layer was extracted by ether. The organic layer was washed two times by saturated saline in an amount of 50 ml, then was dried over anhydrous magnesium sulfate. The desiccant was filtered out, then the solvent was distilled off under reduced pressure to obtain a crude product in an amount of 4.07 g. This was purified by a silica gel column (Merck gel: 300 g, hexane/ethyl acetate=50/1) to obtain the desired product (4-7), (4R)-4-[(1R,7aR)-octahydro-4-trimethylsilyloxy-7a-methyl-1H-inden-1-yl]-pentanal in an amount of 3.17 g (yield 92%).

$^1$H-NMR (CDCl$_3$, δ ppm)

9.77 (t, 1H, J=2 Hz), 3.99 (d-like, 1H), 2.20 to 2.50 (m, 2H), 0.90 to 2.00 (m, 15H), 0.89 (d, 3H, J=7.3 Hz), 0.88 (s, 3H), 0.05 (s, 9H)

EXAMPLE 4-5

Production of (7R)-2-acetoxymethyl-7-[(1R,7aR)-octahydro-4-trimethylsilyloxy-7a-methyl-1H-

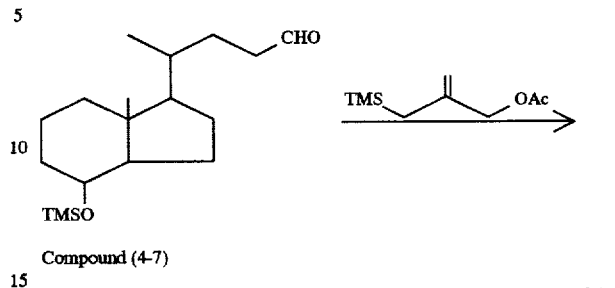

Compound (4-7)

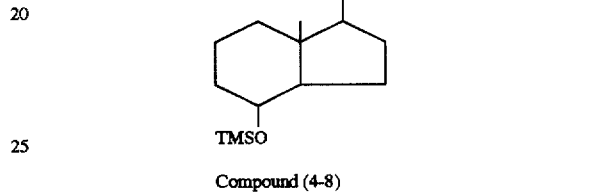

Compound (4-8)

A 1.72 g amount of the compound (4-7), (4R)-4-[(1R, 7aR)-octahydro-4-trimethylsilyloxy-7a-methyl-1H-inden-1-yl]-pentanal and 1.10 g of 2-(trimethylsilylmethyl)-2-propenyl acetate were taken in a 200 ml eggplant-shaped flask, then 30 ml of dichloromethane was added and the solution stirred at −78° C. To this was added 0.86 ml of BF•Et$_2$O, then the solution stirred at −78° C. for 1 hour. Further, 3 ml of triethylamine was added to stop the reaction, then the solvent was distilled off under reduced pressure. The obtained residue was purified by a silica gel column (IR-60, 150 g, hexane/ethyl acetate=50/1 to 9/1) to obtain the desired product (4-8), (7R)-2-acetoxymethyl-7-[(1R, 7aR)-octahydro-4-trimethylsilyloxy-7in an amount of 1.32 g (yield 57%).

$^1$H-NMR (CDCl$_3$, δ ppm)

5.16 (s, 1H), 5.06 (s, 2H), 4.56 (s, 2H), 3.99 (d-like, 1H), 3.60 to 3.70 (m, 1H), 2.10 (s, 3H), 1.00 to 2.30 (m, 20H), 0.91 (d, 3H, J=2.3 Hz), 0.88 (s, 3H), 0.05 ( s, 9H)

EXAMPLE 4-6

Production of (7R)-2-acetoxymethyl-4-(t-butyldimethylsilyloxy)-7-[(1R,7aR)-octahydro-4-trimethyl

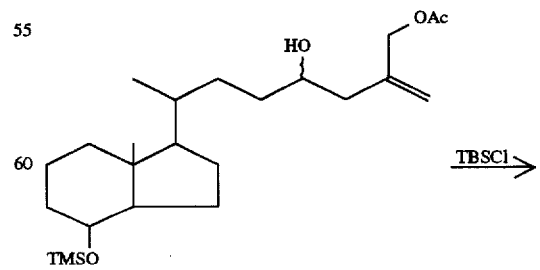

Compound (4-8)

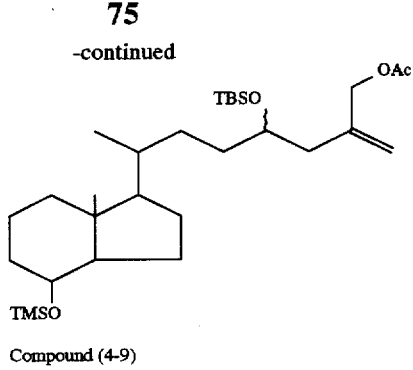

Compound (4-9)

A 2.18 g amount of the compound (4-8), (7R)-2-acetoxymethyl-7-[(1R,7aR)-octahydro-4-trimethylsilyloxy-7a-methyl-1H-inden-1-yl and 1.06 g of imidazole were placed in a 100 ml eggplant-shaped flask and dissolved in 30 ml of dichloromethane, then the solution stirred under ice-cooling. Thereafter, 1.16 g of t-butyldimethylsilyl chloride was added, then the solution was returned to room temperature and stirred 30 over night. To the reaction solution were added 50 ml of ether and 20 ml of water for separation, then extraction was performed from the aqueous layer by ether. The organic layer was washed by saturated saline and was dried over anhydrous magnesium sulfate. After filtration by Celite, the solvent was distilled off under reduced pressure. The obtained residue was purified by a silica gel column (IR-60, 80 g, hexane/ethyl acetate=3/1, 1/1) to obtain the desired product (4-9), (7R)-2-acetoxymethyl-4-(t-butyldimethylsilyloxy)-7-[(1R,7in an amount of 2.59 g (yield 93%).

$^1$H-NMR (CDCl$_3$, δ ppm)

5.09 (s, 1H), 4.96 (s, 2H), 4.54 (s, 2H), 3.98 (brs, 1H), 3.60 to 3.80 (m, 1H), 2.09 (s, 3H), 1.00 to 2.30 (m, 19H), 0.80 to 0.90 (m, 15H), 0.00 to 0.10 (m, 15H)

EXAMPLE 4-7

Production of (7R)-2-hydroxymethyl-4-(t-butyldimethylsilyloxy)-7-[(1R,7aR)-octahydro-4-trimethyl

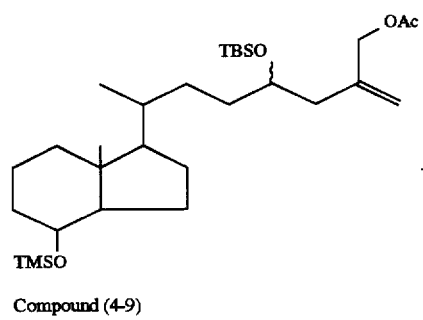

Compound (4-9)

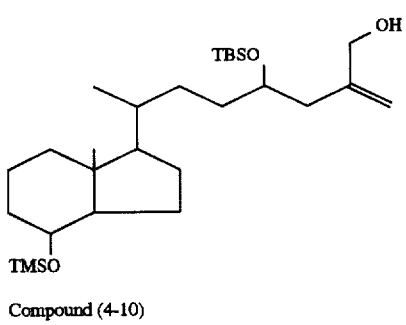

Compound (4-10)

A 2.59 g amount of the compound (4-9), (7R)-2-acetoxymethyl-4-(t-butyldimethylsilyloxy)-7-[(1R,7aR)-octahyde-4-trimethylsilyloxy-7a-methyl-1H-inden-1-yl]-octene was placed in a 100 ml eggplant-shaped flask and dissolved in 20 ml of tetrahydrofuran and 5 ml of methanol, then the solution was stirred under ice-cooling. Thereafter, 2 ml of a 4 N aqueous solution of lithium hydroxide was added, then the solution was stirred under ice cooling for 1 hour. The reaction solution was placed in 100 ml of ether and 20 ml of water and was extracted from the aqueous layer by ether. The organic layer was washed by a saturated aqueous solution of potassium hydrogensulfate, a saturated aqueous solution of sodium bicarbonate, and saturated saline and was dried over anhydrous magnesium sulfate. After filtration by Celite, the solvent was distilled off under reduced pressure to obtain a crude product in an amount of 2.39. This was purified by a silica gel column (IR-60, 80 g, hexane/ethyl acetate=19/1, 9/1) to obtain the desired product (4-10), (7R)-2-hydroxymethyl-4-(t-butyldimethylsilyloxy)-7-[(1R,7aR)-octahydro-4-trimethylsilyloxy-7a-methyl-1H-inden-1-yl]-octene in an amount of 2.15 g (yield 90%).

$^1$H-NMR (CDCl$_3$, δ ppm)

5.10 (s, 1H), 4.89 (s, 2H), 4.12 (d-like, 2H), 3.99 (brs, 1H), 3.70 to 3.80 (m, 1H), 0.90 to 2.50 (m, 20H), 0.80 to 0.95 (m, 15H), 0.00 to 0.10 (m, 15H)

EXAMPLE 4-8

Production of (7R,2R)-1, 2-epoxy-2-hydroxymethyl-4-(t-butyldimethylsilyloxy)-7-[(1R, 7aR)-octahydro-4-trimethylsilyloxy-7a-methyl-1H-inden-1-yl]-octane

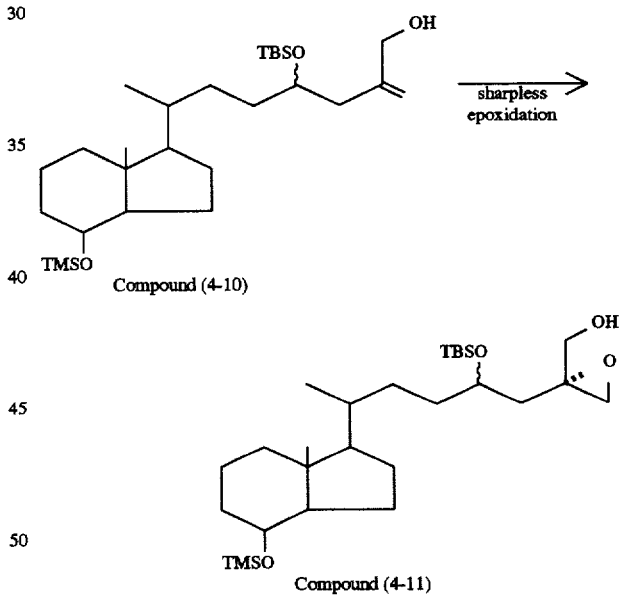

Compound (4-10)

Compound (4-11)

A 20 ml amount of dichloromethane was placed in a 200 ml eggplant-shaped flask, 1.36 ml of titanium tetraisopropoxide was added, then the solution was cooled to −20° C. and stirred. Thereafter, 1.05 g of D(−)-diethyl tartrate dissolved in 5 ml of dichloromethane and the solution stirred at −25° C. for 20 minutes was placed and then, 2.14 g of the compound (4-10), (7R)-2-hydroxymethyl-4-(t-butyldimethylsilyloxy)-7-[(1R, 7aR)-octahydro-4-trimethylsilyloxy-7a-methyl-1H-inden-1-yl]-octene, dissolved in 10 ml of dichloromethane, was added, then the solution was stirred for 30 minutes. Further, 4.3 ml of t-butyldiperoxide was added and the solution was stirred at the same temperature for 30 minutes. The reaction solution was poured into 20 ml of a 10% aqueous solution of tartaric acid, the solution was stirred at that temperature for 30 minutes and at room temperature for 1 hour, then separation was performed and extraction performed from the aqueous layer by dichloromethane. The organic layer was washed by a 10% aqueous solution of tartaric acid and saturated saline and was dried over anhydrous magnesium sulfate. After filtration by Celite, the solvent was distilled off under reduced pressure, the obtained residue was dissolved in 50 ml of ether, 18 ml of 1 N sodium hydroxide was added, then the solution was stirred under ice cooling for 1 hour. After separation, extraction was performed from the aqueous layer by ether. The organic layer was washed with saturated saline, then was dried over anhydrous magnesium sulfate, then filtered by Celite. The filtrate was concentrated under reduced pressure to obtain 2.40 g of a crude product. This was purified by a silica gel column (IR-60, 200 g, hexane/ethyl acetate=15/1 to 4/1) to obtain the desired product (4-11), (7R, 2R)-1,2-epoxy-2-hydroxymethyl-4-(t-butyldimethylsilyloxy)-7-[(1R,7aR)-octahydro-4-trimethylsilyloxy-7a-methyl-1H-inden-1-yl]-octane in an amount of 2.08 g (yield 94%).

$^1$H-NMR (CDCl$_3$, δ ppm)

3.99 (d-like, 1H), 3.50 to 3.80 (m, 3H), 2.50 to 2.90 (m, 2H), 1.00 to 2.00 (m, 20H), 0.80 to 1.00 (m, 15H), 0.00 to 0.10 (m, 15H)

EXAMPLE 4-9

Production of (7R,2R)-2-hydroxy-2-hydroxymethyl-4-(t-butyldimethylsilyloxy)-7-[(1R,7aR)-octahydro-4-trimethylsilyloxy-7a-methyl-1H-inden-1-yl]-octane

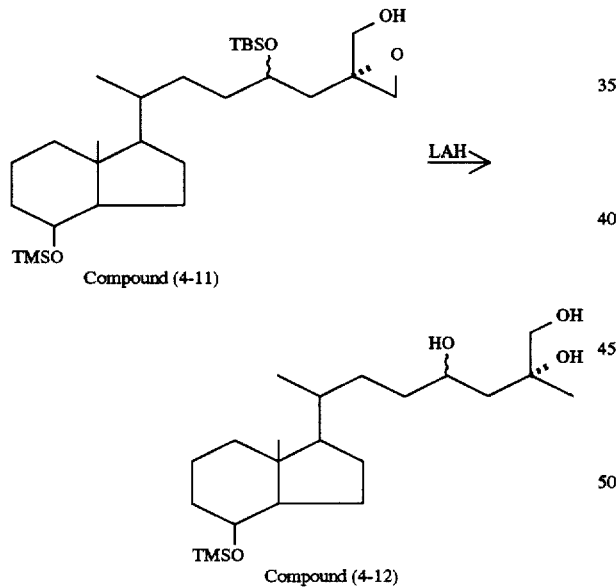

A 2.08 g amount of the compound (4-11), (7R,2R)-1,2-epoxy-2-hydroxymethyl-4-(t-butyldimethylsilyloxy)-7-[(1,7aR)-octahydro-4-trimethylsilyloxy-7a-methyl was placed in a 200 ml eggplant-shaped flask, 50 ml of ether was added, and the solution was stirred under ice-cooling. Thereafter, 380 mg of lithium aluminum hydride was added, then the solution was stirred under ice cooling for 15 minutes, at room temperature for 15 minutes, then was heated and refluxed for 2 hours. The solution was allowed to cool, then the excess reducing agent was broken down by a saturated aqueous solution of mirabilite, 100 ml of ethyl acetate was added, and the solution was stirred for 30 minutes. This solution was dried over anhydrous magnesium sulfate and filtered by cellite, then the solvent was distilled off under reduced pressure to obtain a crude product in an amount of 1.98 g. This was purified by a silica gel column (IR-60, 200 g, hexane/ethyl acetate=9/1 to 1/1) to obtain the desired product (4-12), (7R,2R)-2-hydroxy-2-hydroxymethyl-4-(t-butyldimethylsilyloxy)-7-[(R, 7aR)-octahydro-4-trimethylsilyloxy-7a-methyl-1H-inden-1-yl]-octane in an amount of 0.84 g (yield 54%).

$^1$H-NMR (CDCl$_3$, δ ppm)

3.99 (d-like, 1H), 3.75 to 3.85 (m, 1H), 3.62 (d, 1H J=11.2 Hz), 3.44 (d, 1H, J=12.4 Hz), 0.90 to 2.10 (m, 20H), 1.16 (s, 3H), 0.80 to 0.90 (s, 6H), 0.05 (s, 9H)

EXAMPLE 4-10

Production of (3R,5R)-5-{(3R)-3-[(1R,7aR)-octahydro-4-oxo-7a-methyl-1H-inde (3H)-furanon and (3R,5S)-5-{(3R)-3-[(1R,7aR)-octahydro-4-oxo-7a-methyl-1(3H)-furanon

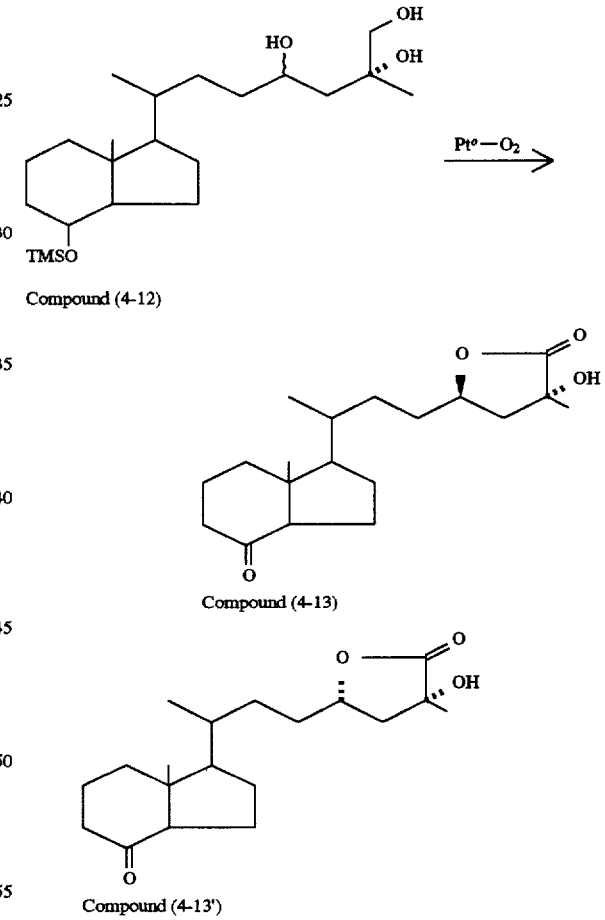

A 1.06 g amount of platinum oxide was placed in a 500 ml three-necked flask and suspended in 100 ml of water, and the solution was stirred over night in a hydrogen atmosphere. The atmosphere was returned to nitrogen, then 1.03 g of the compound (4-12), (7R,2R)-2-hydroxy-2-hydroxymethyl-4-(t-butyldimethylsilyloxy)-7-[(1R,7aR)-octahydro-4-trimethylsilyloxy-7a-methyl-1H-inden-1-yl]-octane and 30 mg of sodium laurate dissolved in 100 ml of acetone was added, and the solution was heated and stirred under an oxygen atmosphere for 3 days at 50° C. After being allowed to cool, the reaction solution was filtered by Celite, the filtrate was concentrated under reduced pressure, extraction was performed from the residue by ethyl acetate, and the organic layer was washed with saturated saline, then was dried over anhydrous magnesium sulfate. The solution was filtered by Celite, then the solvent was distilled off under reduced pressure to obtain a crude product in an amount of 1.05 g. This was purified by a silica gel column (IR-60, 200 g, hexane/ethyl acetate=3/1 to 1/3) to obtain the desired product (4-13), (3R,5R)-5-{(3R)-3-[(1R,7aR)-octahydro-4-oxo-7a-methyl-1H-inden-1-yl]-b (3H)-furanon in an amount of 369 mg (yield 44%) and (4-13'), (3R,5S)-5-{(3R)-3-[(1R,7aR)-octahydro-4-oxo-7a-methyl-1H-inden-1-yl]-butyl}-3-methyl-3-hydroxy-2(3H)-furanon in an amount of 350 mg (yield 41%).

Compound (4-13) $^1$H-NMR (CDCl$_3$, δ ppm)

4.50 to 4.60 (m, 1H), 1.20 to 2.60 (m, 20H), 1.52 (s, 3H), 0.97 (d, 3H, J=5.6 Hz), 0.65 (s, 3H)

Compound (4-13') $^1$H-NMR (CDCl$_3$, δ ppm)

4.20 to 4.40 (m, 1H), 1.20 to 2.60 (m, 20H), 1.49 (s, 3H), 0.98 (d, 3H, J=5.9 Hz), 0.65 (s, 3H)

EXAMPLE 4-11

Production of (3R,5R)-5-{(3R)-3-[(1R,7aR)-octahydro-4-oxo-7a-methyl-1H-inden-1-yl]-butyl}-3-methyl-3-trimethylsilyloxy-2(3H)-furanon

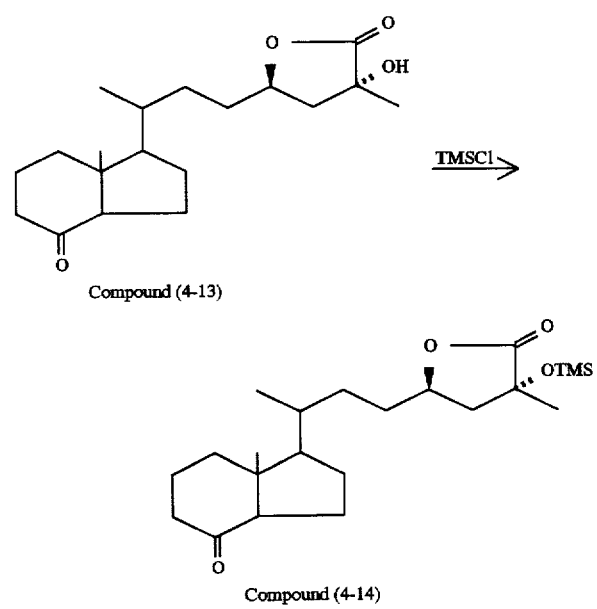

A 383 mg amount of the compound (4-13), (3R,5R)-5-{(3R)-3-[(1R,7aR)-octahydro-4-oxo-7a-methyl-1H-inden-1-yl]-butyl}-3-methyl-3-hydroxy-2(3H)-furanon and 250 mg of imidazole were placed in a 50 ml eggplant-shaped flask. Next, 10 ml of dried dichloromethane was added and the solution stirred. Under ice cooling, 0.23 ml of trimethylsilyl chloride was added, the solution was stirred at the same temperature for 60 minutes, then the reaction solution was poured into 50 ml of ether and 30 ml of water for extraction. The organic layer was washed 2 times with saturated saline, then was dried over anhydrous magnesium sulfate. The desiccant was filtered out and the solvent was distilled off under reduced pressure to obtain a crude product in an amount of 0.64 g. This was purified by a silica gel column (IR-60, 80 g hexane/ethyl acetate=9/1, 4/1) to obtain the desired product (4-14), (3R,5R)-5-{(3R)-3-[(1R,7aR)-octahydro-4-oxo-7a-methyl-(3H)-furanon in an amount of 423 mg (yield 90%).

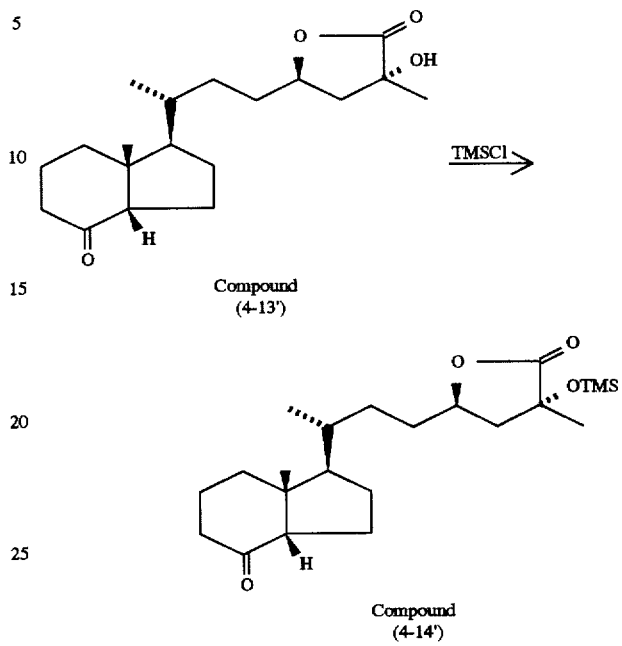

A 301 mg amount of the compound (4-13'), (3R, 5S)-5-{(3R)-3-[(1R,7aR)-octahydro-4-oxo-7a-methyl-1H-inden-1-yl]-butyl}- (3H)-furanon was treated in the same way to obtain the desired product (4-14'), (3R,5S)-5-{(3R)-3-[(1R, 7aR)-octahydro-4-oxo-7a-methyl-1(3H)-furanon in an amount of 358 mg (yield 75%).

Compound (4-14) $^1$H-NMR (CD$_3$Cl, δ ppm) 4.50 to 4.60 (m, 1H), 1.20 to 2.50 (m, 21H), 1.48 (s, 3H), 0.97 (d, 3H, J=5.9 Hz), 0.64 (s, 3H), 0.16 (s, 9H)

Compound (4-14') $^1$H-NMR (CD$_3$Cl, δ ppm)

4.20 to 4.35 (m, 1H), 1.10 to 2.50 (m, 21H), 1.48 (s, 3H), 0.98 (d, 3H, J=5.9 Hz), 0.64 (s, 3H), 0.19 (s, 9H)

EXAMPLE 4-12

Production of (3R,5R)-5-{(3R)-3-[(1R,7aR)-octahydro-4-bromomethylene-7a-methyl-(3H)-furanon

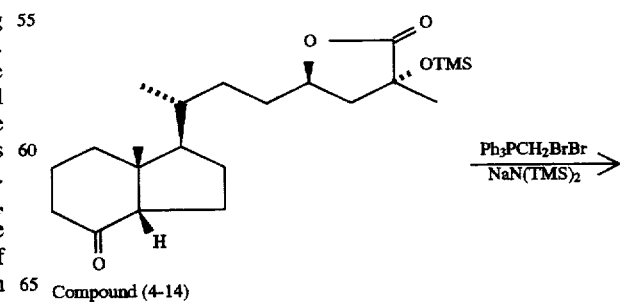

81

-continued

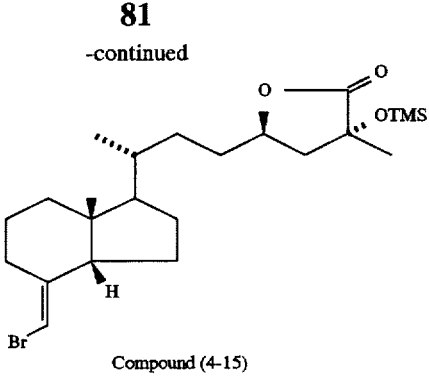

Compound (4-15)

A 1.03 g amount of bromomethylenetriphenylphosphonium bromide was taken in a 50 ml eggplant-shaped flask, 7 ml of dried tetrahydrofuran was added, and the solution was stirred and cooled by a −65° C. bath. Next, 2.35 ml of a 1 M solution of sodium bistrimethylsilylamide in tetrahydrofuran was added dropwise and the solution stirred at the same temperature for 10 minutes and at room temperature for 30 minutes. After cooling again to −65° C., 2 ml of a tetrahydrofuran solution of 186 mg of the compound (4-14), (3R,5R)-5-{(3R)-3-[(1R,7aR)-octahydro-4-oxo-7a-meth (3H)-furanon was dropwise added thereto. The cooling bath was removed, the solution was stirred at room temperature for 30 minutes, then hexane was added to the reaction solution and the solution stirred. The precipitate was filtered out, the solvent was distilled off under reduced pressure, and the resultant residue was purified by a silica gel column (IR-60, 200 g, hexane/ethyl acetate=40/1 to 19/1) to obtain the desired product (4-15), (3R,5R)-5-{(3R)-3-[(1R,7aR)-octahydro-4-bromomethylene-7a-methyl-1H-inden-1 (3H)-furanon in an amount of 78 mg (yield 35%).

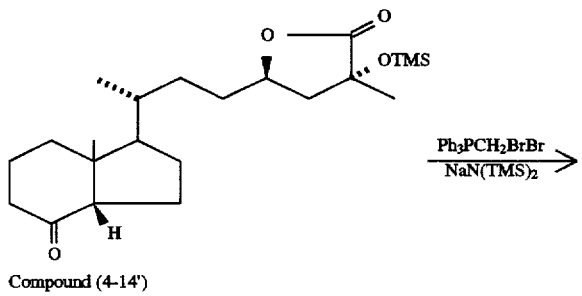

Compound (4-14')

Ph₃PCH₂BrBr / NaN(TMS)₂ →

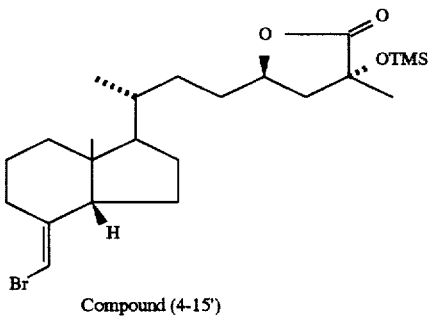

Compound (4-15')

A 169 mg amount of the compound (4-14'), (3R,5S)-5-{(3R)-3-[(1R,7aR)-octahydro-4-oxo-7a-methyl-1H-inden-1-yl]-b (3H)-furanon was treated in the same way to obtain the desired product (4-15'), (3R,5S)-5-{(3R)-3-[(1R,7aR)-octahydro-4-bromomethylene-(3H)-furanon in an amount of 103 mg (yield 51%).

82

Compound (4-15) ¹H-NMR (CD₃Cl, δ ppm)

5.65 (s, 1H), 4.40 to 4.50 (m, 1H), 2.80 to 2.90 (m, 1H), 1.20 to 2.40 (m, 21H), 1.48 (s, 3H), 0.94 (d, 3H J=6.4 Hz), 0.57 (s, 3H), 0.16 (s, 9H)

Compound (4-15') ¹H-NMR (CD₃Cl, δ ppm)

5.65 (s, 1H), 4.20 to 4.40 (m, 1H), 2.80 to 2.90 (m, 1H), 1.00 to 2.40 (m, 21H), 1.48 (s, 3H), 0.95 (d, 3H J=6.3 Hz), 0.57 (s, 3H), 0.19 (s, 9H)

REFERENCE EXAMPLE 4-1

Production of (23R,25R)-22-homo-1α-hydroxy-25-trimethylsilyloxy-vitamin D₃-26,23-lactone-1α,3-bis-t-butyldimethylsilylether

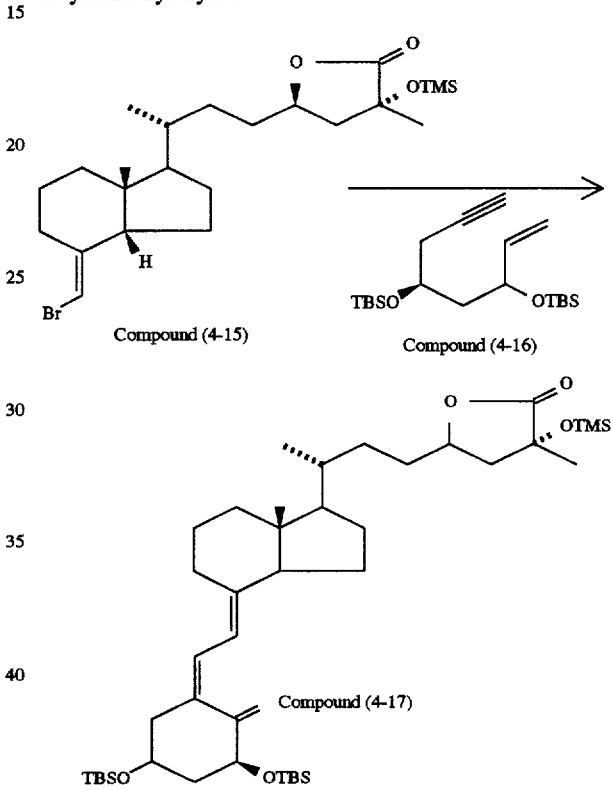

A 51.3 mg amount of triphenylphosphine was taken in a dried eggplant-shaped flask, then deaerated. Thereafter, 16.9 mg of tris(dibenzylideneacetone) dipalladium chloroform was added, followed by further deaeration, then 6.0 ml of a mixed solvent of distilled toluene/diisopropylethylamine= 1/1 was added under a nitrogen atmosphere and the solution stirred at room temperature for 20 minutes. Next, 77 mg of the compound (4-15), (3R,5R)-5-{(3R)-3-[(1R,7aR)-octahydro-4-bromomethylene-7a-methyl-1H-inden-1-yl]-butyl}-3-methyl-3-trimethylsilyloxy-2(3H)-furanon and 72 mg of the compound (4-16), (3S,5R)-bis(t-butyldimethylsilyloxy)-1-octen-7-yne were dissolved in 2 ml of a mixed solvent of distilled toluene/diisopropylethylamine=1/1 and added dropwise into the above reaction solution. The solution was heated and refluxed for 1.5 hours, then was returned to room temperature, then the reaction solution was poured into 50 ml of ethyl acetate and 10 ml of a saturated aqueous solution of potassium hydrogensulfate for extraction. The organic layer was washed with a saturated aqueous solution of sodium hydrogencarbonate and saturated saline, then was dried over anhydrous magnesium sulfate. The desiccant was filtered out and the solvent was distilled off under reduced pressure to obtain a crude product in an amount of 200 mg. This was purified by a silica gel column (Merck gel, 200 g, hexane/ethyl acetate=100/1 to 20/1) to obtain the desired product (4-17), (23R,25R)-22-homo-1α-hydroxy-25-trimethylsilyloxy-vitamin D₃-26,23-lactone-1α,3-bis-t-butyldimethylsilylether in an amount of 86.6 mg (yield 70%).

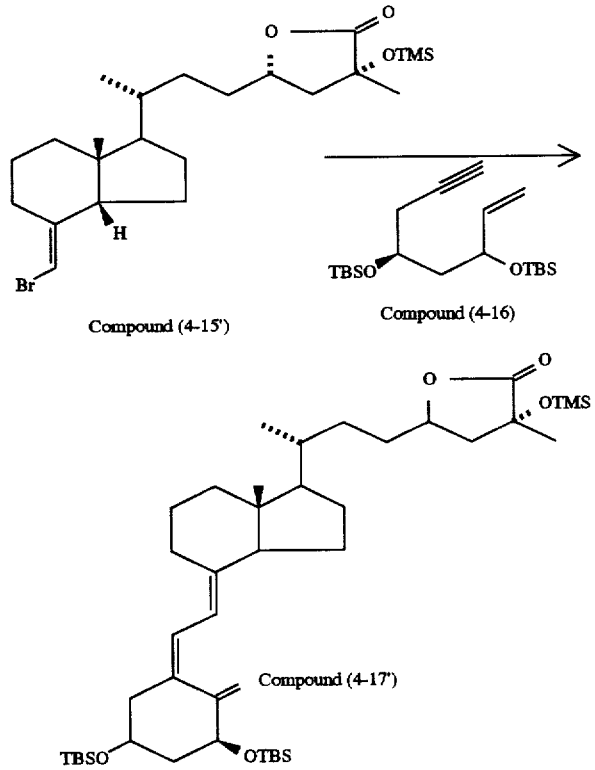

A 65 mg amount of the compound (4-15'), (3R,5S)-5{(3R)-3-[(1R,7aR)-octah (3H)-furanon was treated in the same way to obtain the desired product (4-17'), (23R,25R)-22-homo-1α-hydroxy-25-trimethylsilyloxy-vitamin D₃-26, 23-lactone-1α,3-bis-t-butyldimethylsilylether in an amount of 78 mg (yield Compound (4-17) ¹H-NMR (CDCl₃, δ ppm)

6.22 (d, J=11.8 Hz), 6.00 (d, J=11.2 Hz), 5.18 (brs, 1H), 4.86 (brs, 1H), 4.40 to 4.50 (m, 1H), 4.30 to 4.40 (m, 1H), 4.10 to 4.20 (m, 1H), 1–10 to 3.00 (m, 23H), 1.48 (s, 3H), 0.80 to 1.00 (m, 21H), 0.53 (s, 3H), 0.16 (s, 12H), 0.06 (s, 9H)

Compound (4-17') ¹H-NMR (CDCl₃, δ ppm)

6.23 (d-like, 1H), 6.00 (d-like, 1H), 5.18 (brs, 1H), 4.87 (brs, 1H), 4.40 to 4.50 (m, 1H), 4.15 to 4.40 (m, 2H), 1.00 to 2.90 (m, 23H), 1.48 (s, 3H), 0.60 to 0.80 (m, 21H), 0.53 (s, 3H), 0.19 (s, 12H), 0.11 (s, 9H)

REFERENCE EXAMPLE 4-2

Production of (23R,25R)-22-homo-1α,25-dihydroxy-vitamin D₃-26,23-lactone

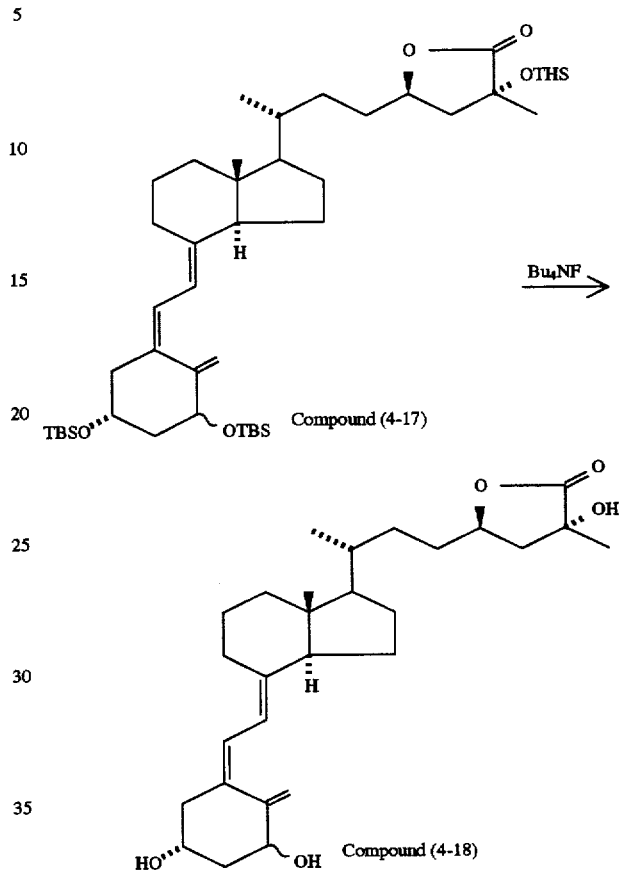

A 86 mg amount of the compound (4-17), (23R,25R)-22-homo-1α-hydroxy-25-trimethylsilyloxy-D₃-26, 23-lactone-1α,3-bis-t-butyldimethylsilylether, was taken in a 25 ml eggplant-shaped flask, then 10 ml of tetrahydrofuran was added and the solution stirred. Under ice cooling, 2.0 ml of a 1 M solution of tetrabutylammonium fluoride in tetrahydrofuran was added and the solution stirred at room temperature over night. Into the reaction solution was placed 5 ml of a saturated aqueous solution of potassium hydrogensulfate, then the solution was stirred for 30 minutes at room temperature. The reaction solution was extracted by ethyl acetate, the organic layer was washed with a saturated aqueous solution of sodium bicarbonate and saturated saline, then was dried over anhydrous magnesium sulfate. The desiccant was filtered out, the solvent was distilled off under reduced pressure, and the obtained crude product was purified by a silica gel column (IR-60, 80 g, hexane/ethyl acetate=2/3 to 1/3) to obtain the desired product (4-18), (23R, 25R)-22-homo-1α,25-dihydroxy-vitamin D₃-26,23-lactone in an amount of 23 mg (yield 48%).

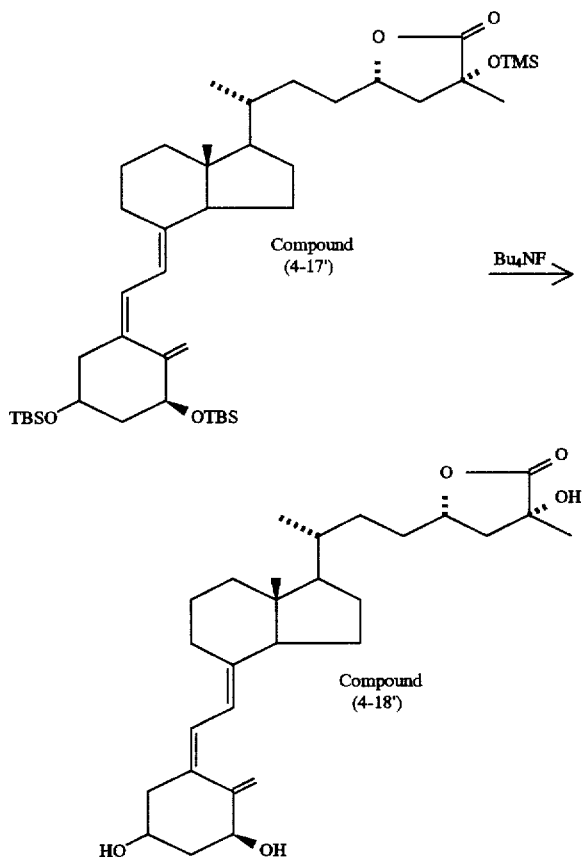

A 77 mg amount of the compound (4-17'), (23S,25R)-22-homo-1α-hydroxy-25-trimethylsilyl D$_3$-26,23-lactone-1α, 3-bis-t-butyldimethylsilylether was treated in the same way to obtain the desired product (4-18'), (23S,25R)-22-homo-1α,25-dihydroxy-vitamin D$_3$-26, 23-lactone in an amount of 11 mg (yield 24%).

Compound (4-18) $^1$H-NMR (CDCl$_3$, δ ppm)

6.38 (d, 1H, J=11.2 Hz), 6.02 (d, 1H, J=11.2 Hz), 5.33 (s, 1H), 5.00 (s, 1H), 4.50 to 4.65 (m, 1H), 4.40 to 4.20 (m, 2H), 1.00 to 3.00 (m, 23H), 1.49 (s, 3H), 0.95 (d, 3H J=6.3 Hz), 0.55 (s, 3H)

Compound (4-18') $^1$H-NMR (CDCl$_3$, δ ppm) 6.38 (d, 1H, J=11.2 Hz), 6.01 (d, 1H, J=11.2 Hz), 5.33 (s, 1H), 5.00 (s, 1H), 4.40 to 4.50 (m, 1H), 4.30 to 4.40 (m, 1H), 4.10 to 4.20 (m, 1H), 1.00 to 3.00 (m, 23H), 1.51 (s, 3H), 0.94 (d, 3H, J=6.3 Hz), 0.55 (s, 3H)

EXAMPLE 5-1

Measurement of Action of Suppression of Formation of Osteoclasts Induced by 1α,25(OH)$_2$D$_3$ Marrow cells were separated from the femur and tibia of mice (C57/Black 6, 5 weeks old, male) and incubated for 7 days in α-MEM containing 10% fetal calf serum in the presence of 1α,25(OH)$_2$D$_3$ (10$^{-8}$ M) with the addition of certain concentrations of compounds. The cells were dyed by tartaric acid resistant acid phosphase (TRAP), and the nuclei were dyed by Methyl Green. Next, the cells with at least 3 nuclei dyed by TRAP (osteoclasts) were counted under a microscope. The results are shown in the following Table 5-1.

TABLE 5-1

| Compound | | TRAP-positive MNC cell/well |
|---|---|---|
| 1α,25(OH)$_2$D$_3$(VD$_3$) | 10$^{-8}$M | 61.3 ± 16.0 |
| VD$_3$(10$^{-8}$M + Example 2-15 compound | 10$^{-9}$M | 47.7 ± 9.2 |
|  | 10$^{-8}$M | 34.5 ± 9.9 |
| VD$_3$(10$^{-8}$M) + Example 2-16 compound | 10$^{-9}$M | 23.2 ± 10.4 |
|  | 10$^{-8}$M | 24.0 ± 6.9 |
|  | 10$^{-7}$M | 17.5 ± 6.6 |

EXAMPLE 5-2

Affinity of compound to 1α,25-dihydroxyvitamin D$_3$ receptor (VDR) in chicken intestinal membrane cells The 1α,25-dihydroxyvitamin D$_3$ receptor in chicken intestinal membrane cells was isolated and evaluated in receptor affinity by a known method (Steroids, 37, 33–43 (1981). That is, 20 pg of [26,27-methyl- $^3$H]1α,25-dihydroxyvitamin D$_3$ (158 Ci/mmol, 16,800 dpm) and the test compound dissolved in 50 μl of ethanol were added to 12×75 mm polypropylene tubes. To these were added 0.2 mg amounts of 1α,25-dihydroxyvitamin D$_3$ receptor protein in chicken intestinal membrane cells and 1 mg of gelatin dissolved in 1 ml of a phosphate buffer (pH 7.4), then the solutions were reacted at 25° C. for one hour. After the reaction, 1 ml portions of a 40% solution of polyethylene glycol 6,000 were added to the tubes which were then shaken vigorously, then were centrifugally separated at 4° C. and 2,260×g for 60 minutes. The tubes of the sediment portions were cut off by a cutter knife and placed in liquid sintillation vials, a dioxane sintillator was added in amounts of 10 ml, and the radioactivity was measured by a liquid sintillation counter. The results are shown in the later given Table 5-2.

EXAMPLE 5-3

Affinity of compounds to vitamin D bonded proteins in fetal calf serum

The affinity of 25-hydroxyvitamin D$_3$ and a test compound to the vitamin D bonded proteins in fetal calf serum was determined by the method of J. Steroid Biochem. Molec. Biol. 41, 109–112 (1992). That is, 200 pg amounts of [26,27-methyl-$^3$H]25-hydroxyvitamin D$_3$ (28 Ci/mmol, 31,000 dpm) dissolved in a 0.01% Triton X-100 solution and the test compound dissolved in 10 μl of ethanol were added to 12×105 mm gas tubes. To these were added 0.2 ml amounts of a solution of fetal calf serum diluted 2500-fold by a 0.9% sodium chloride-containing phosphate buffer (pH 7.0), the solutions were reacted at 4° C. for 24 hours, then 0.5 ml of 0.5% charcoal, 0.075% dextrin and 0.5% bovine serum albumin solution were added, the solutions reacted at 4° C. for 15 minutes, then centrifugally separated at 2,260×g for 10 minutes. 0.5 ml amounts of the supernatent were taken in liquid sintillation vials and the radioactivity of the [26,27-methyl-$^3$H]25-hydroxyvitamin D$_3$ bonded to the vitamin D bonded protein was measured by a liquid sintillation counter.

The results are shown in the following Table 5-2.

TABLE 5-2

| Compound | 1α,25-(OH)$_2$ D$_3$ receptor (molar ratio) | Vitamin D-bonded protein (molar ratio) |
|---|---|---|
| 1α,25-(OH)$_2$D$_3$ | 1 | 1 |
| Example 1-11 compound (23) | 104 | 1.2 |
| Example 2-14 compound | 207 | 41.8 |
| Example 2-15 compound | 9.8 | 10.7 |
| Example 2-16 compound | 13.8 | 39.4 |
| Example 3-17 compound | 3.6 | >500 |

EXAMPLE 5-4

Synthesis of Collagen and Noncollagen Protein by osteoblasts

A murine osteoblast cell strain (MCJT cells) was dispersed in an α-MEM medium containing 10% fetal calf serum (FCS) (1×10$^4$ cells/ml medium). This was sown in 2 ml amounts in 35 mm incubation dishes, then incubated at 37° C. under 5% CO$^2$. After 4 days, after confluent was reached, the incubation solution was replaced by the same solution, then an ethanol solution of the test compound (1×10$^{-4}$ M and 1×10$^{-5}$ M) was added in 2 µl amounts. The control group had only ethanol added in an amount of 2 µl. The specimens were incubated at 37° C. under 5% CO$_2$. After 45 hours incubation, the medium was replaced by an α-MEM medium containing 0.1% bovine serum albumin (BSA), 0.1 mM ascorbic acid, and 0.5 mM fumaric acid-β-aminopropionitrile, the same amount of the ethanol solution of the test compound or ethanol as the previous time was added again, then incubation performed for 30 minutes, then 4 µCi of [$^3$H] proline were added to petri dishes and were allowed to be taken up by the osteoblasts for 3 hours. The amounts of the synthesized collagen and noncollagen protein were measured by the method of Perterkofsky et al. (Biochemistry, 10, 988–994 (1971)).

The results are shown in FIG. 1 and FIG. 2.

INDUSTRIAL APPLICABILITY

As explained above, the vitamin D$_3$ derivative according to the present invention is useful as an agent for the promotion of bone formation.

We claim:

1. A vitamin D$_3$ derivative represented by the following formula (I):

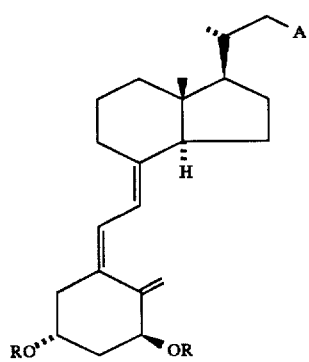

wherein, R is, independently, a hydrogen atom, triC$_1$ to C$_7$ hydrocarbon silyl group, a C$_2$ to C$_8$ acyl group, or a group forming an acetal bond together with an oxygen atom of a hydroxyl group, A is

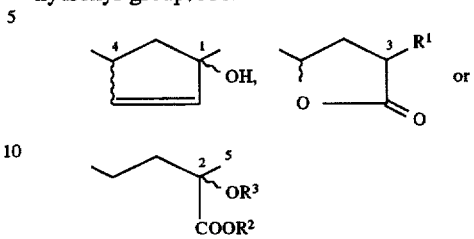

where, R$^1$ is a methyl group or a methylene group and when R$^1$ is a methylene group, the bond between the R$^1$ and the 3-position of the lactone ring is a double bond, R$^2$ is a hydrogen atom or a C$_1$ to C$_3$ alkyl group, R$^3$ is a hydrogen atom, or R$^2$ and R$^3$ together indicate a substitutable single methylene group.

2. A vitamin D$_3$ derivative as claimed in claim 1 represented by the following formula (1-1):

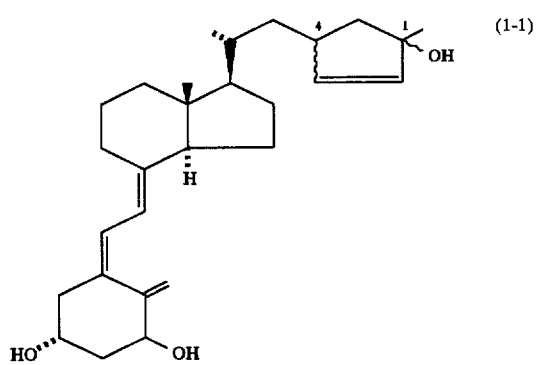

3. A vitamin D$_3$ derivative as claimed in claim 2, wherein the asymmetric center of the C-1 position of the cyclopentene ring of the formula (1-1) is an (R) configuration and the asymmetric center of the C-4 position is a (S) configuration.

4. A vitamin D$_3$ derivative as claimed in claim 2, wherein the asymmetric center of the C-1 position of the cyclopentene ring of the formula (1-1) is a (S) configuration and the asymmetric center of the C-4 position is a (S) configuration.

5. A process for producing a vitamin D$_3$ derivative according to claim 2 of the following formula (1-1):

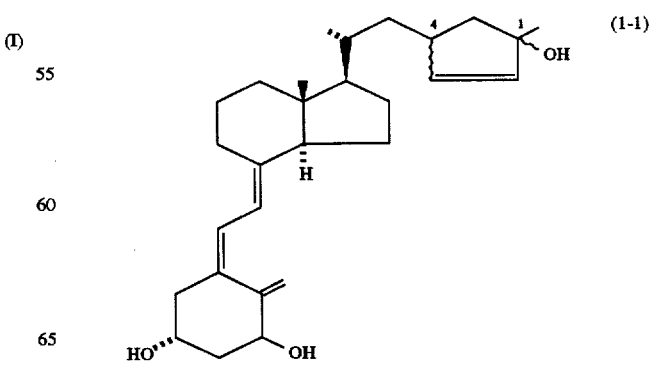

comprising reacting a cyclopentene derivative represented by the following formula (1-2):

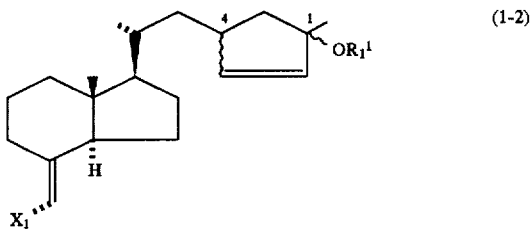

wherein, $R_1^1$ is a hydrogen atom, a tri$C_1$ to $C_7$ hydrocarbon silyl group, a $C_2$ to $C_7$ acyl group or a group forming an acetal bond together with an oxygen atom of a hydroxyl group and $X_1$ is a bromine atom or an iodine atom and an enyne derivative represented by the following formula (1-3):

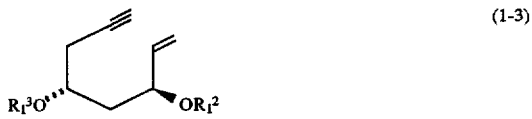

wherein, $R_1^2$, and $R_1^3$ are a hydrogen atom, a tri $C_1$ to $C_7$ hydrocarbon silyl group, a $C_2$ to $C_7$ acyl group, or a group forming an acetal bond together with an oxygen atom of a hydroxyl group in the presence of a palladium catalyst to produce a vitamin $D_3$ derivative represented by the following formula (1-4):

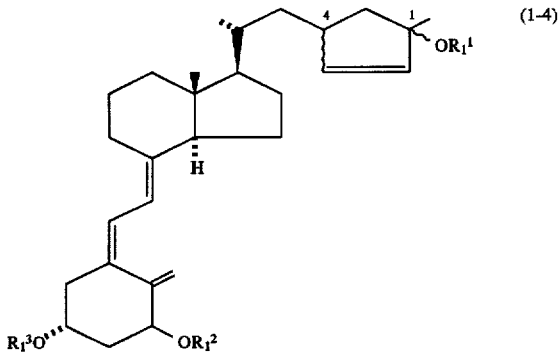

wherein, $R_1^1$, $R_1^2$, and $R_1^3$ are the same as defined above and, optionally, effecting a deblocking reaction.

6. A vitamin $D_3$ derivative as claimed in claim 1 represented by the following formula (2-1):

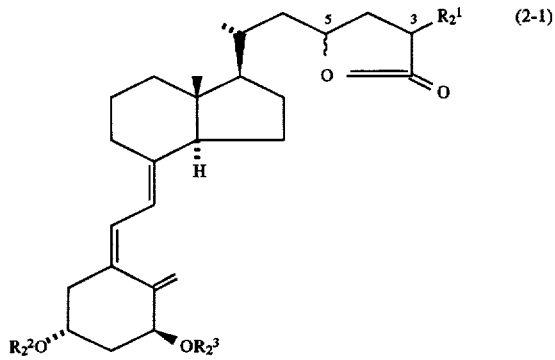

wherein, $R_2^1$ is a methyl group or methylene group provided that when $R_2^1$ is a methylene group, the bond between $R_2^1$ and the 3-position of the lactone ring is a double bond, $R_2^2$ and $R_2^3$ are the same or different and represent a hydrogen atom, tri$C_1$ to $C_7$ hydrocarbon silyl group, or a $C_2$ to $C_8$ acyl group.

7. A vitamin $D_3$ derivative as claimed in claim 6, wherein the $R^1$ of the above formula (2-1) is a methyl group, the asymmetric center of the 3-position of the lactone ring is an (S) configuration, and the asymmetric center of the 5-position is an (S) configuration.

8. A vitamin $D_3$ derivative as claimed in claim 6, wherein the $R_2^1$ of the above formula (2-1) is a methyl group, the asymmetric center of the 3-position of the lactone ring is an (S) configuration, and the asymmetric center of the 5-position is an (R) configuration.

9. A vitamin $D_3$ derivative as claimed in claim 6, wherein the $R_2^1$ of the above formula (2-1) is a methylene group, and the asymmetric center of the 5-position of the lactone ring is an (S) configuration.

10. A vitamin $D_3$ derivative as claimed in claim 6, wherein the $R_2^1$ of the above formula (2-1) is the methylene group, and the asymmetric center of the 5-position of the lactone ring is the (R) configuration.

11. A process for producing a vitamin $D_3$ derivative according to claim 12 represented by the following formula (2-1):

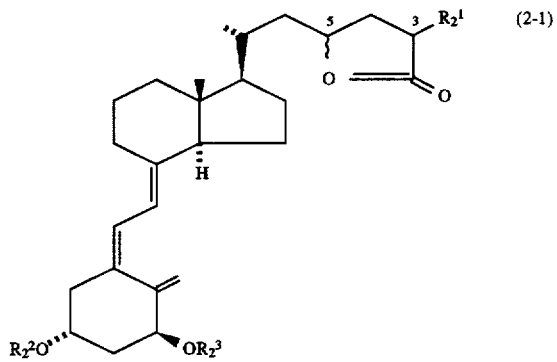

wherein, $R_2^1$, $R_2^2$, and $R_2^3$ are the same as defined, in claim 6 comprising reacting a lactone compound represented by the following formula (2-2):

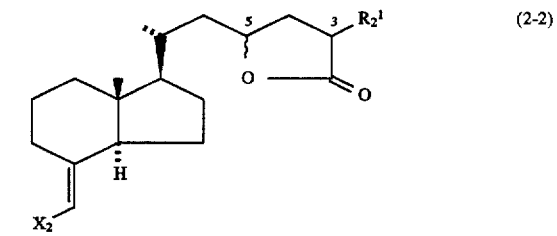

wherein, $R_2^1$ is the same as defined in claim 12 and $X_2$ is a bromine atom or an iodine atom, $R_2^1$ is a methyl group or a methylene group with an enyne compound represented by the following formula (2-10):

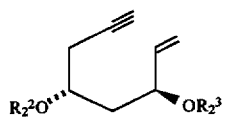
(2-10)

wherein, $R_2^2$ and $R_2^3$ are the same as defined in claim 12, in the presence of a palladium catalyst.

12. A vitamin $D_3$ derivative as claimed in claim 1 represented by the following formula (3-1):

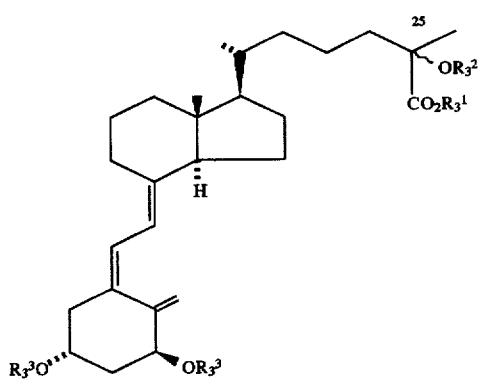
(3-1)

wherein, $R_3^1$ is a hydrogen atom or a $C_1$ to $C_3$ alkyl group and $R_3^2$ is a hydrogen atom or $R_3^1$ and $R_3^2$ together are a single substitutable group, $R_3^3$ is a hydrogen atom, triC$_1$ to C$_7$ hydrocarbon silyl group, a $C_2$ to $C_8$ acyl group, or group forming an acetal bond together with an oxygen atom of a hydroxyl group.

13. A vitamin $D_3$ derivative as claimed in claim 6, wherein the asymmetric center of the 25-position of the above formula (3-1) is a (R) configuration.

14. A vitamin $D_3$ derivative as claimed in claim 6, wherein the asymmetric center of the 25-position of the above formula (3-1) is a (S) configuration.

15. A process for producing a vitamin $D_3$ derivative according to claim 21, of the following formula (3-1):

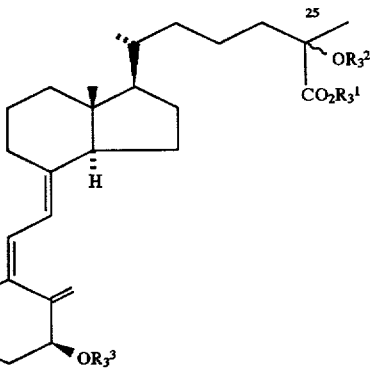
(3-1)

wherein, $R_3^1$, $R_3^2$, and $R_3^3$ are the same as defined in claim 12 comprising reacting a heptanoic acid derivative represented by the following formula (3-2):

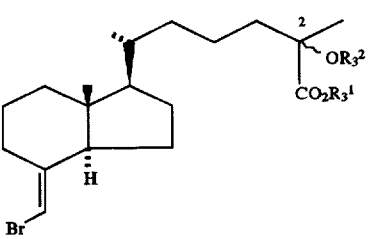
(3-2)

wherein $R_3^1$ and $R_3^2$ are the same as defined in claim 12, with an enyne compound represented by the following formula (3-5):

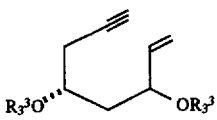
(3-5)

wherein, $R_3^1$ is the same as defined in claim 12 in the presence of a palladium catalyst.

* * * * *